(12) United States Patent
McCabe et al.

(10) Patent No.: US 9,622,918 B2
(45) Date of Patent: Apr. 18, 2017

(54) METHODS AND APPARATUS FOR APPLICATION OF NESTED ZERO WASTE EAR TO TRAVELING WEB

(75) Inventors: John McCabe, Sheboygan Falls, WI (US); Jeff Fritz, Plymouth, WI (US); Robert E. Andrews, Sheboygan Falls, WI (US)

(73) Assignee: Curt G. Joe, Inc., Sheboygan Falls, WI (US)

( * ) Notice: Subject to any disclaimer, the term of this patent is extended or adjusted under 35 U.S.C. 154(b) by 324 days.

(21) Appl. No.: 12/925,033

(22) Filed: Oct. 12, 2010

(65) Prior Publication Data

US 2011/0088233 A1    Apr. 21, 2011

Related U.S. Application Data

(63) Continuation-in-part of application No. 12/798,520, filed on Apr. 5, 2010, now Pat. No. 8,172,977.

(Continued)

(51) Int. Cl.
  *A61F 13/15*    (2006.01)
  *A61F 13/56*    (2006.01)
  (Continued)

(52) U.S. Cl.
  CPC .. *A61F 13/15723* (2013.01); *A61F 13/15756* (2013.01); *A61F 13/15804* (2013.01); *A61F 13/56* (2013.01); *A61F 13/565* (2013.01); *A61F 13/5622* (2013.01); *A61F 13/5638* (2013.01); *A61F 13/68* (2013.01); *A61F 13/72* (2013.01);
  (Continued)

(58) Field of Classification Search
  CPC .. A61F 13/56; A61F 13/5622; A61F 13/5638; A61F 13/68; A61F 13/72; A61F 13/581; A61F 2013/5677; A61F 2013/5694; A61F 2013/586; A61F 2013/587; A61F 2013/588; A61F 2013/51322
  USPC .... 604/385.02, 385.04, 385.27, 385.31, 387, 604/393, 385.23, 385.29, 385.3, 385.24, 604/386, 394, 38, 5.31
  See application file for complete search history.

(56) References Cited

U.S. PATENT DOCUMENTS

| 135,145 A | 1/1873 | Murphy |
| 293,353 A | 2/1884 | Purvis |

(Continued)

FOREIGN PATENT DOCUMENTS

| BE | 1007854 | 11/1995 |
| CA | 1146129 | 5/1983 |

(Continued)

OTHER PUBLICATIONS

U.S. Appl. No. 11/695,805, last action date Oct. 12, 2011, 605 pages.

(Continued)

*Primary Examiner* — Jacqueline Stephens
(74) *Attorney, Agent, or Firm* — Ryan Kromholz & Manion, S.C.

(57) ABSTRACT

The present invention provides a method of providing a disposable product with a contoured leg opening. In this method at least one chip is removed from at least one ear of a disposable product. The chip may be removed from an ear prior to attaching the ear to the chassis web. Alternatively, the chip may be removed from the ear after the ear is attached to the chassis web.

7 Claims, 41 Drawing Sheets

Related U.S. Application Data

(60) Provisional application No. 61/212,011, filed on Apr. 6, 2009, provisional application No. 61/212,619, filed on Apr. 14, 2009.

(51) Int. Cl.
    *A61F 13/68*     (2006.01)
    *A61F 13/72*     (2006.01)
    *A61F 13/58*     (2006.01)
    *A61F 13/513*     (2006.01)

(52) U.S. Cl.
    CPC ............. *A61F 2013/51322* (2013.01); *A61F 2013/5677* (2013.01); *A61F 2013/5694* (2013.01); *A61F 2013/586* (2013.01); *A61F 2013/587* (2013.01); *A61F 2013/588* (2013.01)

(56) References Cited

U.S. PATENT DOCUMENTS

| | | |
|---|---|---|
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,171,741 A | 5/1939 | Cohn et al. |
| 2,164,408 A | 7/1939 | Joa |
| 2,167,179 A | 7/1939 | Joa |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,618,608 A | 11/1971 | Brink |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg |
| 3,904,147 A | 9/1975 | Taitel et al. |
| 3,918,698 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |

(56) References Cited

U.S. PATENT DOCUMENTS

| | | | |
|---|---|---|---|
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | VanVliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A * | 5/1989 | Ahr ............... 604/389 |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack et al. |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,170 A | 10/1993 | Schaupp |
| 5,267,933 A | 12/1993 | Precoma |
| 5,273,228 A | 12/1993 | Yoshida et al. |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkotoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Hermann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |

(56) References Cited

U.S. PATENT DOCUMENTS

| | | | |
|---|---|---|---|
| 5,586,964 | A | 12/1996 | Chase |
| 5,602,747 | A | 2/1997 | Rajala |
| 5,603,794 | A | 2/1997 | Thomas |
| 5,624,420 | A | 4/1997 | Bridges et al. |
| 5,624,428 | A | 4/1997 | Sauer |
| 5,628,738 | A | 5/1997 | Suekane |
| 5,634,917 | A | 6/1997 | Fujioka et al. |
| 5,643,165 | A | 7/1997 | Klekamp |
| 5,643,396 | A | 7/1997 | Rajala et al. |
| 5,645,543 | A | 7/1997 | Nomura et al. |
| 5,659,229 | A | 8/1997 | Rajala |
| 5,660,657 | A | 8/1997 | Rajala et al. |
| 5,660,665 | A | 8/1997 | Jalonen |
| 5,683,376 | A | 11/1997 | Kato et al. |
| 5,683,531 | A | 11/1997 | Roessler et al. |
| RE35,687 | E | 12/1997 | Igaue et al. |
| 5,693,165 | A | 12/1997 | Schmitz |
| 5,699,653 | A | 12/1997 | Hartman et al. |
| 5,705,013 | A | 1/1998 | Nease et al. |
| 5,707,470 | A | 1/1998 | Rajala et al. |
| 5,711,832 | A | 1/1998 | Glaug et al. |
| 5,725,518 | A | 3/1998 | Coates |
| 5,725,714 | A | 3/1998 | Fujioka et al. |
| 5,743,994 | A | 4/1998 | Roessler et al. |
| 5,745,922 | A | 5/1998 | Rajala et al. |
| 5,746,869 | A | 5/1998 | Hayden et al. |
| 5,749,989 | A | 5/1998 | Linman et al. |
| 5,766,389 | A | 6/1998 | Brandon et al. |
| 5,788,797 | A | 8/1998 | Herrin et al. |
| 5,817,199 | A | 10/1998 | Brennecke et al. |
| 5,829,164 | A | 11/1998 | Kotitschke |
| 5,836,931 | A | 11/1998 | Toyoda et al. |
| 5,858,012 | A | 1/1999 | Yamaki et al. |
| 5,865,393 | A | 2/1999 | Kreft et al. |
| 5,868,727 | A | 2/1999 | Barr et al. |
| 5,876,027 | A | 3/1999 | Fukui et al. |
| 5,876,792 | A | 3/1999 | Caldwell |
| 5,879,500 | A | 3/1999 | Herrin et al. |
| 5,902,431 | A | 5/1999 | Wilkinson et al. |
| 5,932,039 | A | 8/1999 | Popp et al. |
| 5,938,193 | A | 8/1999 | Bluemle et al. |
| 5,964,390 | A | 10/1999 | Borresen et al. |
| 5,964,970 | A | 10/1999 | Woolwine et al. |
| 6,022,443 | A | 2/2000 | Rajala et al. |
| 6,036,805 | A | 3/2000 | McNichols |
| 6,043,836 | A | 3/2000 | Kerr et al. |
| 6,050,517 | A | 4/2000 | Dobrescu et al. |
| 6,074,110 | A | 6/2000 | Verlinden et al. |
| 6,076,442 | A | 6/2000 | Arterburn et al. |
| 6,098,249 | A | 8/2000 | Toney et al. |
| 6,123,792 | A | 9/2000 | Samida et al. |
| 6,171,432 | B1 | 1/2001 | Brisebois et al. |
| 6,183,576 | B1 | 2/2001 | Couillard et al. |
| 6,195,850 | B1 | 3/2001 | Melbye et al. |
| 6,210,386 | B1 | 4/2001 | Inoue |
| 6,212,859 | B1 | 4/2001 | Bielik, Jr. et al. |
| 6,214,147 | B1 | 4/2001 | Mortellite et al. |
| 6,250,048 | B1 | 6/2001 | Linkiewicz |
| 6,264,784 | B1 | 7/2001 | Menard et al. |
| 6,276,421 | B1 | 8/2001 | Valenti et al. |
| 6,276,587 | B1 | 8/2001 | Borresen et al. |
| 6,284,081 | B1 | 9/2001 | Vogt et al. |
| 6,287,287 | B1 * | 9/2001 | Elsberg ............... A61F 13/622 604/385.03 |
| 6,287,409 | B1 | 9/2001 | Stephany |
| 6,306,122 | B1 | 10/2001 | Narawa et al. |
| 6,309,336 | B1 | 10/2001 | Muessig et al. |
| 6,312,420 | B1 | 11/2001 | Sasaki et al. |
| 6,314,333 | B1 | 11/2001 | Rajala et al. |
| 6,315,022 | B1 | 11/2001 | Herrin et al. |
| 6,336,921 | B1 | 1/2002 | Kato et al. |
| 6,358,350 | B1 | 3/2002 | Glaug et al. |
| 6,369,291 | B1 | 4/2002 | Uchimoto et al. |
| 6,375,769 | B1 | 4/2002 | Quereshi et al. |
| 6,391,013 | B1 | 5/2002 | Suzuki et al. |
| 6,416,697 | B1 | 7/2002 | Venturino et al. |
| 6,431,038 | B2 | 8/2002 | Couturier |
| 6,440,246 | B1 | 8/2002 | Vogt et al. |
| 6,443,389 | B1 | 9/2002 | Palone |
| 6,446,795 | B1 | 9/2002 | Allen et al. |
| 6,473,669 | B2 | 10/2002 | Rajala et al. |
| 6,475,325 | B1 | 11/2002 | Parrish et al. |
| 6,478,786 | B1 | 11/2002 | Gloug et al. |
| 6,482,278 | B1 | 11/2002 | McCabe et al. |
| 6,494,244 | B2 | 12/2002 | Parrish et al. |
| 6,514,233 | B1 | 2/2003 | Glaug |
| 6,521,320 | B2 | 2/2003 | McCabe et al. |
| 6,523,595 | B1 | 2/2003 | Milner et al. |
| 6,524,423 | B1 | 2/2003 | Hilt et al. |
| 6,533,879 | B2 | 3/2003 | Quereshi et al. |
| 1,957,651 | A1 | 4/2003 | Joa |
| 6,540,857 | B1 | 4/2003 | Coenen et al. |
| 6,544,375 | B1 | 4/2003 | Schmitz |
| 6,551,228 | B1 | 4/2003 | Richards |
| 6,551,430 | B1 | 4/2003 | Glaug et al. |
| 6,554,815 | B1 | 4/2003 | Umebayashi |
| 6,569,275 | B1 | 5/2003 | Popp et al. |
| 6,572,520 | B2 | 6/2003 | Blumle |
| 6,581,517 | B1 | 6/2003 | Becker et al. |
| 6,585,841 | B1 | 7/2003 | Popp et al. |
| 6,589,149 | B1 | 7/2003 | VanEperen et al. |
| 6,596,107 | B2 | 7/2003 | Stopher |
| 6,596,108 | B2 | 7/2003 | McCabe |
| 6,605,172 | B1 | 8/2003 | Anderson et al. |
| 6,605,173 | B2 | 8/2003 | Glaug et al. |
| 6,637,583 | B1 | 10/2003 | Andersson |
| 6,648,122 | B1 | 11/2003 | Hirsch et al. |
| 6,649,010 | B2 | 11/2003 | Parrish et al. |
| 6,656,309 | B1 | 12/2003 | Parker et al. |
| 6,659,150 | B1 | 12/2003 | Perkins et al. |
| 6,659,991 | B2 | 12/2003 | Suckane |
| 6,675,552 | B2 | 1/2004 | Kunz et al. |
| 6,684,925 | B2 | 2/2004 | Nagate et al. |
| 6,722,494 | B2 | 4/2004 | Nakakado |
| 6,730,189 | B1 | 5/2004 | Franzmann et al. |
| 6,736,923 | B1 | 5/2004 | Franzmann et al. |
| 6,743,324 | B2 | 6/2004 | Hargett et al. |
| 6,750,466 | B2 | 6/2004 | Guha et al. |
| 6,758,109 | B2 | 7/2004 | Nakakado |
| 6,766,817 | B2 | 7/2004 | Dias da Silva |
| 6,808,582 | B2 | 10/2004 | Popp et al. |
| D497,991 | S | 11/2004 | Otsubo et al. |
| 6,814,217 | B2 | 11/2004 | Blumenthal et al. |
| 6,820,671 | B2 | 11/2004 | Calvert |
| 6,837,840 | B2 | 1/2005 | Yonekawa et al. |
| 6,840,616 | B2 | 1/2005 | Summers |
| 6,852,186 | B1 | 2/2005 | Matsuda et al. |
| 6,875,202 | B2 | 4/2005 | Kumasaka et al. |
| 6,893,528 | B2 | 5/2005 | Middelstadt et al. |
| 6,913,718 | B2 | 7/2005 | Ducker et al. |
| 6,918,404 | B2 | 7/2005 | Dias da Silva |
| 6,936,129 | B2 | 8/2005 | Karami et al. |
| 6,976,521 | B2 | 12/2005 | Mlinar et al. |
| 6,978,486 | B2 | 12/2005 | Zhou et al. |
| 7,017,820 | B1 | 3/2006 | Brunner |
| 7,045,031 | B2 | 5/2006 | Popp et al. |
| 7,066,586 | B2 | 6/2006 | de Silva |
| 7,077,393 | B2 | 7/2006 | Ishida |
| 7,130,710 | B2 | 10/2006 | Popp et al. |
| 7,172,666 | B2 | 2/2007 | Groves et al. |
| 7,195,684 | B2 | 3/2007 | Satoh |
| 7,201,345 | B2 | 4/2007 | Werner et al. |
| 7,214,174 | B2 | 5/2007 | Allen et al. |
| 7,214,287 | B2 | 5/2007 | Shiomi |
| 7,247,219 | B2 | 7/2007 | O'Dowd |
| 7,303,708 | B2 | 12/2007 | Andrews et al. |
| 7,380,213 | B2 | 5/2008 | Pokorny et al. |
| 7,398,870 | B2 | 7/2008 | McCabe |
| 7,452,436 | B2 | 11/2008 | Andrews |
| 7,533,709 | B2 | 5/2009 | Meyer |
| 7,537,215 | B2 | 5/2009 | Beaudoin et al. |
| 7,587,966 | B2 | 9/2009 | Nakakado et al. |
| 7,618,513 | B2 | 11/2009 | Meyer |
| 7,638,014 | B2 | 12/2009 | Coose et al. |

(56) References Cited

U.S. PATENT DOCUMENTS

| | | |
|---|---|---|
| 7,640,962 B2 | 1/2010 | Meyer et al. |
| 7,695,464 B2 * | 4/2010 | Fletcher et al. ............... 604/389 |
| 7,703,599 B2 | 4/2010 | Meyer |
| 7,708,849 B2 | 5/2010 | McCabe |
| 7,770,712 B2 | 8/2010 | McCabe |
| 7,780,052 B2 | 8/2010 | McCabe |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 2001/0012813 A1 | 8/2001 | Bluemle |
| 2001/0017181 A1 | 8/2001 | Otruba et al. |
| 2002/0002358 A1 | 1/2002 | Durrance et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0138064 A1 * | 9/2002 | Datta ................ A61F 13/49009 604/391 |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0121614 A1 | 7/2003 | Tabor |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0082931 A1 * | 4/2004 | Tani ............................. 604/387 |
| 2004/0087425 A1 | 5/2004 | Ng et al. |
| 2004/0112517 A1 | 6/2004 | Groves et al. |
| 2004/0122413 A1 * | 6/2004 | Roessler et al. ............. 604/386 |
| 2004/0164482 A1 | 8/2004 | Edinger |
| 2004/0182497 A1 | 9/2004 | Lowrey |
| 2005/0000628 A1 | 1/2005 | Norrley |
| 2005/0022476 A1 | 2/2005 | Hamer et al. |
| 2005/0077418 A1 | 4/2005 | Werner et al. |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |
| 2007/0142808 A1 | 6/2007 | Wada et al. |
| 2008/0210067 A1 | 9/2008 | Schlinz et al. |
| 2008/0223537 A1 | 9/2008 | Wiedmann |
| 2009/0020211 A1 | 1/2009 | Andrews et al. |
| 2009/0198205 A1 | 8/2009 | Malowaniec et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193138 A1 | 8/2010 | Eckstein |
| 2010/0193155 A1 | 8/2010 | Nakatani |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| CA | 2337700 | 8/2008 |
| CA | 2407867 | 6/2010 |
| CA | 2699136 | 10/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 6/1986 |
| EP | 0304140 | 8/1987 |
| EP | 0439897 | 2/1990 |
| EP | 0455231 | 11/1991 |
| EP | 0510251 | 10/1992 |
| EP | 0652175 | 5/1995 |
| EP | 0811473 | 12/1997 |
| EP | 0901780 | 3/1999 |
| EP | 0990588 | 4/2000 |
| EP | 1132325 | 9/2001 |
| EP | 1199057 | 4/2002 |
| EP | 1272347 | 1/2003 |
| EP | 1366734 | 12/2003 |
| EP | 1189564 | 3/2005 |
| EP | 1571249 | 9/2005 |
| EP | 1619008 | 1/2006 |
| EP | 1707168 | 4/2006 |
| EP | 1719484 | 11/2006 |
| EP | 1726414 | 11/2006 |
| EP | 1302424 | 12/2006 |
| EP | 1801045 | 6/2007 |
| EP | 1941853 | 7/2008 |
| EP | 1941853 | 9/2008 |
| EP | 1941853 A1 | 9/2008 |
| EP | 1994919 | 11/2008 |
| EP | 2020215 | 2/2009 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 0206208 | 12/1986 |
| FR | 1132325 | 10/2006 |
| FR | 2891811 | 4/2007 |
| GB | 191101501 | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |

(56) References Cited

FOREIGN PATENT DOCUMENTS

| | | |
|---|---|---|
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 9299398 | 11/1997 |
| JP | 10035621 | 2/1998 |
| JP | 10-277091 | 10/1998 |
| JP | 2007-44374 | 2/2007 |
| SE | 0602047 | 5/2007 |
| SE | 0601003-7 | 6/2007 |
| SE | 0601145-6 | 10/2009 |
| WO | WO2008155618 | 12/1988 |
| WO | WO9403301 | 2/1994 |
| WO | WO 97/325552 | 9/1997 |
| WO | WO9747265 | 12/1997 |
| WO | WO 9747810 | 12/1997 |
| WO | WO9821134 | 5/1998 |
| WO | WO 9907319 | 2/1999 |
| WO | WO 9913813 | 3/1999 |
| WO | WO9932385 | 7/1999 |
| WO | WO 9965437 | 12/1999 |
| WO | WO 0143682 | 6/2001 |
| WO | WO 0172237 | 10/2001 |
| WO | WO0172237 | 10/2001 |
| WO | WO 2004007329 | 1/2004 |
| WO | WO 2005075163 | 1/2005 |
| WO | WO2007029115 | 3/2007 |
| WO | WO 2007039800 | 4/2007 |
| WO | WO2007126347 | 11/2007 |
| WO | WO2008001209 | 1/2008 |
| WO | WO 2008/036706 | 3/2008 |
| WO | WO 2008/155618 | 12/2008 |
| WO | WO 2010/028786 | 3/2010 |
| WO | WO 2011/101773 | 8/2011 |

OTHER PUBLICATIONS

U.S. Appl. No. 12/284,774, last action date Aug. 17, 2010, 254 pages.
Reciprocating Mechanisms, Ingenious Mechanisms for Designers and Inventors, Franklin Jones vol. 1.
European Search Report, 10250726.6, Jul. 27, 2010.
USPTO Office Action regarding U.S. Appl. No. 12/151,667, dated Apr. 20, 2011, 29 pages.
Office Action response regarding U.S. Appl. No. 12/151,667, dated Jun. 20, 2011, 7 pages.
USPTO Notice of Allowance regarding U.S. Appl. No. 12/151,667, dated Jul. 13, 2011, 5 pages.
USPTO Examiner's Interview Summary regarding U.S. Appl. No. 12/151,667, dated Jul. 13, 2011, 3 pages.
USPTO Notice of Allowance and Examiner's Interview Summary regarding U.S. Appl. No. 12/798,520, dated Jan. 25, 2012, 5 pages.
International Search Report dated Mar. 9, 2012 regarding EP Application No. 11184738.0, 6 pages.
International Search Report dated Apr. 4, 2013 regarding EP Application No. 12173311.7, 6 pages.
European Search Report for Appln. No. 12188581.8, 6 pages, dated Sep. 12, 2014.
Third Party Observations regarding EP08251662.6, dated Nov. 11, 2014, 9 pages.

\* cited by examiner

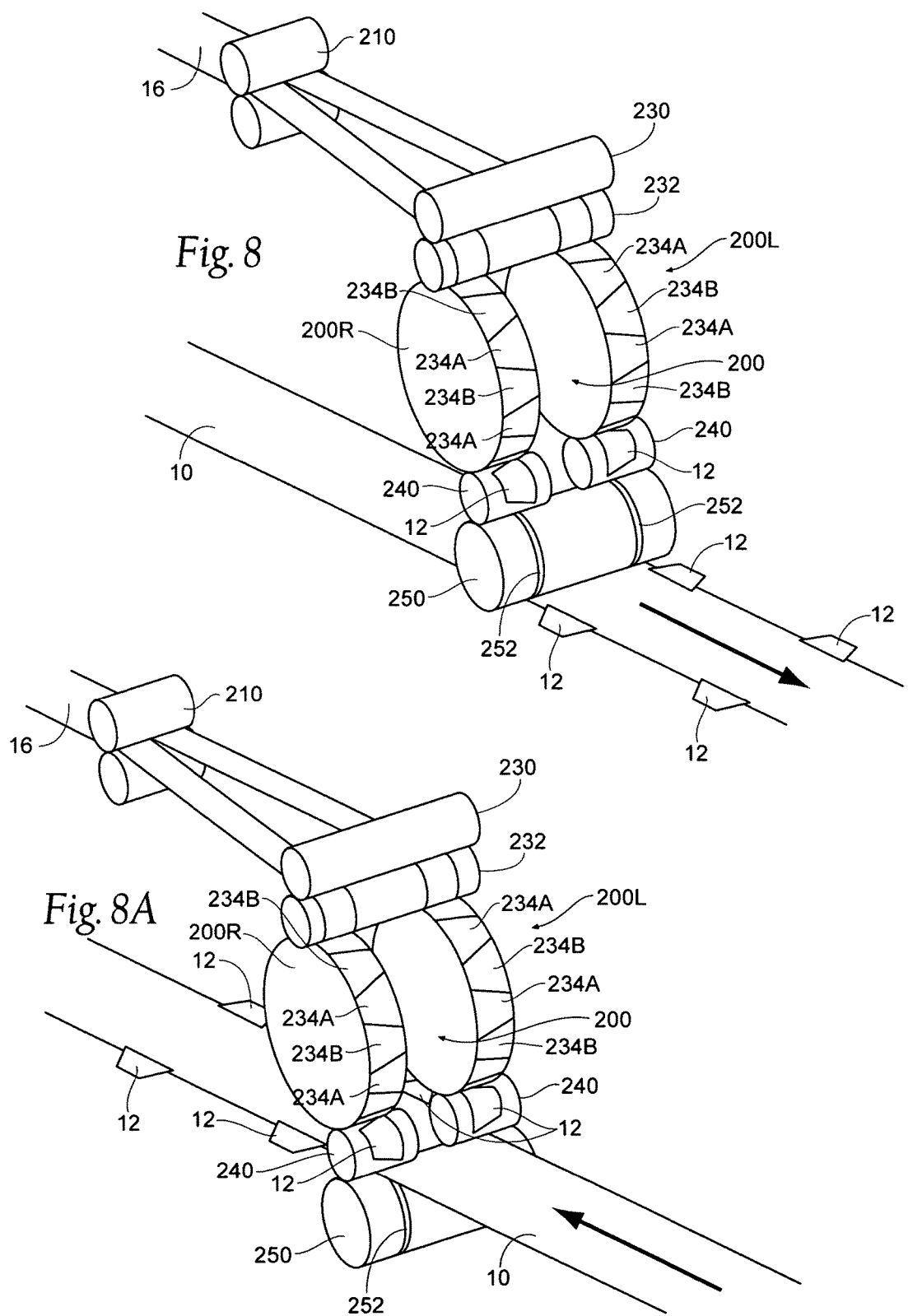

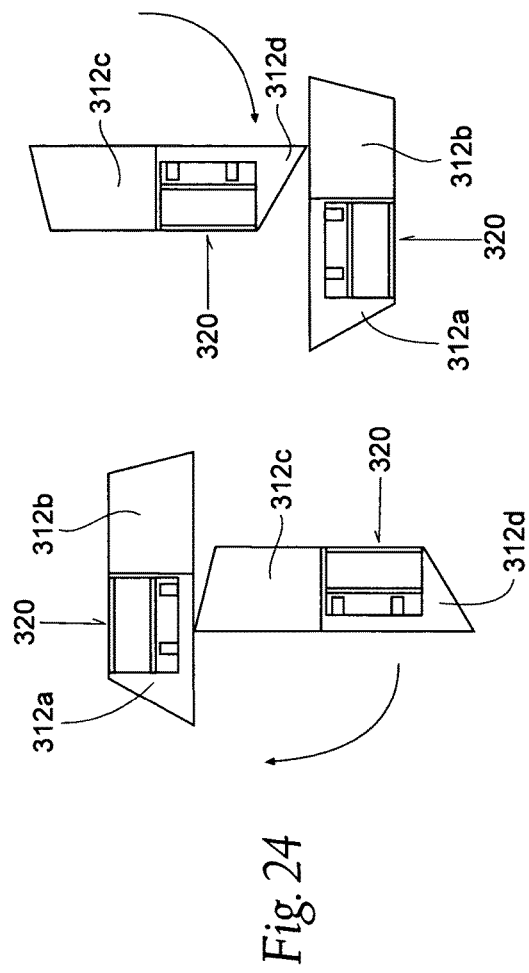
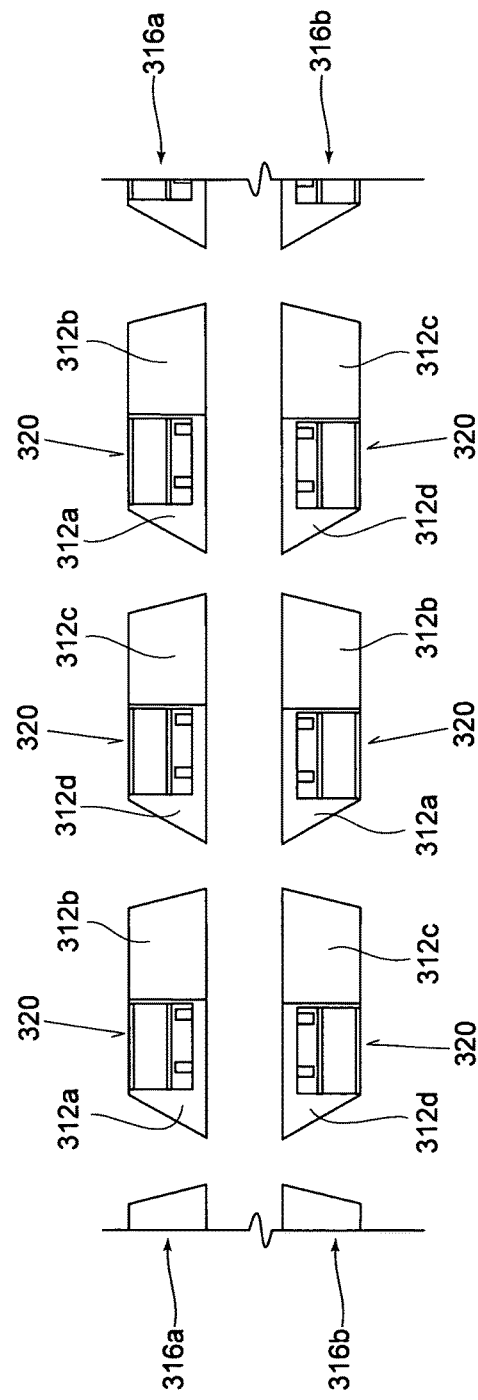

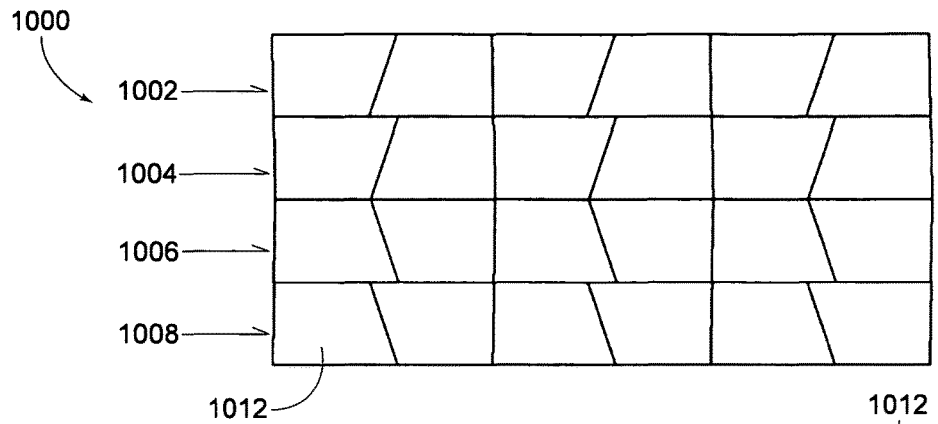
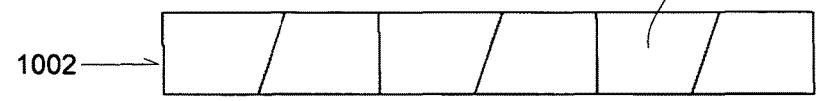
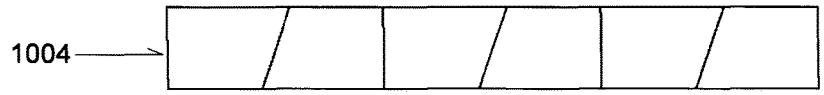
Fig. 30
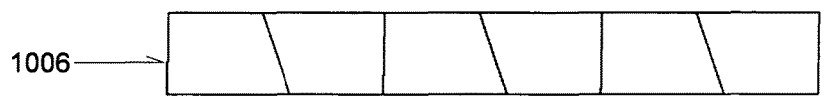
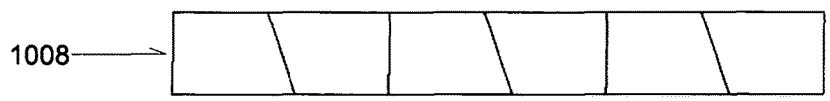
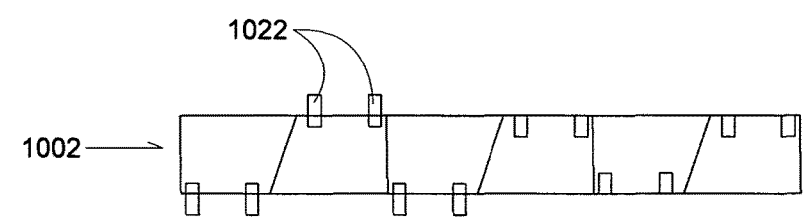
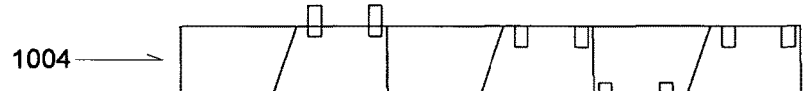
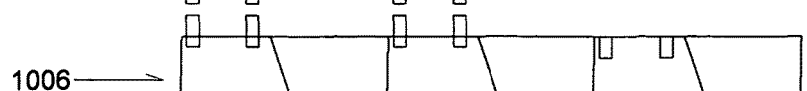
Fig. 31
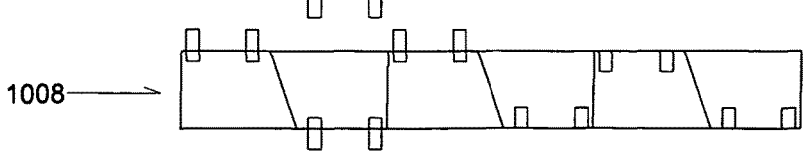

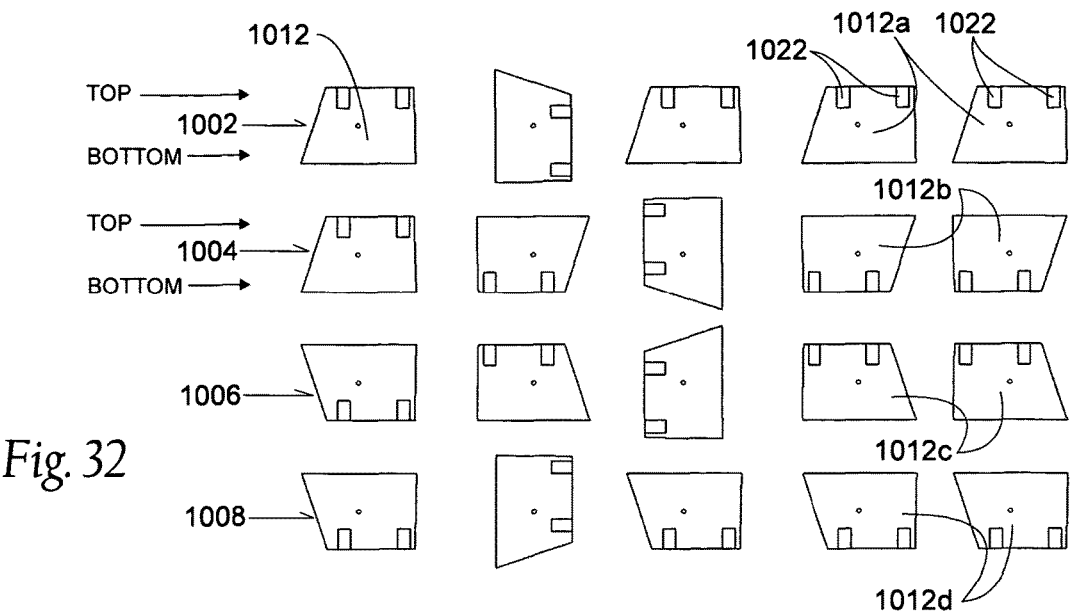
Fig. 32
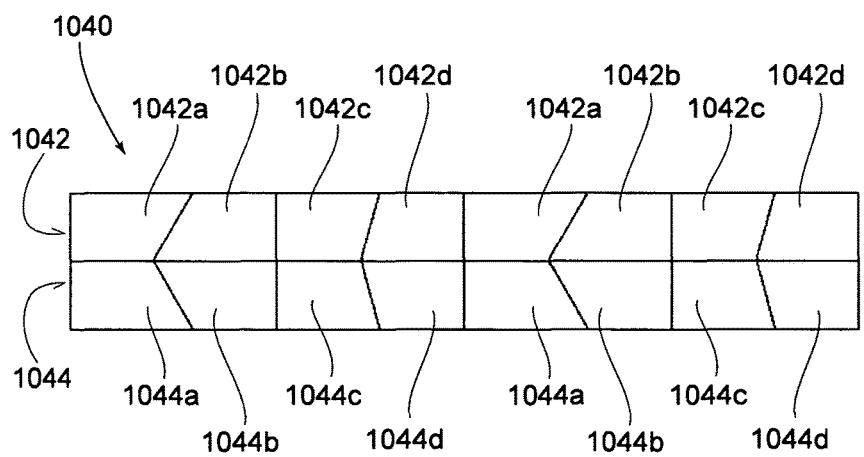
Fig. 33
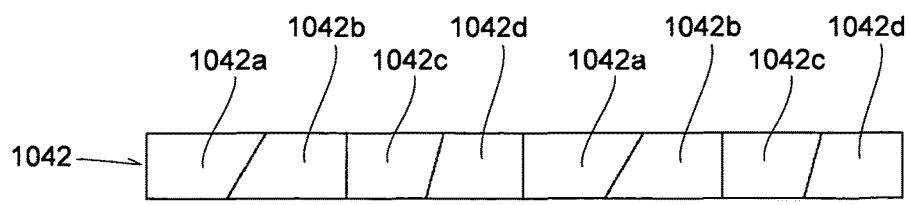
Fig. 34
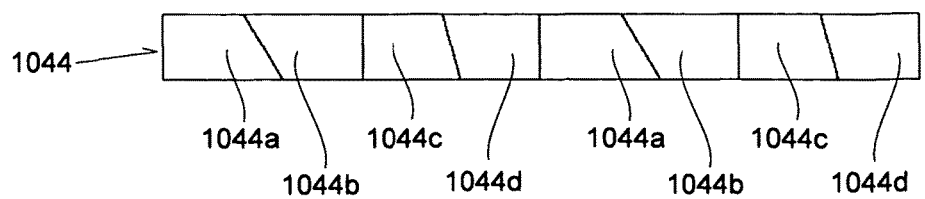

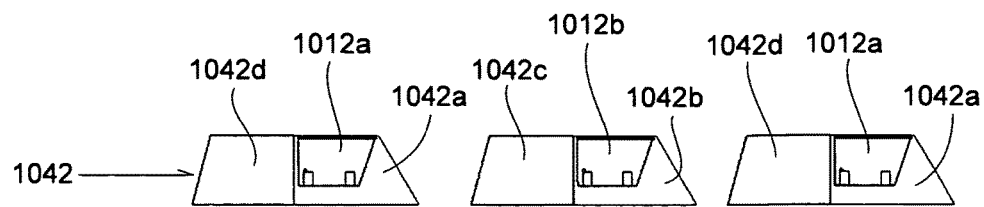
Fig. 38
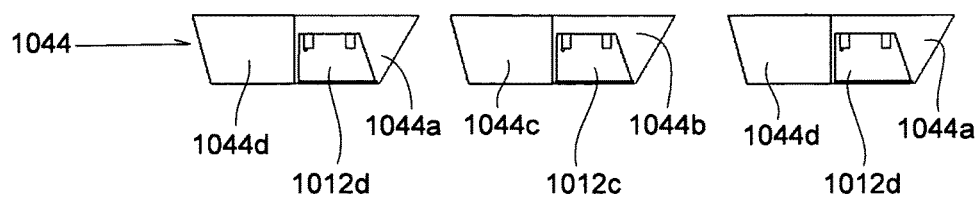
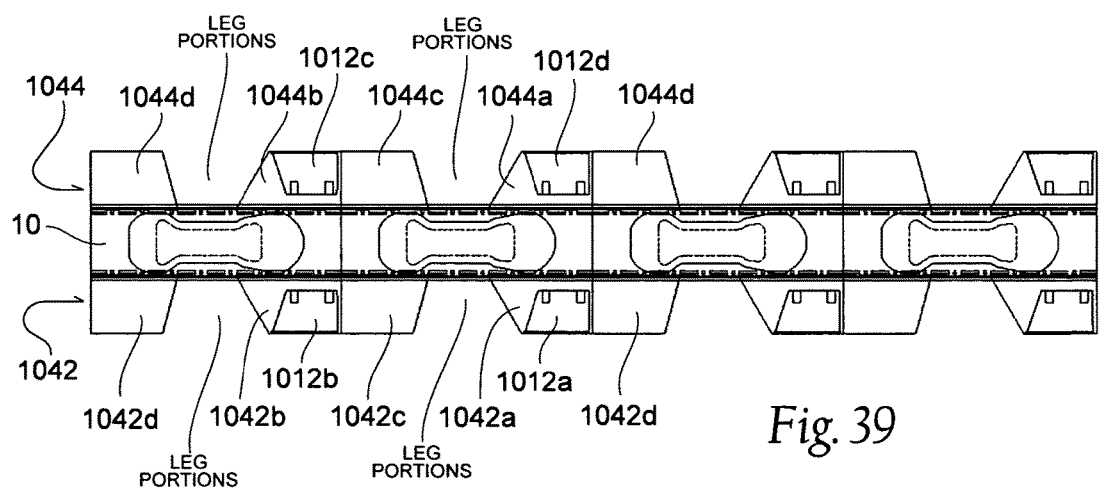
Fig. 39
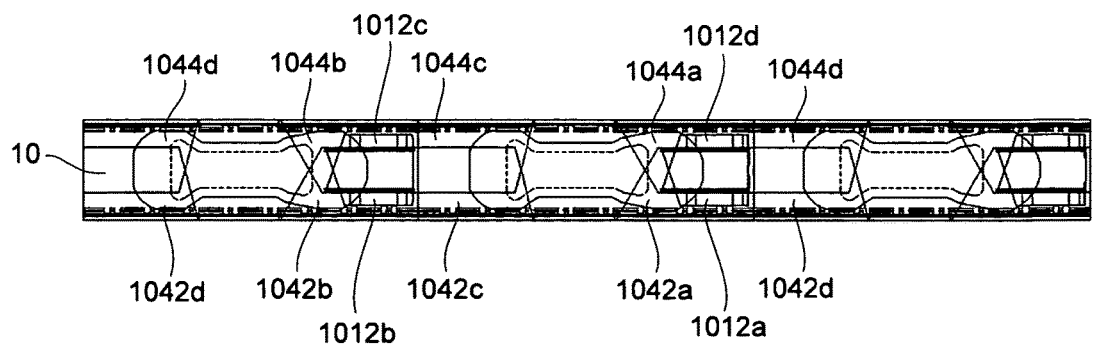
Fig. 40

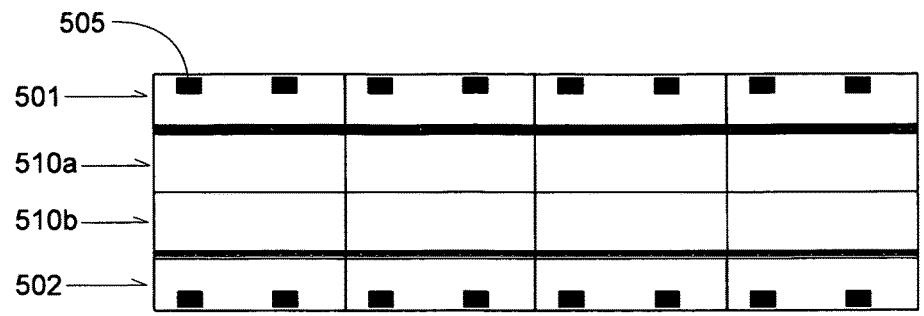
Fig. 45
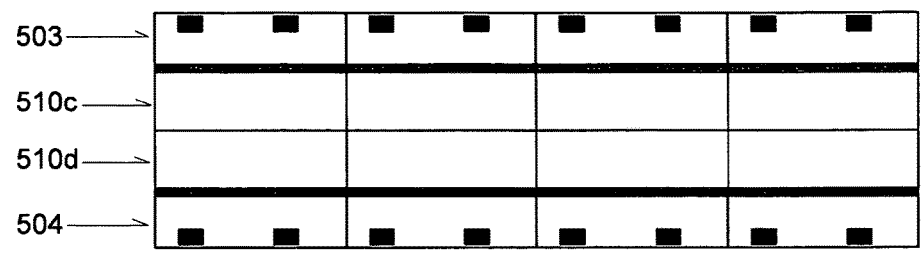
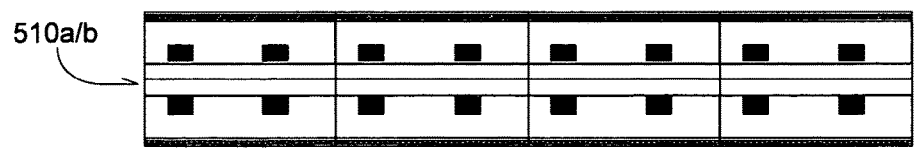
Fig. 46
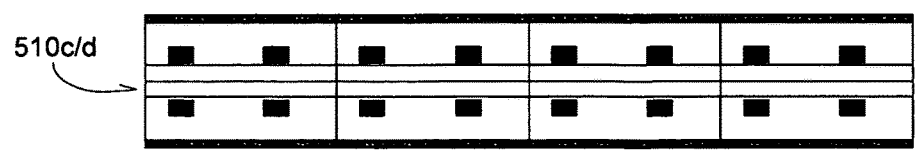

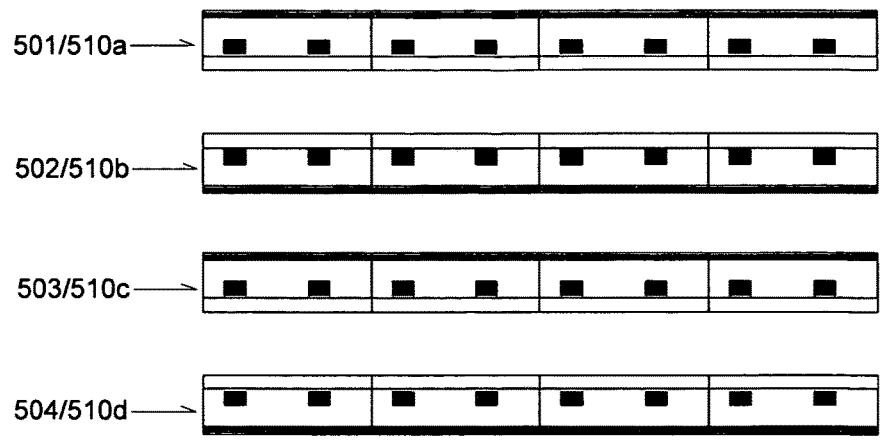
Fig. 47
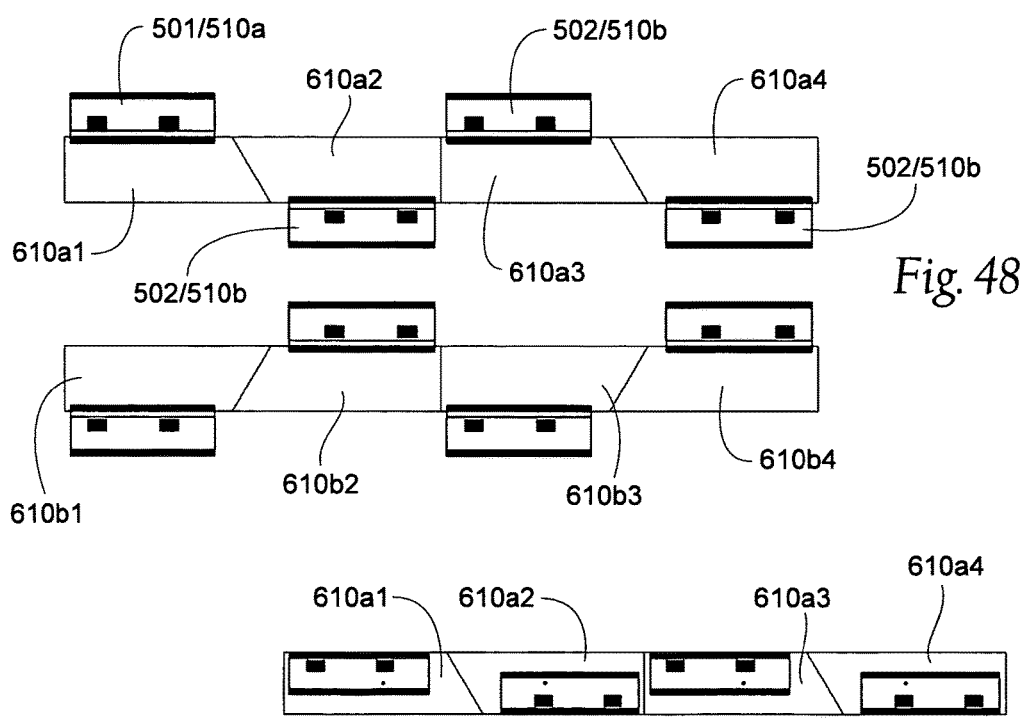
Fig. 48
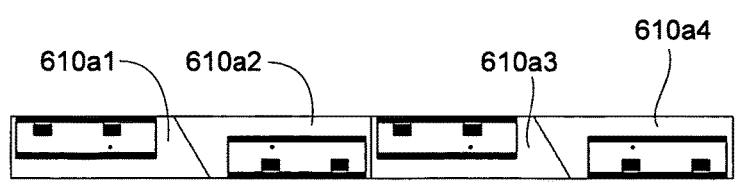
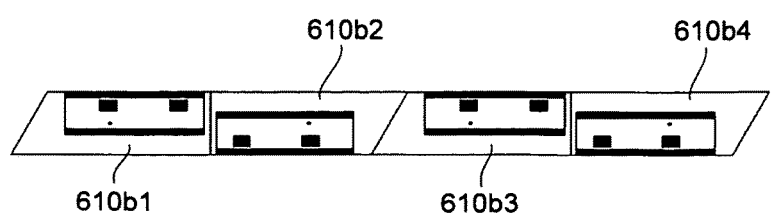
Fig. 49

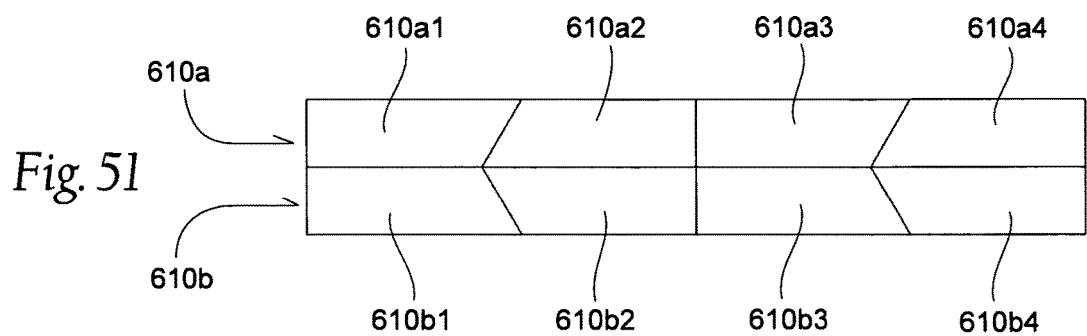
*Fig. 51*
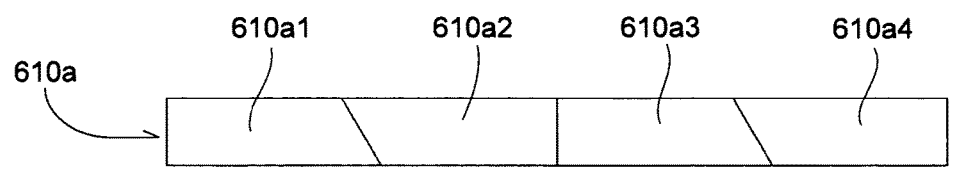
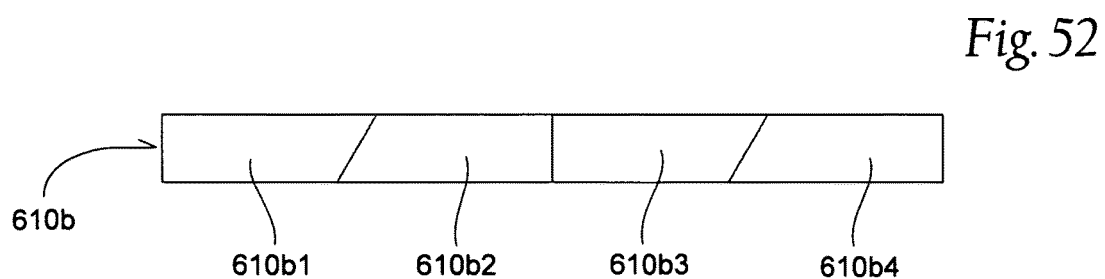
*Fig. 52*

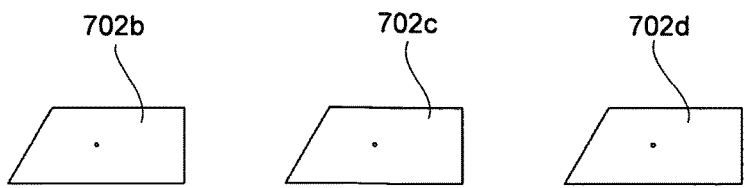
*Fig. 56*
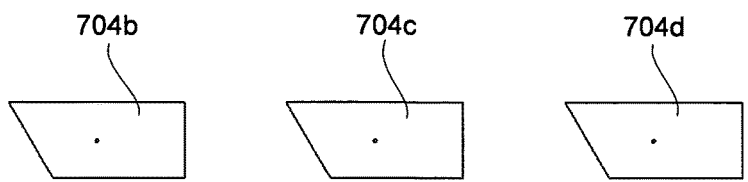
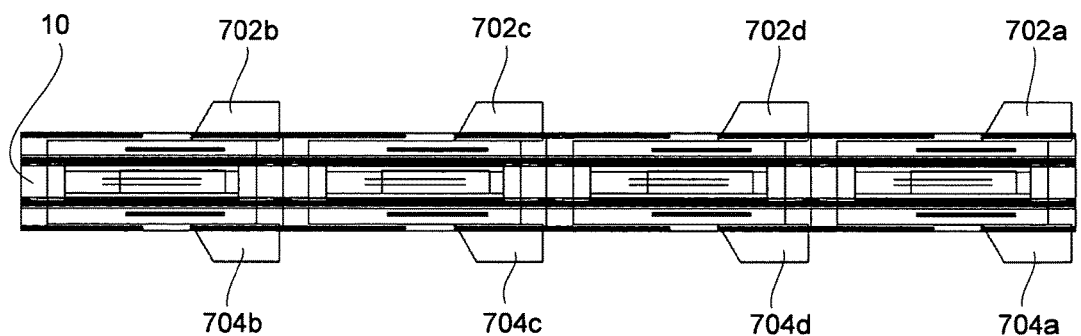
*Fig. 57*
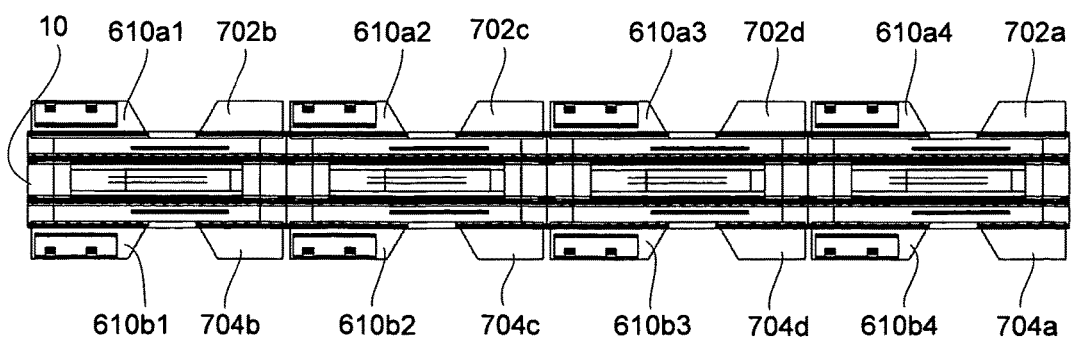
*Fig. 58*

METHODS AND APPARATUS FOR APPLICATION OF NESTED ZERO WASTE EAR TO TRAVELING WEB

RELATED APPLICATION

This application is a continuation-in-part of U.S. application Ser. No. 12/798,520 filed on 5 Apr. 2010, now U.S. Pat. No. 8,172,977, issued 8 May 2012, which in turn claims the benefit of U.S. Provisional Application Ser. No. 61/212,011 filed on 6 Apr. 2009, and U.S. Provisional Application Ser. No. 61/212,619 filed on 14 Apr. 2009.

BACKGROUND OF THE INVENTION

The present invention relates to disposable hygiene products and more specifically, to methods and apparatuses for processing disposable hygiene products. More specifically, the invention relates to cutting and applying segments of one web to attach to a disposable diaper.

The invention disclosed herein also relates to apparatus and methods for waste reduction. Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, non-woven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, it is beneficial to use up all of incoming rolls, so that a portion of the incoming rolls do not become waste. That objective is accomplished with the present invention When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

SUMMARY OF THE INVENTION

The present invention allows for square, and non-square, and preferably trapezoidal, ear webs to be applied to a traveling web, with zero or minimized waste present in the incoming ear web. Zero material is wasted due to the geometry of the chosen ear pattern and its downstream processing.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

The present invention provides a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

The present invention also allows for two side panel assemblies, including fastening mechanisms, to be attached to two ears, the side panel assemblies attached in a pre-folded condition. Two more ears can coupled to a chassis web to create a front panel to wear about the waist of a user.

The present invention also allows for chips of material to be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

BRIEF DESCRIPTION OF THE DRAWINGS

FIG. 8 is a perspective schematic view of the nested zero waste back ear applicator device and methods of the present invention;

FIG. 8a is a perspective schematic view of the nested zero waste back ear applicator device and methods of the present invention with an alternate web path configuration;

FIGS. 18-28 are schematic and plan views of methods of performing nested zero waste back ear application including a multi-component ear portion.

FIG. 18 is a plan view of an ear tab forming material (or wing, nonwoven web);

FIG. 19 is a plan view of an ear tab forming material following slitting and spreading;

FIG. 20 is a plan view of a side-panel assembly coupled to the ear tab forming material;

FIG. 21 is a plan view of the side-panel assembly coupled to the ear tab forming material, after the side-panel assembly has been folded;

FIGS. 22 and 23 are a plan view of the side-panel assembly coupled to the ear tab forming material, after the side-panel assembly has been folded, and during and after re-phasing of the side panel and wing assembly;

FIG. 24 is a plan view of the side panel and wing assembly being die cut, re-pitched, and rotated;

FIG. 25 is a plan view of the side panel and wing assembly following cutting, re-pitching and rotation;

FIG. 26 is a plan view of the side panel and wing assembly being coupled to a chassis assembly;

FIG. 27 is a plan view of the side panel and wing assembly, coupled to the chassis assembly, and folded into the profile of the chassis assembly;

FIG. 28 is an in-use plan view of an inventive disposable product formed by the methods of the present invention.

FIGS. 29-42 are schematic and plan views of methods of assembling a disposable product, including forming a nested zero waste ear to a nested zero waste wing portion, attaching ear and wing portions to a chassis top sheet, and folding the product to form a folded diaper.

FIG. 29 is a plan view of an ear tab forming material (or wing, nonwoven web);

FIG. 30 is a plan view of an ear tab forming material following slitting and spreading;

FIGS. 30-32 are a schematic view of formation of an ear assembly being slit, spread, tapes added, and the ear cut, repitched and rotated;

FIGS. 33-34 shown formation of a slit and spread wing web;

FIG. 35 shows the ear bonded to the wing web;

FIG. 36 shows the ear being folded down and temporarily coupled to the wing;

FIGS. 37-38 shown die cutting, repitching and rotating the wing assembly while carrying the ear assembly;

FIG. 39 is a plan view of the side panel and wing assembly being coupled to a chassis assembly;

FIG. 40 is a plan view of the side panel and wing assembly, coupled to the chassis assembly, and folded into the profile of the chassis assembly;

FIG. 41 is an in-use plan view of an inventive disposable product formed by the methods of the present invention;

FIG. 42 is a cross section view of an inventive disposable product formed by the methods of the present invention;

FIGS. 43-60 are schematic and plan views of methods of assembling a disposable product;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
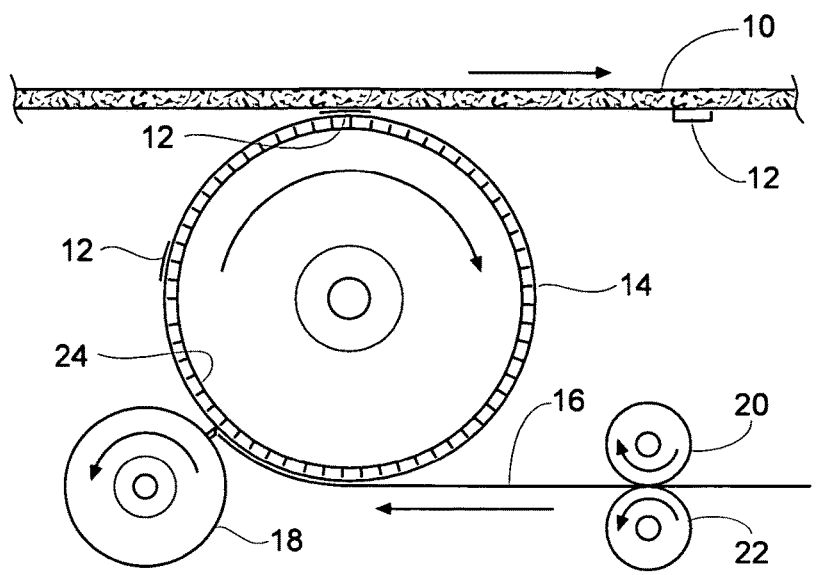
FIG. 1 is a diagrammatic side view of a Prior Art process.
Figure 2:
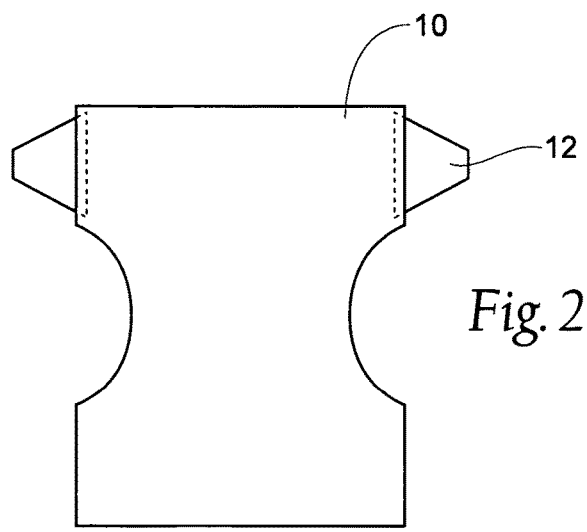
FIG. 2 is a top view of a disposable diaper product carrying a pair of ears.

Referring to the drawings there is seen in FIG. 1 a diagrammatic illustration of a prior art process for applying tabs to webs in a diaper making process, to result in an intermediate product shown in FIG. 2. The present invention can use this prior art method of affixing the segments 12 to the web 10, with a different anvil, the new anvil 114 described below. Web 10 is a composite material used in formation of diapers which is generally formed of various layers of material such as plastic back sheets, absorbent pads and nonwoven top sheets. A series of ears 12 are applied to web 10. In the illustrated process of FIG. 1, a rotatable vacuum anvil 14 is used to supply the ears 12 to web 10. Anvil 14 has internally reduced air pressure or vacuum (not shown), and a plurality of openings 24 are provided through its surface to enable suction of the tab segments 12 against the anvil surface 14. A web of the ear tab forming material 16 is fed by rollers 20 and 22 against the anvil surface 14 where it is cut into segments by a rotary knife 18.

The surface of the anvil roll 14 can have vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

It can be seen from FIG. 1 that in the prior art, the infeed of the ear tab forming material 16 can be at a first speed (with individual ears 12 spaced together), after which the individual ears gain speed to the speed of the anvil 14. Typical infeed speeds could be 120 mm/product for the infeed, while anvil speeds could be 450 mm/product on the anvil. This transition from the slower first speed to the quicker second speed takes place at the cut point, the ear tab forming material 16 slipping on the anvil 14 until cut. However, immediately at the transition cut point 18 from the slower speed to the faster speed, it is desired to place vacuum on the ears because centrifugal force would try to throw the ears off of the vacuum anvil 14.

Ear webs 16 can be comprised of two portions, 12a and 12b, as shown in FIG. 2. Segment 12a is more specifically referred to as the tab section of the ear 12, segment 12b is the ribbon section of the ear 12.

Figure 3:
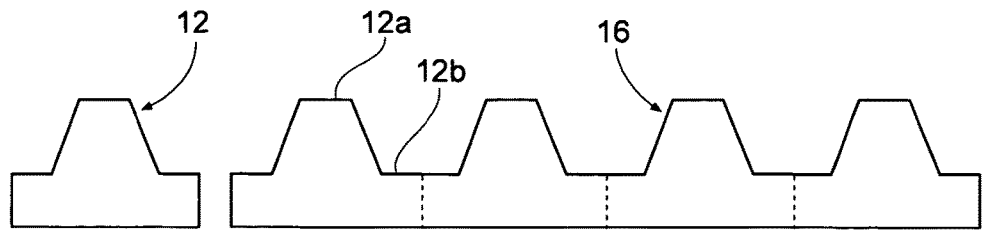
FIG. 3 is a top view of an ear forming web including an individual ear detached from the web.
Figure 6:
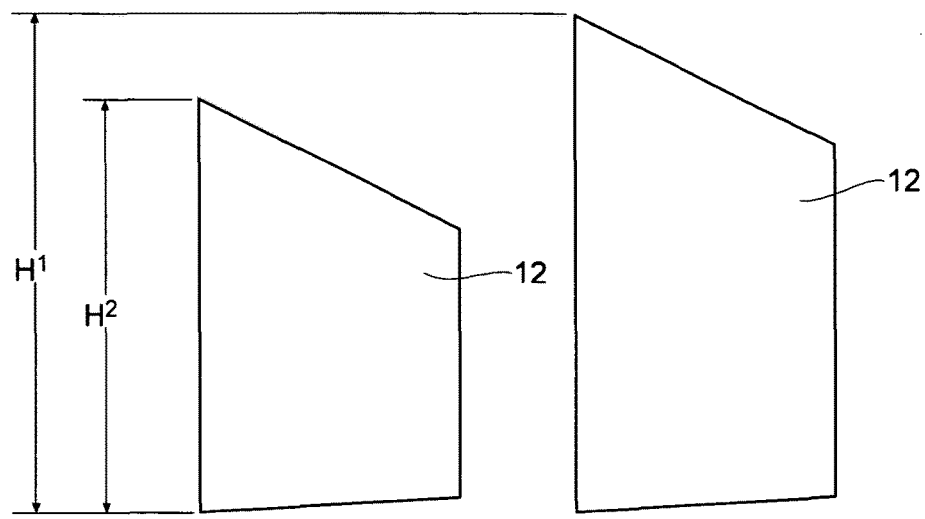
FIG. 6 shows an alternate ear pattern and alternate ear sizes.
Figures 7A, 7B:
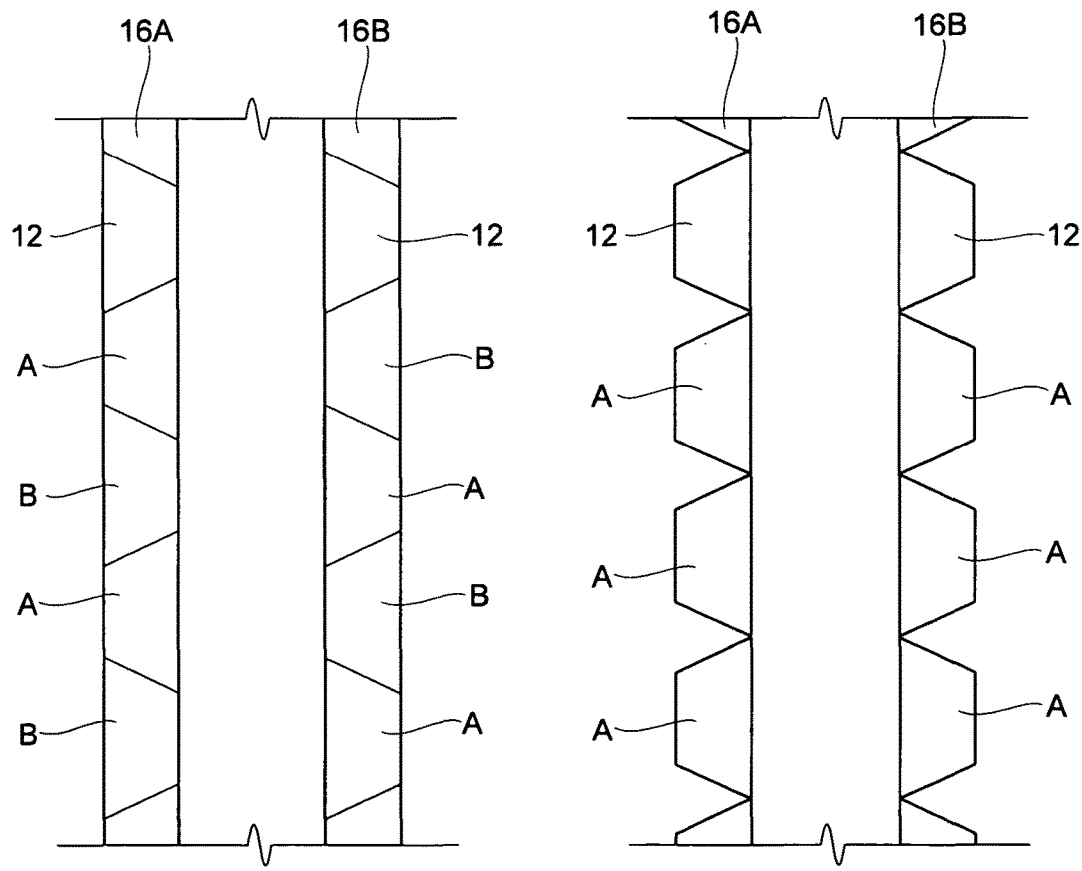
FIGS. 7A, 7B, 7C, 7D, 7E, and 7F are top views of ear webs, FIG. 7A showing non-rotated alternating die cut ear webs, and FIG. 7B showing alternating rotated die cut ear webs, and FIGS. 7C, 7D, 7E, and 7F showing alternate ear configurations.

Alternatively, the ears can comprise a trapezoidal shape, as shown in FIGS. 6, 7A and 7B, which will be described later. The trapezoidal shape of FIGS. 7A and 7B is particularly advantageous for zero waste applications, where it is desired to reduce or eliminate the scrapping of raw material. In another zero waste technique, two parallel series of alternating ear webs 16 with ribbon sections of the ear 12 could be created by mirroring the web 16 as shown in FIG. 3 and placing the mirrored web down one/half of an ear length (not shown).

Figure 4:
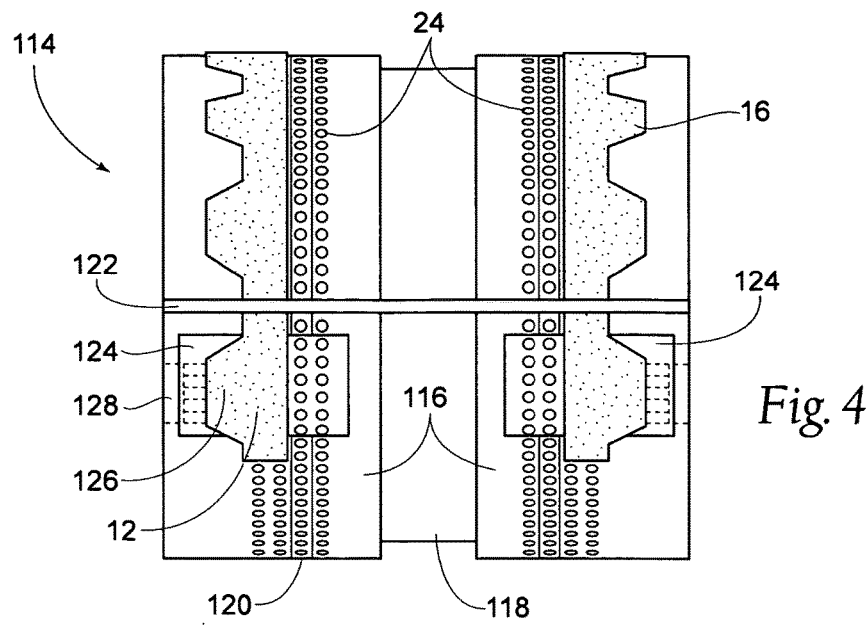
FIG. 4 is a front view of an anvil roll carrying two ear webs.

Referring now to FIG. 4, a front view of an anvil roll 114 is shown carrying ear forming material 16 (and later, individual ears 12) in phantom. The anvil roll 114 is preferably formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

Still referring to FIG. 4, two diametrically opposed anvil pockets 122 and two diametrically opposed pairs of ear retaining portions 124 are shown. The ear retaining portions can be created as inserts, with different vacuum patterns applied as the user deems necessary. Each anvil pocket 122 is a groove which extends across the face of the entire anvil roll 114. One ear retaining portion 124 is located on each of the vacuum portions 116. Each ear retaining portion 124 has an ear vacuum hole pattern 126 made of a plurality of vacuum holes 24 located at or near the surface of the anvil roll 144. A plurality of rows of vacuum holes 24 can be employed, each row having a plurality of vacuum holes 24, although more or less than those configurations or patterns shown can be used.

Figure 5:
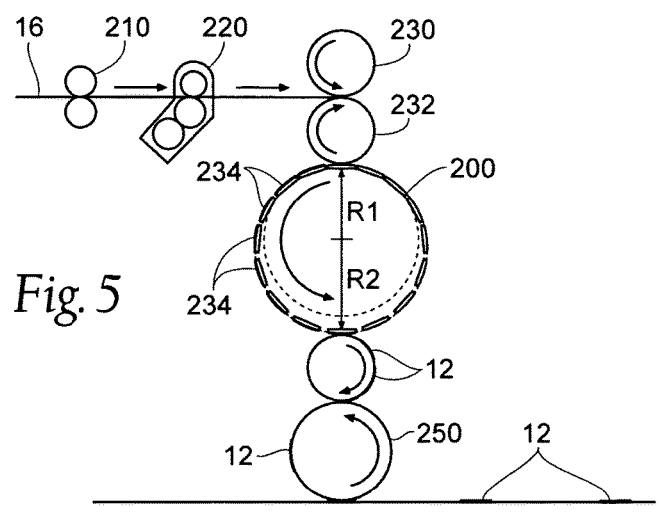
FIG. 5 is a schematic view of a nested zero waste back ear applicator device and methods of the present invention.

Referring now to FIG. 5, a schematic view of a nested zero waste ear applicator device and methods of the present invention are shown. Components of this ear applicator include a web slitter 210, which processes incoming ear web material 16 into two parallel paths (not shown from this view). After being slit, ear web material is processed by tape applicator 220, which can add tape to the ears for securing the ears 12 about the waist of a wearer.

After slitting and application of the tape to the ear web 16, an ear die is used to cut the ear web 16 into the pattern shown in FIG. 7A. The ear material 16 is die cut with a nested pattern on a synchronized vacuum anvil/die combination 230/232 and carried by rotation or otherwise to an ear turner assembly 200.

Referring still to FIG. 5, the cutting edges of the ear dies 230 turn against and in coordination with a corresponding anvil 232 to create preferably trapezoidal ears. It is noted that as shown in FIG. 6, ears 12 having different heights, H1 and H2, can be produced in this configuration by speeding up or slowing down the infeed rate of material 16 into the anvil/die combination 230/232. In this manner, more or less slip is allowed on material 16 prior to cutting, resulting in longer or shorter ears.

Figure 5A:
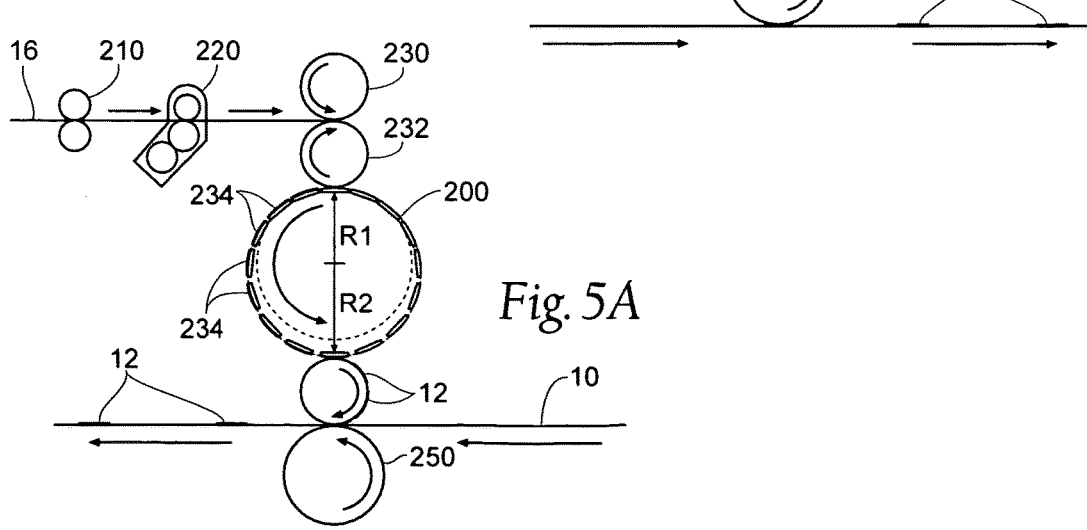
FIG. 5a is a schematic view of a nested zero waste back ear applicator device and methods of the present invention, with an alternate web path configuration.

Because the ear material 16 has already been slit into two lanes, one for a left side of a diaper and the other for a right side of a diaper, it is noted that two parallel ear dies 230 are used to produce the pattern shown in FIG. 7A to the slit web 16, but because of the side vantage point of FIG. 5a only one of the lanes is visible if more than one is desired.

The resulting discrete ear pieces however, due to the trapezoidal pattern of the ears shown in FIG. 7A, alternate between a correct orientation A and an incorrect (reversed) orientation B. The reversed ears B are required to be rotated 180° into the correct orientation A such that the ears and associated tape present a left ear and a right ear on the diaper, such as that shown on FIG. 7B. In correct orientation A, such as shown in FIG. 7B, the shorter of the parallel edges of the trapezoid will face toward an outside, left for the left side, and right for the right side. This geometry is desirable to accommodate the legs of the wearer when the ears 12 are pulled about the waist of the wearer.

To accomplish the reversal of the ear pattern, discrete ear pieces are picked up at the nested ear pitch by an ear turner assembly 200 (see FIGS. 5 and 8) that has a series of pucks 234 that travel radially from a minimal radius R1 (and therefore a minimal tangential speed) to a maximal radius R2 (and therefore a maximal tangential speed) at a depositional site. The difference between R1 and R2 is such that individual pucks 235 can be unnested and allow clearance (in the radial direction from adjacent pucks 234) for every other ear to be rotated, as will be described later in relation to FIGS. 10a and 10b. The rotated ears are then unnested and into the correct orientation and brought to the proper speed for deposition onto either an additional vacuum drum (as shown on FIG. 5a) and subsequently onto web 10 or high vacuum drum 250.

Referring to FIG. 7A, two lanes of ears 12 are depicted, 16A and 16B representing right and left ears intended for a product. The longest side of the ears 12 is intended for attachment to web 10, so because trapezoids are desirable, every other trapezoid in each lane will require 180° rotation to allow the desired side (for example, the longest side) of the ear 12 to be confronted with attachment to web 10. All of the "B" labeled ears 12 on supply 16A will be rotated 180° into an A position. All of the "B" labeled ears 12 on supply 16B will be rotated 180° into an A orientation position to achieve the desired depositional orientation shown in FIG. 7B.

Figure 7C:
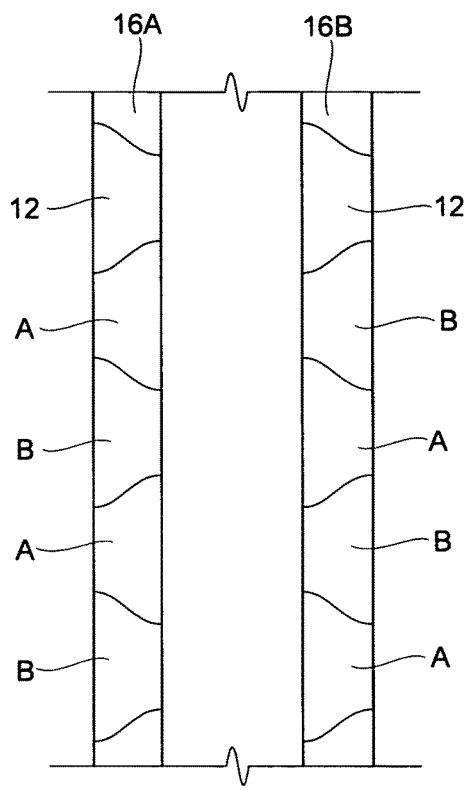
Figure 7D:
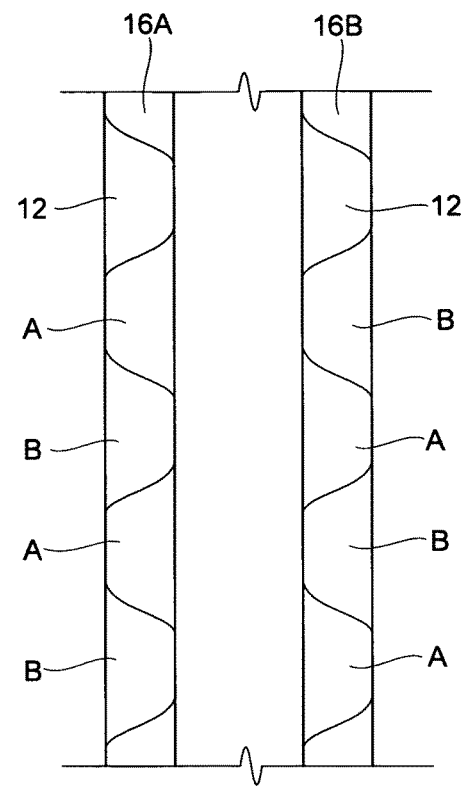
Figure 7E:
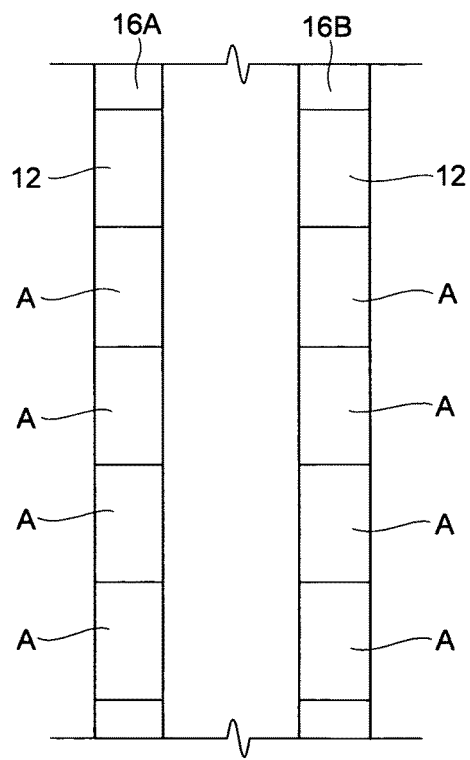
Figure 7F:
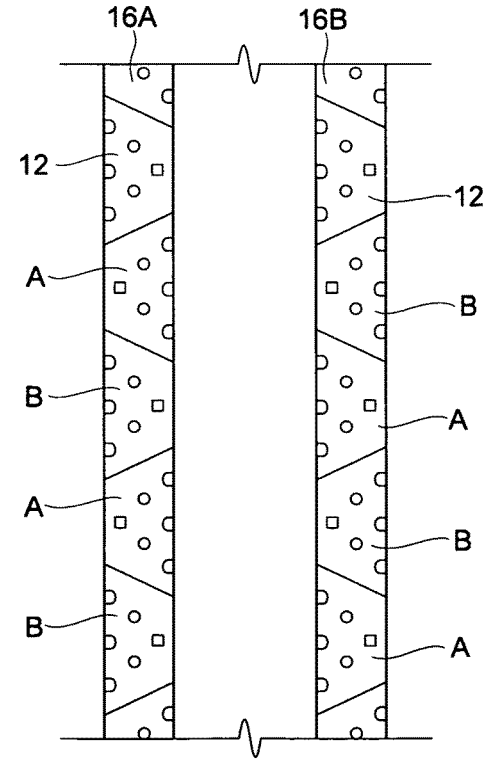

It is noted that ear configurations can vary as shown in FIGS. 7C-7F. In FIGS. 7C and 7D, wavy or curved ear patterns are shown. In FIG. 7E, a square pattern is shown. In FIG. 7F, a trapezoidal pattern is shown. Chips may be cut out in any shape of ear patterns, such as such in FIG. 7F. The chips can be of any shape or size, and can be positioned either on edges of the ears or on the interior of the ears.

Referring now back to FIG. 5, following rotation of every "B" labeled ear 12, each ear is deposited onto vacuum drum 240, rotated and picked up by high vacuum drum 250. Vacuum drum 240 is a size change roll that matches pitch. Vacuum drum 240 can also be used as a roller, in conjunction with or replacing roller 260, FIG. 16.

Because the ears 12 need to be sped up to match the speed of chassis web 10, the rotation of high vacuum drum 250 is quicker than that of vacuum drum 240. The higher vacuum in drum 250 relative to drum 240 allows the ears 12 to be snatched or grabbed at the higher rotational speed present in drum 250.

Referring now to FIG. 5a, a schematic view of a nested zero waste back ear applicator device and methods of the present invention is shown, with an alternate web path configuration.

Referring now to FIG. 8, a perspective schematic view of the nested zero waste back ear applicator device and methods of the present invention is shown. As can be seen, two ear turner assemblies 200R (right) and 200L (left) are provided, to rotate every other ear 12 applied to the right side of the chassis web 10, and every other ear 12 applied to the left side of the chassis web 10. In this manner, for a single product, one of the two ears will have been rotated 180°.

As can be seen from FIG. 8, two types of pucks are provided, non-rotating pucks 234A and rotating pucks 234B. The non-rotating pucks 234A carry the "A" ears shown in FIG. 7A, or the ones that do not require rotation. The rotating pucks 234B carry the "B" ears shown in FIG. 7A. As the ear turner assemblies 200R and 200L go through their rotation, ears 12 are picked up from the ear die/anvil station 230/232 and rotate about the rotator 200, while every rotating puck 234B also rotates radially during rotation of the rotator 200, as will be described later.

The ears 12 are then deposited onto chassis web 10 and bonded thereto, for instance by ultrasonic bonding ring 252, where the resulting product is sent downstream for further processing.

Referring now to FIG. 8a, a perspective schematic view of the nested zero waste back ear applicator device and methods of the present invention with an alternate web path configuration is shown. This is the preferred embodiment of the vacuum drum/ultrasonic bonding ring 250/252 in relation to the vacuum drum 240. In this configuration, the ears are ultrasonically bonded to the chassis web 10 between the vacuum drum/ultrasonic bonding ring 250/252 and the vacuum drum 240 as the chassis web 10 travels from right to left as pictured.

Figures 9, 10A, 10B:
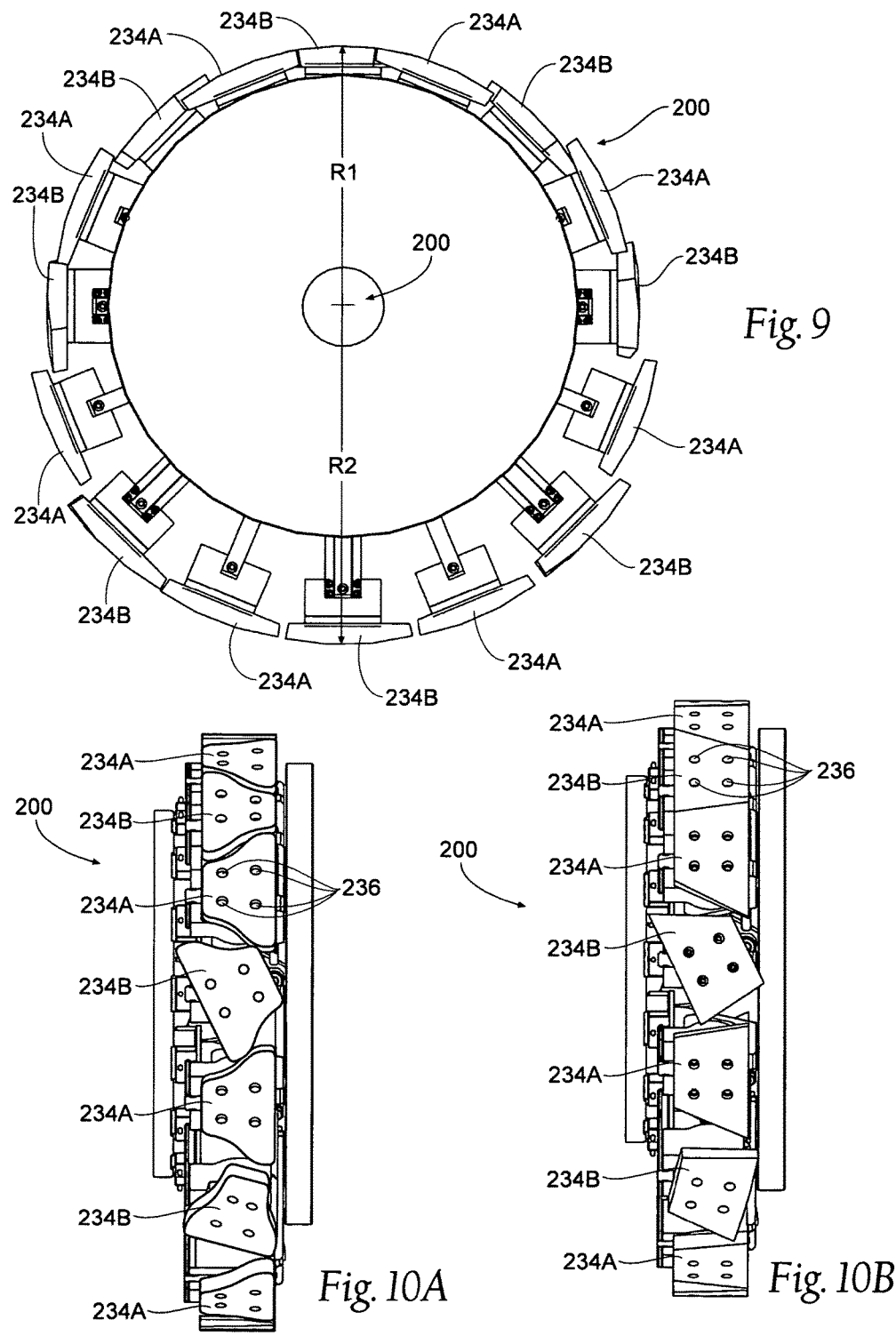
FIG. 9 is a side view of an ear turner assembly device used to rotate alternating ears.
FIG. 10a is front view of the ear turner assembly device used to rotate alternating ears.
FIG. 10b is front view of the ear turner assembly device used to rotate alternating ears, showing an alternate embodiment of a puck, configured to match in shape and size alternate ear design.

Referring now to FIG. 9 a side view of the ear turner assembly device 200 is shown. The ear turner assembly device 200 used to rotate alternating ears, again with the entire device 200, rotating about a central axis, and each puck 234 traveling radially from a minimal radius R1 to a maximal radius R2 at a depositional site during rotation, and then back to the minimal radius R1. The difference between R1 and R2 is such that individual pucks 235 can be unnested and allow clearance for every other ear to be rotated. Comparing the During rotation from the R1 to the R2 position, rotating pucks 234B undergo not only the increase in radius, but also undergo 180° rotation about an axis perpendicular to the central axis. This can be performed preferably with a screw operation (reference letter S, FIG. 12). During rotation from the R2 position back to the R1 position, the rotating pucks 234B rotate back through their 180° rotation to get to their initial position by use of a yankee screw, which is capable of both advancing and retracting the pucks 234B, and rotating the pucks 234B, upon driving the shaft of the yankee screw inward and outward radially.

Referring now to FIG. 10a, a front view of the ear turner assembly device 200 used to rotate alternating ears is shown. As can be seen, the pucks 234 are each equipped with vacuum voids 236 through which a vacuum is pulled, retaining ears on the rotator device 200 through their rotation (radially rotating for every ear, radially and axially rotating for every other ear) until deposition. As can be seen, the pucks 234 are can be roughly trapezoidal in shape to roughly match the shape of the ears 12. It is also seen from this view that the non-rotating pucks 234A remain in their axial non-rotated position relative to the rotating pucks 234B, which rotate from their initial position nested between two non-rotating pucks 234A, and back.

Referring now to FIG. 10B, an alternate shape of the pucks 234 is shown. In FIG. 10A, the pucks 234 are configured to receive wavy shaped ears as described earlier. In FIG. 10B, the pucks 234 are configured to receive trapezoidal shaped ears as described earlier. It is preferable to configure the pucks 234 to match the desired ear pattern.

Figure 11:
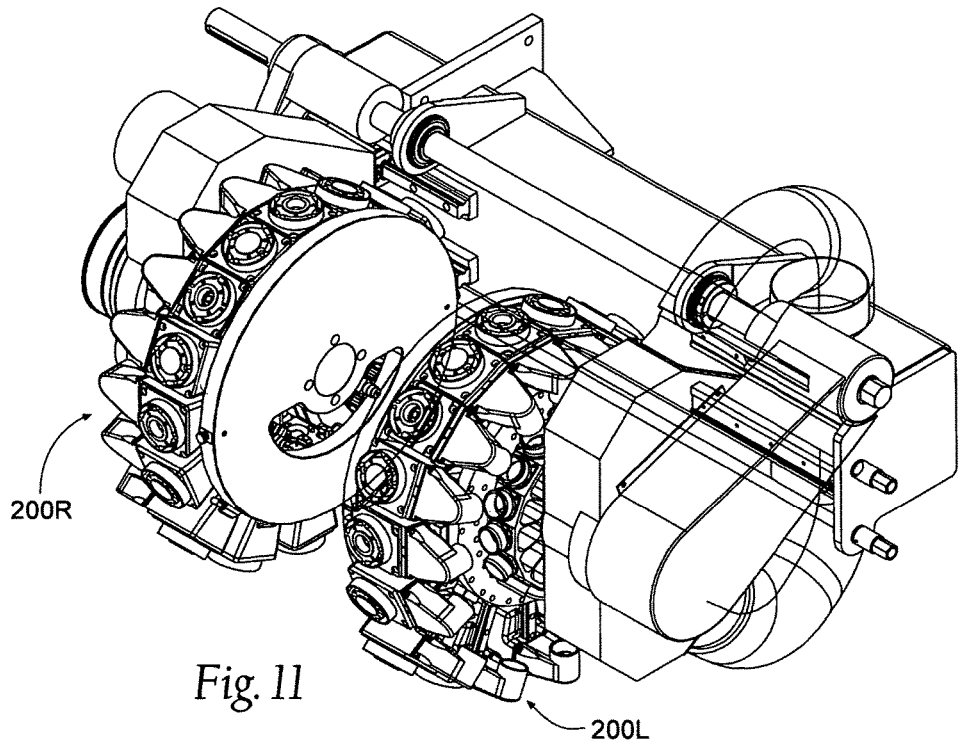
FIG. 11 is a perspective view of two ear turner assembly devices used to rotate alternating ears on a left and a right ear web.
Figure 13:
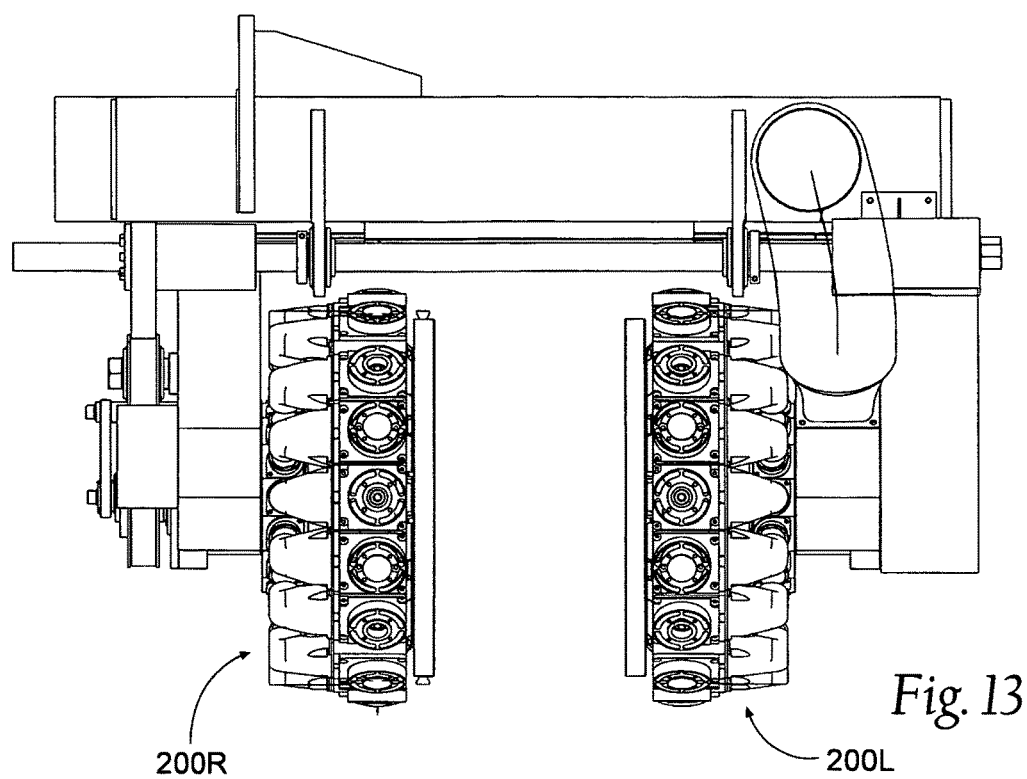
FIG. 13 is a front view two ear turner assembly devices used to rotate alternating ears on a left and a right ear web.
Figure 14:
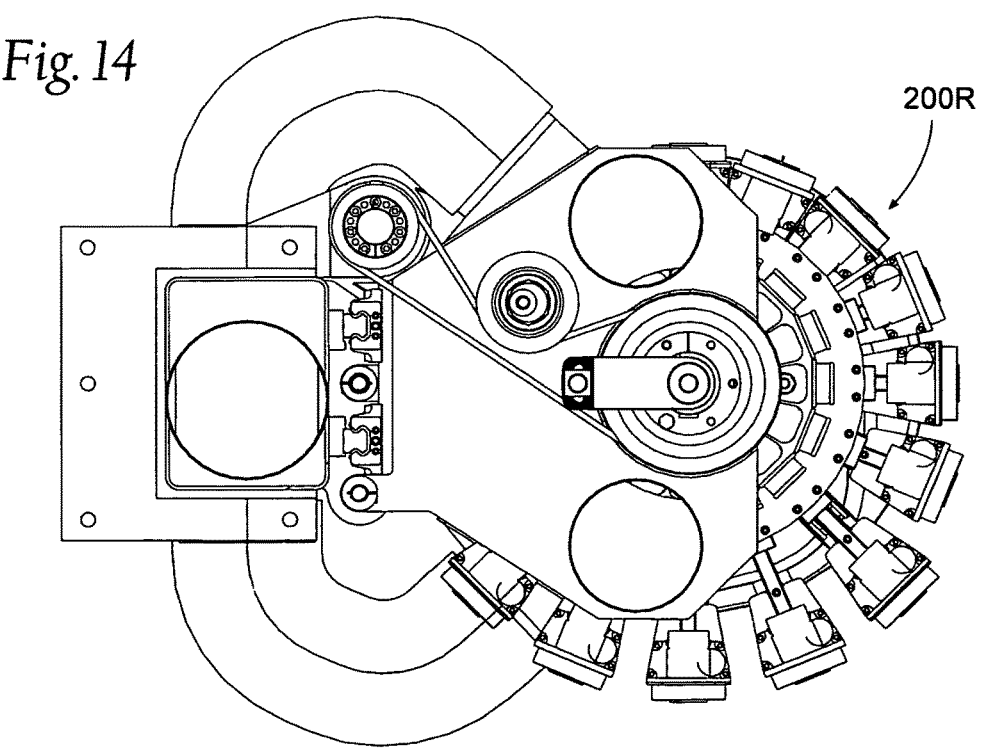
FIG. 14 is a side view of an ear turner assembly device used to rotate alternating ears.

Referring now to FIG. 11, a perspective view of the two ear turner assembly devices 200R and 200L are shown. Also shown are vacuum manifolds used to apply the vacuum to the pucks 234. In this sense, the rotation of the pucks 234 is described in currently pending U.S. application Ser. No. 11/244,387, which is incorporated herein by reference. A front view of this configuration is shown in FIG. 13 and a side view in FIG. 14.

Figure 12:
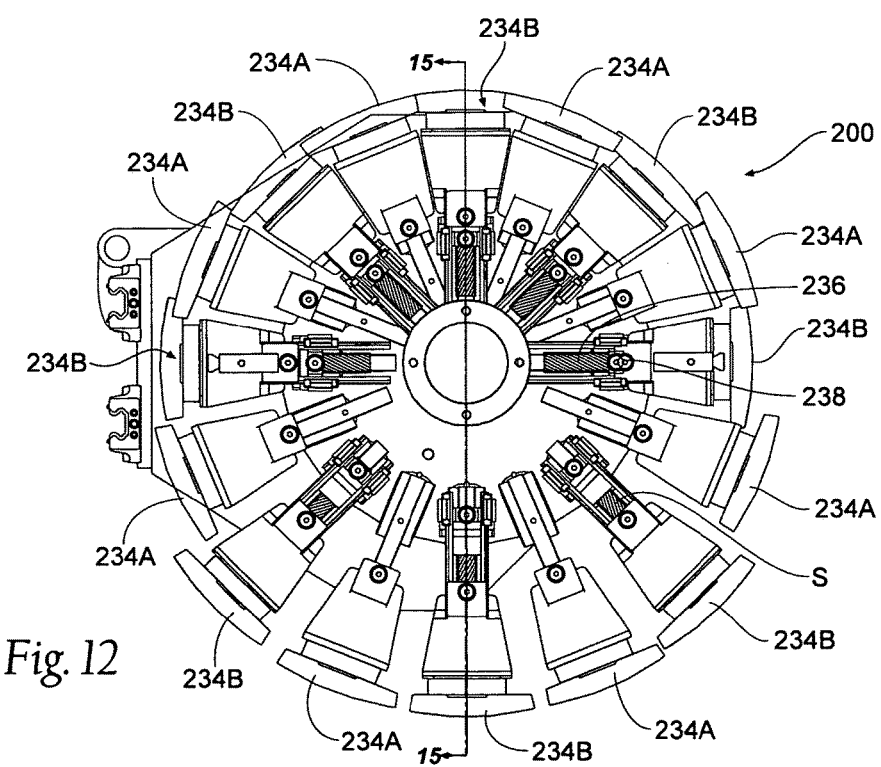
FIG. 12 is a side view of an ear turner assembly device used to rotate alternating ears.

Referring now to FIG. 12 a mechanism for rotating pucks 234b is shown. There, it is seen that screws 236 are provided such that movement of the pucks 234B away from the center axis simultaneously causes rotation of puck 234B. A radially traveling coupling 238 couples the puck with the screw 236, and when the threads of the screw are engaged with the radially traveling coupling 238, rotation is caused.

Figure 15:
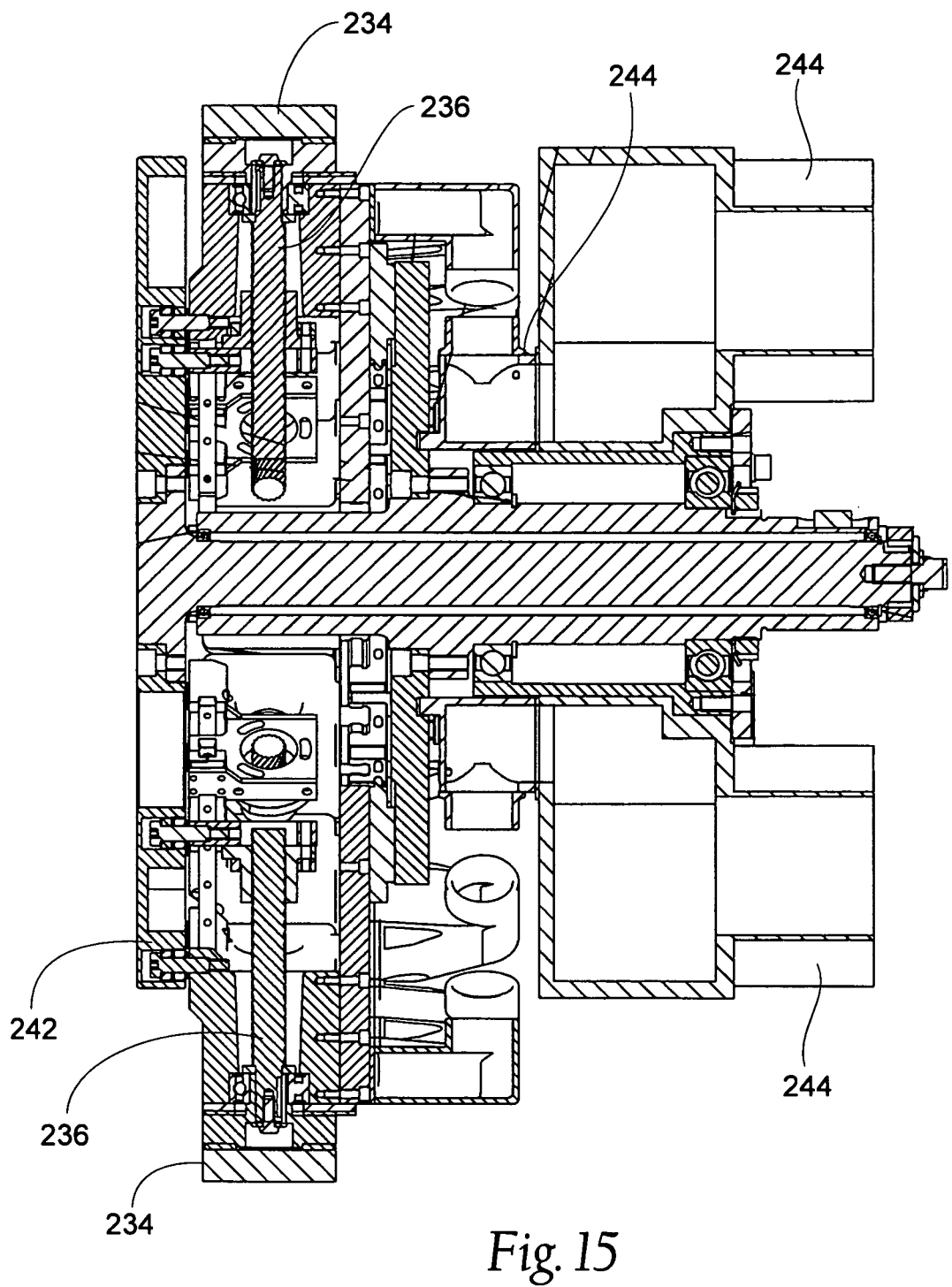
FIG. 15 is a sectional view of the ear turner assembly device used to rotate alternating ears shown in FIG. 10.

FIG. 15 is a cross-sectional view of the ear turner assembly device 200 used to rotate alternating ears along the line shown in FIG. 12. Particularly, screws 236 are operably coupled with pucks or rotator assemblies 234. By rotation of the screw 236, pucks 234 are moved along a radial line in relation to shaft turner 246. Vacuum manifold 244 is provided to commute vacuum to the pucks 234 and ultimately to hold the ears 12 in place. Ear turner cam 242 is provided for rotative purposes.

Figure 16:
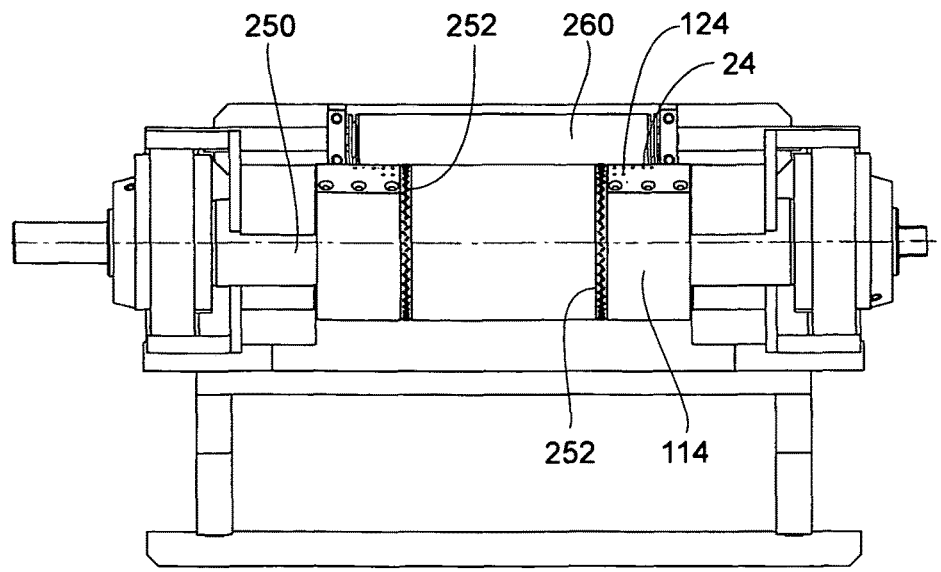
FIG. 16 is a front view of an anvil, ultrasonic bonding ring, and vacuum pattern used for pitch changing ears from a slower web and applying and bonding the ears to a faster moving chassis web.

Referring now to FIG. 16, a front view of a rotatable vacuum wheel 114, ultrasonic bonding ring 252, and vacuum pattern 124 used for pitch changing ears from a slower web and applying and bonding the ears 12 sandwiched between roller 260 and the anvil 114 to a faster moving chassis web is shown.

In this embodiment, the aggressive vacuum pattern 124 on high vacuum drum 250 will have withdrawn ears 12 from vacuum drum 240. This step follows the rotation of the "B" ears as described above. The chassis web 10 is fed in between the roller 260 and the high vacuum drum 250. The ultrasonic bonding ring 252 couples the ears 12 with the chassis web 10 (refer to FIG. 5).

Figure 17:
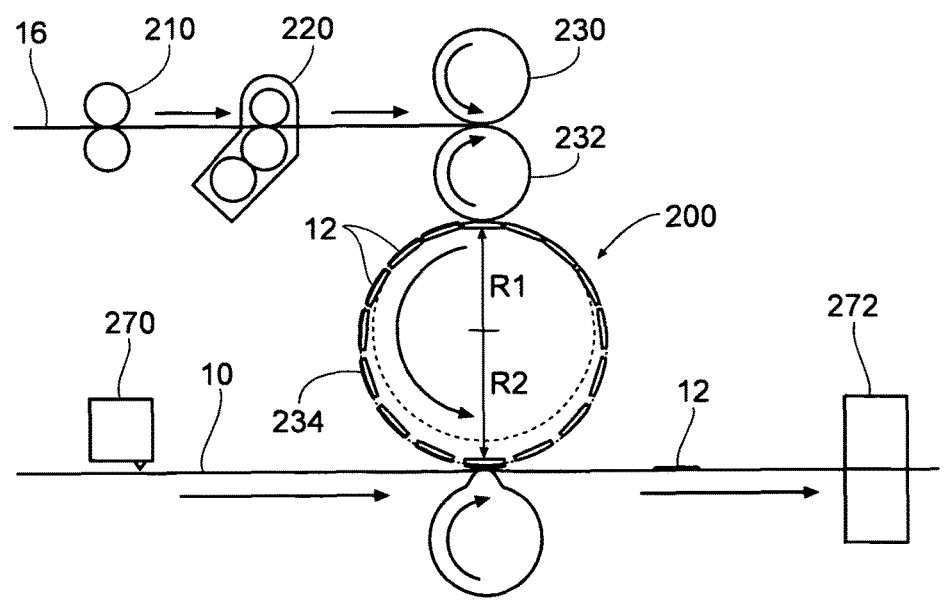
FIG. 17 is a schematic view of the nested zero waste back ear applicator device and methods of the present invention, shown with an alternate embodiment of a means for applying the ear to the chassis web.

Referring now to FIG. 17, a schematic view of the nested zero waste back ear applicator device 200 an alternate embodiment of a means for applying the ear 12 to the chassis web 10 is shown. Instead of the vacuum porting system as previously described, a protuberance carrying rotatable body 274 is urged against the chassis web 10, as disclosed in U.S. Pat. No. 6,475,325, which is incorporated herein as if fully set forth. The disclosure of U.S. Pat. No. 6,475,325 is referred to as the "bump transfer" method. In this embodiment intermittent adhesive is applied to the chassis web 10 at station 270. The intermittent adhesive is applied at intervals to make contact with ears 12 carried by rotating body 200. The protuberance carried by body 274 urges the chassis web 10 towards an ear 12 carried by a puck 234. With the ear 12 coupled with the chassis web, the coupled material is processed by final bonding station 272, after which the ear/chassis combination is sent downstream for further processing as desired.

Referring generally to FIGS. 18-28, schematic and plan views are presented of a novel disposable garment configuration using methods of performing nested zero waste back ear application including a multi-component ear portion fabrication, bonding and folding. The embodiments of FIGS. 18-28 are particularly well suited for formation of what is called in the industry as an adult-sized diaper.

One difficulty with adult-sized products is sheer size. The products are required to be quite large (for instance, 32" wide in a non-stretched condition) in the waist section to fit about the waist of an adult. However, the adult-sized products are typically shipped in packages about 8" wide, so the products require folding, particularly at the waist zone where the product is the widest, in order to be compactly packaged and shipped.

The prior art often employed a Z-fold of ears to get the waist band down to size. For instance, the ears 12 applied to web 10 shown in FIG. 2 would have to be folded as to not extend much past the profile of the chassis web 10. This assists both processing of the web as it avoids flying parts, but also assists packaging and transport of the material.

The embodiments of FIGS. 18-28 show construction of an ear segment that can be formed of multiple pieces, as opposed to the one piece ears of the prior art (see, e.g., ears 12 of FIG. 2). This allows both creation of a contoured multi-piece ear segment, as well as assembly of at least portions of the ear segment in a pre-folded condition.

Figure 18:
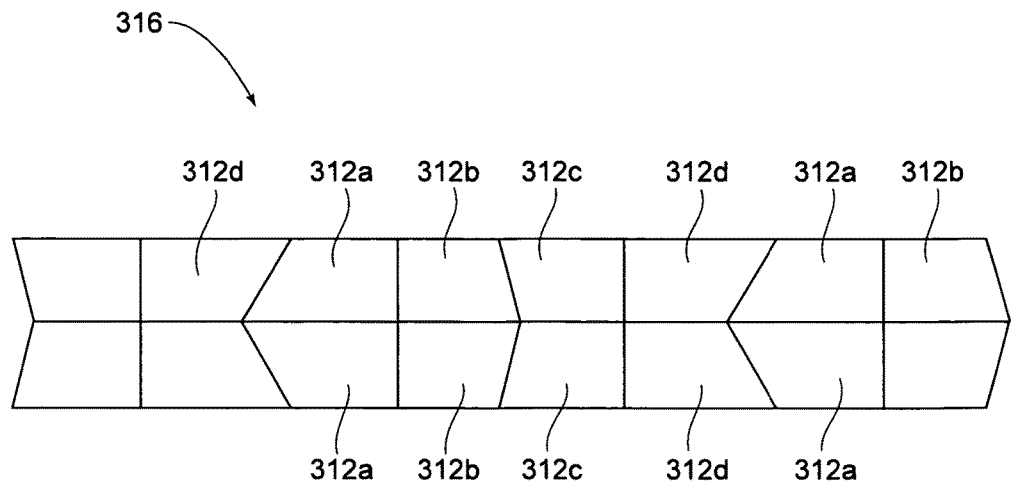

Referring now to FIG. 18, a plan view of an ear tab forming material 316 is shown entering the system similarly positioned to material 16 shown on FIG. 8 or 8a. Preferably the ear tab forming material (or wing) 116 is a non-woven continuous web of material which is ultimately formed into shaped ear portions 312. Shaped ear portions 312, as described with respect to FIGS. 7a-7f, can take on different shapes, and can have correct original orientation, or orientation that requires re-phasing or turning as described above.

In a preferred embodiment ear portions 312 of the present invention will have side panel assembly receiving ear portion configurations 312a and 312d, and non-receiving ear portion configurations 312b and 312c as will be described later.

Figure 19:
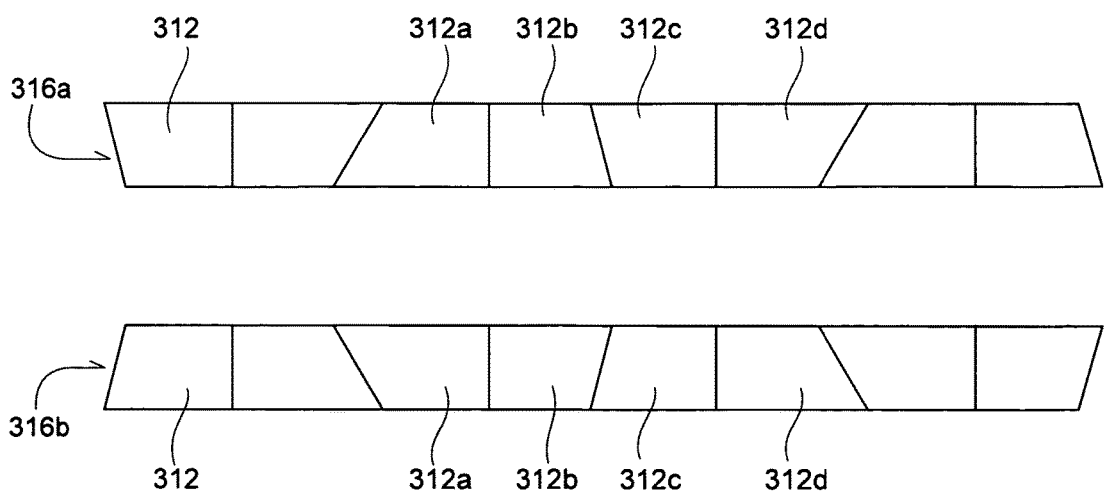

Referring to FIG. 19, the ear tab forming material 316 is slit and spread, for instance as shown on FIG. 8 at station 210. Lanes 316a and 316b of slit and spread ear tab forming material 316 receive the side panel assemblies described in FIG. 19a, and ultimately become left and right ear segments on a disposable product.

Figure 19A:
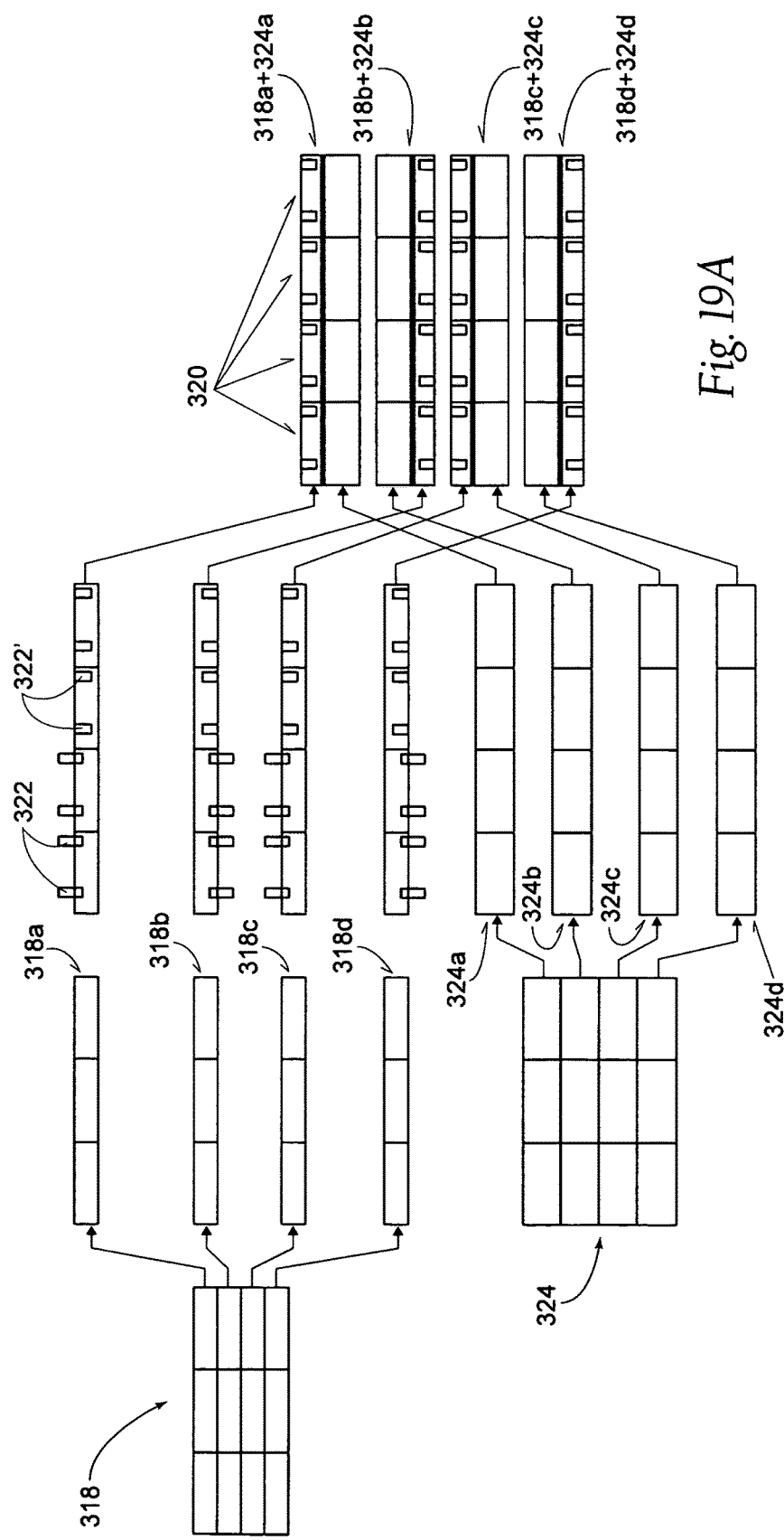
FIG. 19a is a schematic view of formation of a side panel assembly.

Referring now to FIG. 19a, a schematic view of formation of side panel assemblies 320 is shown. The formation of side panel assemblies 320 begins with an outer non-woven web material 318, which is slit and spread into discrete non-woven web portions 318a, 318b, 318c, and 318d, each of the non-woven web portions also preferably being cut in the cross-machine direction into the preferred size.

To each of the discrete non-woven web portions 318a, 318b, 318c, and 318d, one or more fastening mechanisms 322 are applied. Fastening mechanisms 322 can be tape tabs, covered tape tabs, strips of hook and loop material, continuous hook and loop material, patches of hook and loop material, etc. The fastening mechanisms 322 will be unfastened and refastened about the waist of the user to tighten the disposable garment about the waist.

Next, the non-woven webs 318 carrying fastening mechanisms 322 are folded over, creating a folded web 318 and folded fastening mechanisms 322'. This causes the combination of the non-woven web 318 and the fastening mechanisms 322 to be narrower than the discrete non-woven web portions 318a, 318b, 318c, and 318d. It is noted that the folded fastening mechanisms 322' of web portions 318a and 318b will have opposing fastening mechanisms 322' as they will become the right and left hip waist fastening mechanisms, respectively, once placed about the waist of a user (shown later in the process).

In addition to the discrete non-woven web portions 318a, 318b, 318c, and 318d, a stretch laminate web 324 is also provided. This too is slit and spread into discrete stretch laminate web portions 324a, 324b, 324c, and 324d.

Next, the non-woven web portions 318a, 318b, 318c, and 318d, including their respective fastening mechanisms 322', are bonded to stretch laminate web portions 324a, 324b, 324c, and 324d respectively, forming the side panel assemblies 320 in four different lanes, 318a+324a, 318b+324b, 318c+324c, and 318d+324d. The non-woven web portions 318a, 318b, 318c, and 318d can be bonded to the stretch laminate web portions 324a, 324b, 324c, and 324d in any fashion, such as by ultrasonic bonding using a mechanism such as shown in FIG. 16, by lap seams, by adhesives, fin seams, etc.

The stretch laminate portions 324a, 324b, 324c, and 324d can also be folded if desired, or the stretch laminate portions 324a, 324b, 324c, and 324d in combination with the non-woven web portions 318a, 318b, 318c, and 318d can all be folded together and again.

Figure 20:
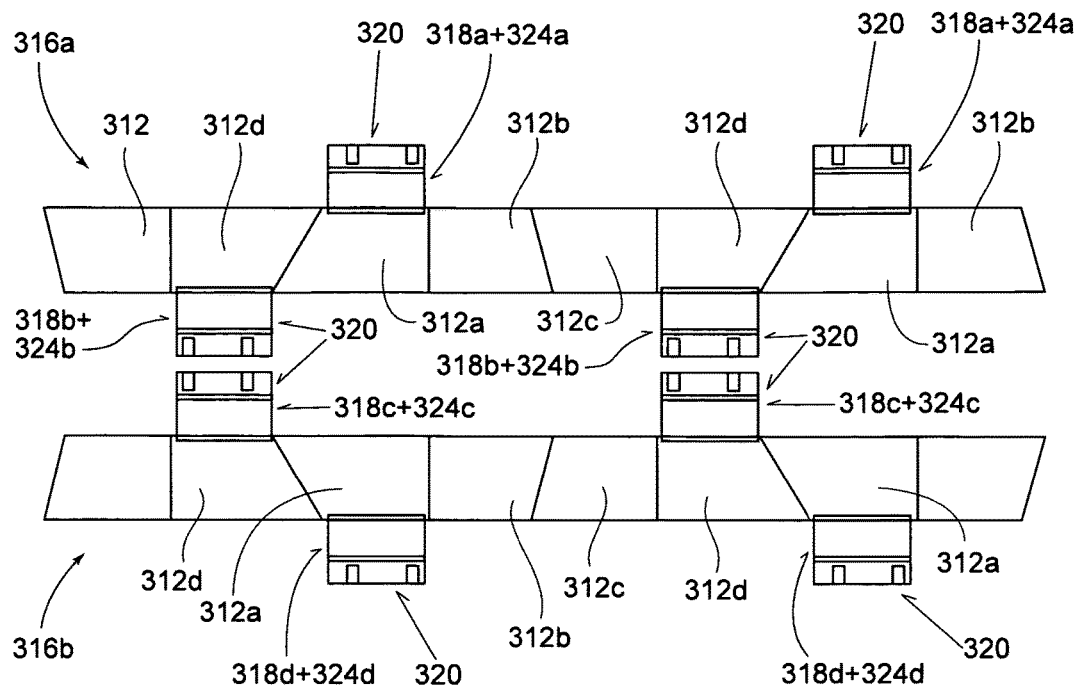

Referring now to FIG. 20, a plan view of a side-panel assembly 320 coupled to the ear tab forming material is shown. In a preferred embodiment, side-panel assembly 320, and particularly the panel 320 having configuration 318a+324a (from FIG. 19), is slip-cut onto the top of lane 316a, and particularly slip-cut and coupled to ear portion configuration 312a.

Similarly, side-panel assembly 320, and particularly the panel 320 having configuration 318b+324b (from FIG. 19), is slip-cut onto the bottom of lane 316a, and particularly slip-cut and coupled to ear portion configuration 312d.

In lane 316b, side-panel assembly 320, and particularly the panel 320 having configuration 318c+324c (from FIG. 19), is slip-cut onto the top of lane 316b, and particularly slip-cut and coupled to ear portion configuration 312d.

Similarly, side-panel assembly 320, and particularly the panel 320 having configuration 318d+324d (from FIG. 19), is slip-cut onto the bottom of lane 316b, and particularly slip-cut and coupled to ear portion configuration 312a.

The panels 320 can be coupled to the slit and spread ear tab forming material 316 in any fashion. Preferred methods may include ultrasonic bonding, adhesive bonding, heat, etc. Also, the coupling between the panels 320 and the ear tab forming material 316 could be contained in, or be a portion of a larger laminate involving other materials and bonds.

Figure 21:
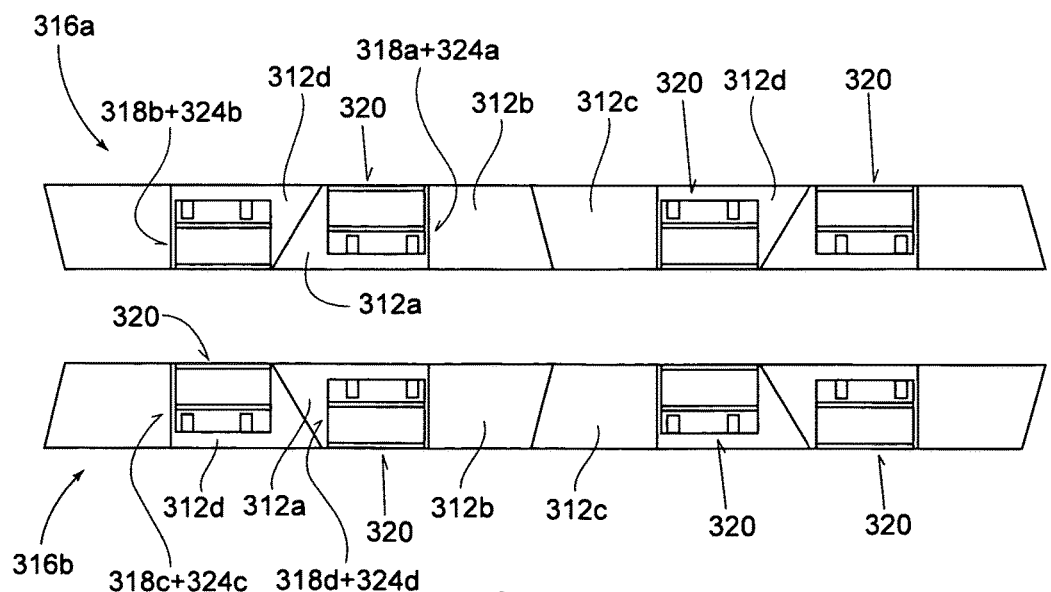
Figure 22:
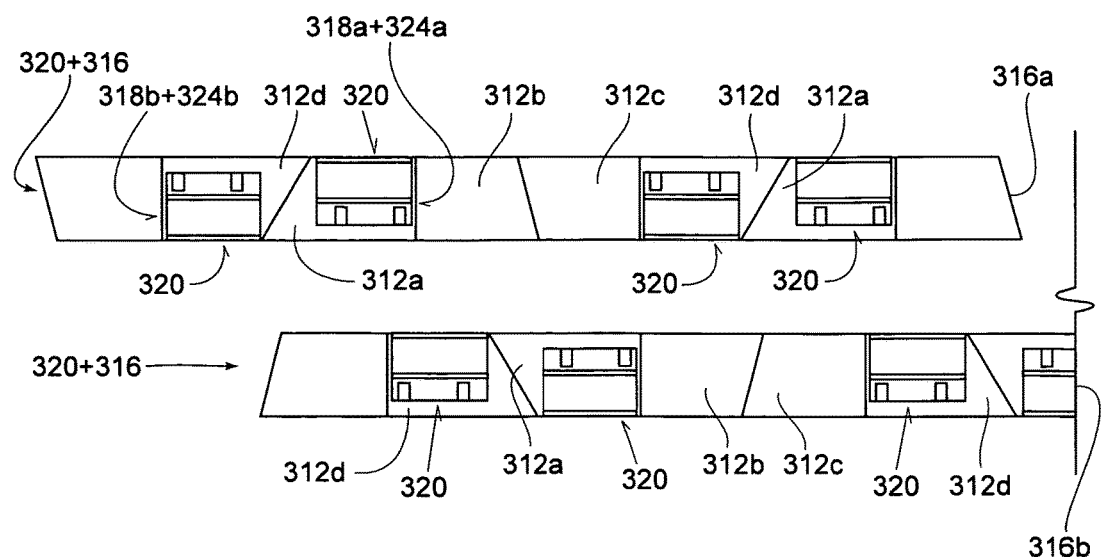
Figure 23:
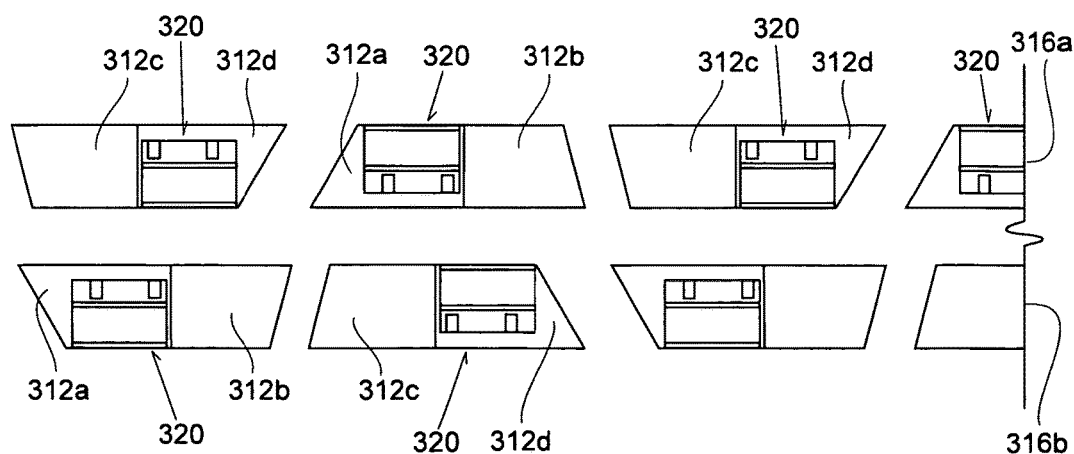

Next, referring now to FIG. 21, the side-panel assemblies 320 have been folded over (or under) the ear tab forming material 316, to conform to, and preferably be narrower than, the ear portions 312 of lanes 316a and 316.

It is desirable to process the combination of the side-panel assemblies 320 temporarily staked to the ear tab forming material 316 together, so that components do not become entangled in the machinery during processing. It is also desirable so that packaging can be accomplished orderly and uniformly. Preferably, the side-panel assemblies 320 are temporarily staked to the ear tab forming material 316. The temporary staking can be done, for instance but not by way of limitation, by a light application of adhesive, by a light compression bond, by a light compression bond assisted by slight penetration of pins through the layers, by a weak ultrasonic bond, or by other types of temporary and light bonds may be employed.

Referring now to FIGS. 22-25, after the side-panel assembly 320 has been coupled to the ear tab forming material 316, and after the side-panel assembly 320 has been folded, the side panel and wing assembly 320+316 is treated as the ear 12 was treated with reference to FIGS. 1-17. For instance, the side panel assembly 320 and ear tab 316 can be re-phased (FIGS. 22-23), then die-cut, repitched, and rotated (FIGS. 24-25).

In particular, the ear portion configurations 312c and 312d can be slip-cut together with a unit such as shown on FIG. 8 or 8a onto the machine shown on FIG. 9, which would die-cut, re-pitch and rotate every other wing assembly as shown on FIG. 24.

The 316a lane would be treated by one of the ear turner assemblies 200R (right) or 200L (left) of FIG. 11, and the 316b lane would be treated by the other of the 200R or 200L ear turner assemblies.

As a result, and as shown on FIG. 25, every other of the ear portion configurations 312c and 312d will have been rotated 180° and re-phased, such that the 312a/312b ear portion configurations will appear identical to the rotated 312c/312d ear portion configurations and the 316a and 316b lanes would be mirror images of one another.

Figure 26:
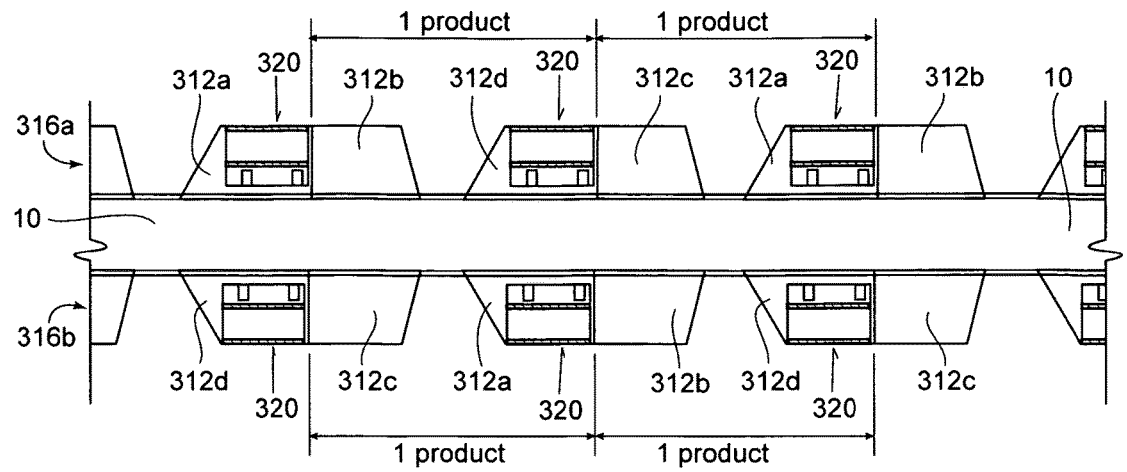

Referring now to FIG. 26, the ears 312 and side panels 320 have been properly oriented and re-phased such that right front ear 312b (front of product, no side panel 320 attached) and its associated right back ear 312d (back of product, with a side panel 320 attached and folded) are mirrored with left front ear 312c (front of product, no side panel 320 attached) and its associated left back ear 312d (back of product, with a side panel 320 attached and folded). These ears 312 and side panels 320 are introduced to, and coupled with web 10 (or chassis top sheet), typically a composite material used in formation of diapers which is generally formed of various layers of material such as plastic back sheets, absorbent pads 340 and nonwoven top sheets (visible in FIGS. 27 and 28).

Figure 27:
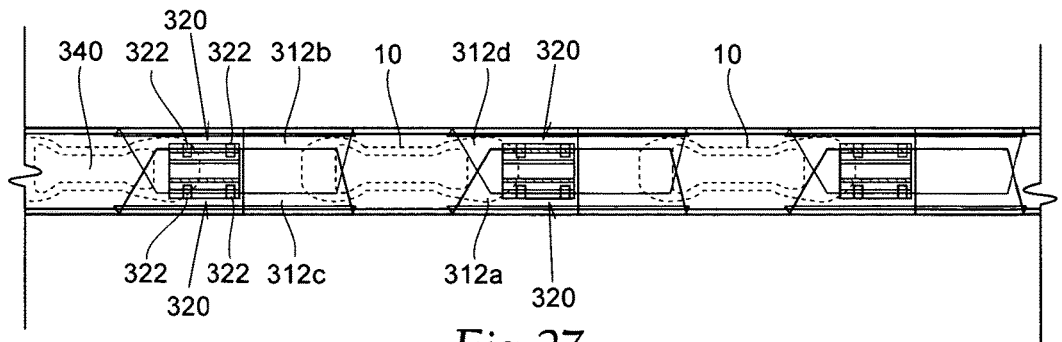

Referring now to FIG. 27, the next step is to fold the ears 312b and 312c, and 312a and 312d their associated side panels 320 down, in overlapping fashion, such that either one of lanes 316a and 316b is folded down first, followed by the other. As can be seen, the ears 312b and 312c, and 312a and 312d their associated side panels 320 are folded into, and narrower than, the width of the chassis assembly 10 in the cross-machine direction.

Figure 28:
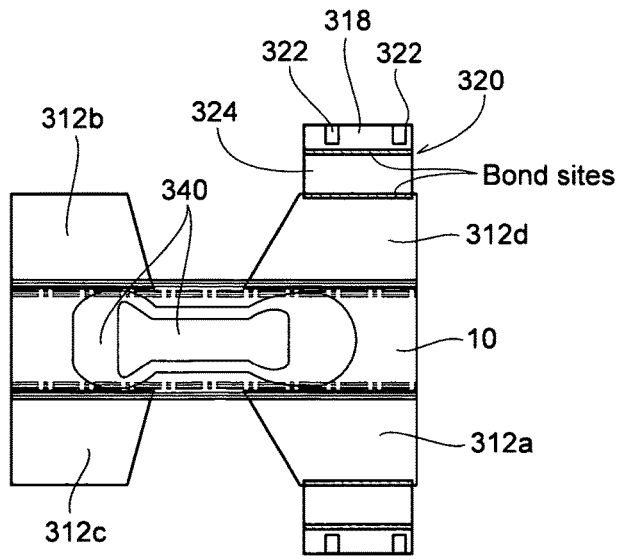

FIG. 28 is an in-use plan view of a inventive disposable product formed by the methods of the present invention. As can be seen, the ears 312a and 312d are coupled to their associated side panels 320, which had been previously folded onto the ears 312. A user can place the absorbent pad 340 in the crotch region, and couple the fastening mechanisms 322 of the side panels 320 about the waist, to reach the front of ears 312b and 312c and fasten the disposable product.

Referring now to FIGS. 29-42, schematic and plan views of methods of assembling a disposable product, including forming a nested zero waste ear to a nested zero waste wing portion, attaching ear and wing portions to a chassis top sheet, and folding the product to form a folded diaper are shown. In general, the product shown in FIGS. 29-42 is formed by cutting (preferably die cutting) a web (preferably a stretch laminate or non-woven) to form an ear, alternately turning and attaching the ear to a wing, fold and stack the ear to the wing, die cutting the wing, alternately turning and attaching wing and ear assembly to a chassis, folding and stacking a wing to a chassis non-woven.

Referring to FIG. 29, the process begins with a web portion 1000 (preferably non-woven), introduced into the system, which, as shown in FIG. 30, is split and spread into four lanes of non-woven webs 1002, 1004, 1006, and 1008, similar to that described above with reference to FIG. 19a. Instead of the rectangular cuts created of the discrete non-woven web portions 318a, 318b, 318c, and 318d of FIG. 19a, the ears 1012 shown in formation of the ear of FIGS. 29-32 can be cut of a zero waste trapezoidal configuration as shown, or other zero waste rectangular or non-rectangular configurations (such as in FIGS. 7a-7f).

As shown in FIG. 31, tapes 1022 are applied to the non-woven (similar to 322 and 322' of FIG. 19a) and folded. Next, referring to FIG. 32 the ears 1012 are die cut, repitched and rotated, in the fashion shown, for instance utilizing a machine depicted in FIGS. 11-14. The final orientations shown tapes 1022 folded in-line of the ears 1012, and the ear orientations after folding resulting in four different ear orientations, 1012a, 1012b, 1012c, and 1012d.

In orientation 1012a, the tapes 1022 are on the top side, with the long side (opposite the top side) on the bottom side. In orientation 1012b, the tapes 1022 are on the bottom side, with the long side (opposite the bottom side) on the top side. Similar rotation and resulting orientations are shown with respect to 1012c and 1012d.

Figure 35:
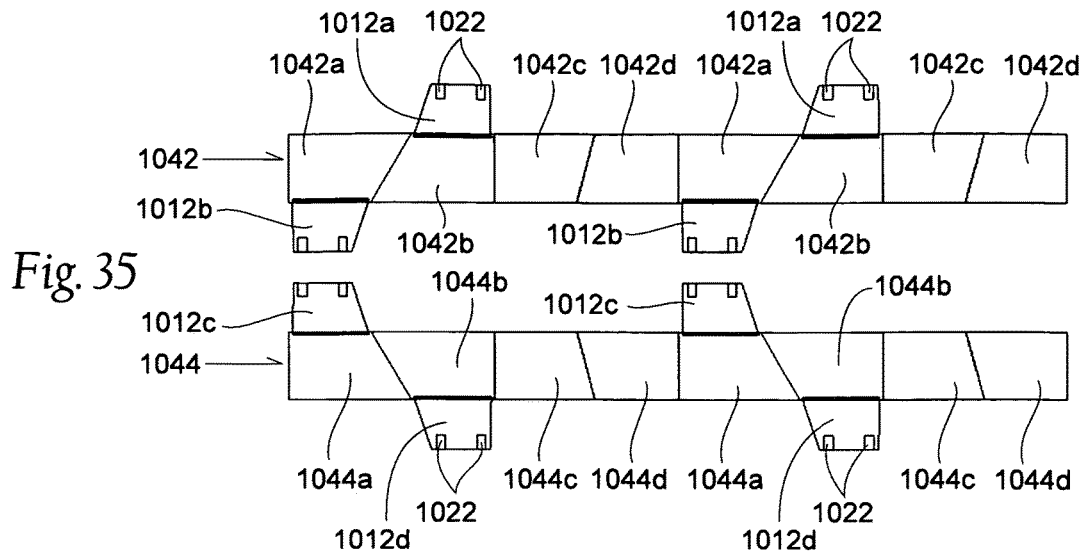

Referring to FIGS. 33 and 34, a wing web 1040, preferably non-woven for receiving folded tapes 1022 coupled to ears 1012 is shown, with wing web 1040 slit and spread such as in FIGS. 18 and 19, and the ear after cutting, repitching and rotation, is introduced to the wing web as shown in FIG. 35 (similar to FIG. 20 above).

As can be seen in FIG. 35, the folded tapes 1022 coupled to ears 1012 are introduced in the fashion shown, with the 1042 lane of wing web material receiving folded tapes 1022 coupled to ears 1012 in orientation 1012a coupled to a wing web portion 1042b, such that the short edge of the trapezoid in the cross-machine direction (left to right) receives the long edge of the ears 1012 from the 1012a orientation. The short edge of wing web portions 1042a in the cross-machine direction receives the long edge of ear 1012 in the 1012b orientation. The configuration that results is pictured in FIG. 35, also regarding lane 1044 of wing web material with the short portions of portions 1040a in the cross-machine direction receiving ears 1012 in the 1012c orientation on the long side of the 1012c orientation in the cross-machine direction, and similarly with portions 1044b receiving 1012d orientated ears 1012d as shown.

Figure 36:
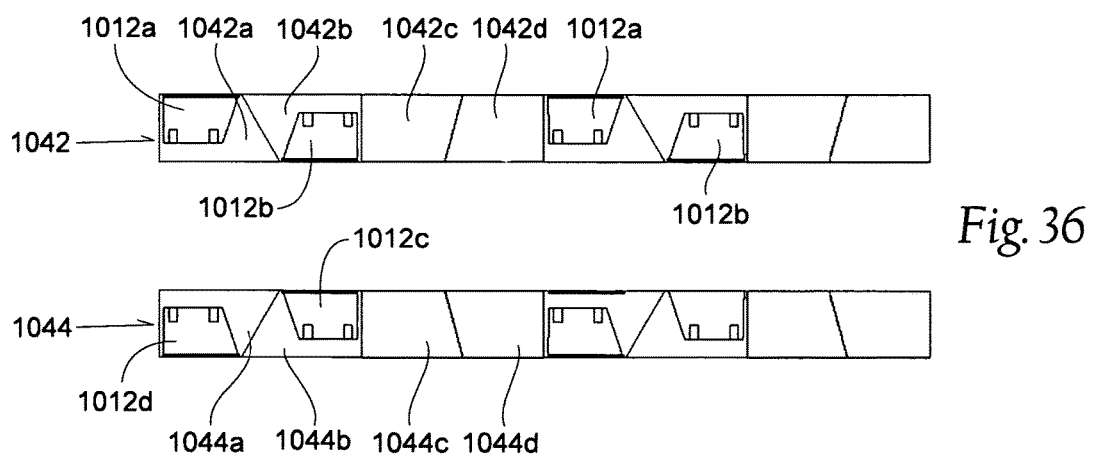
Figure 41:
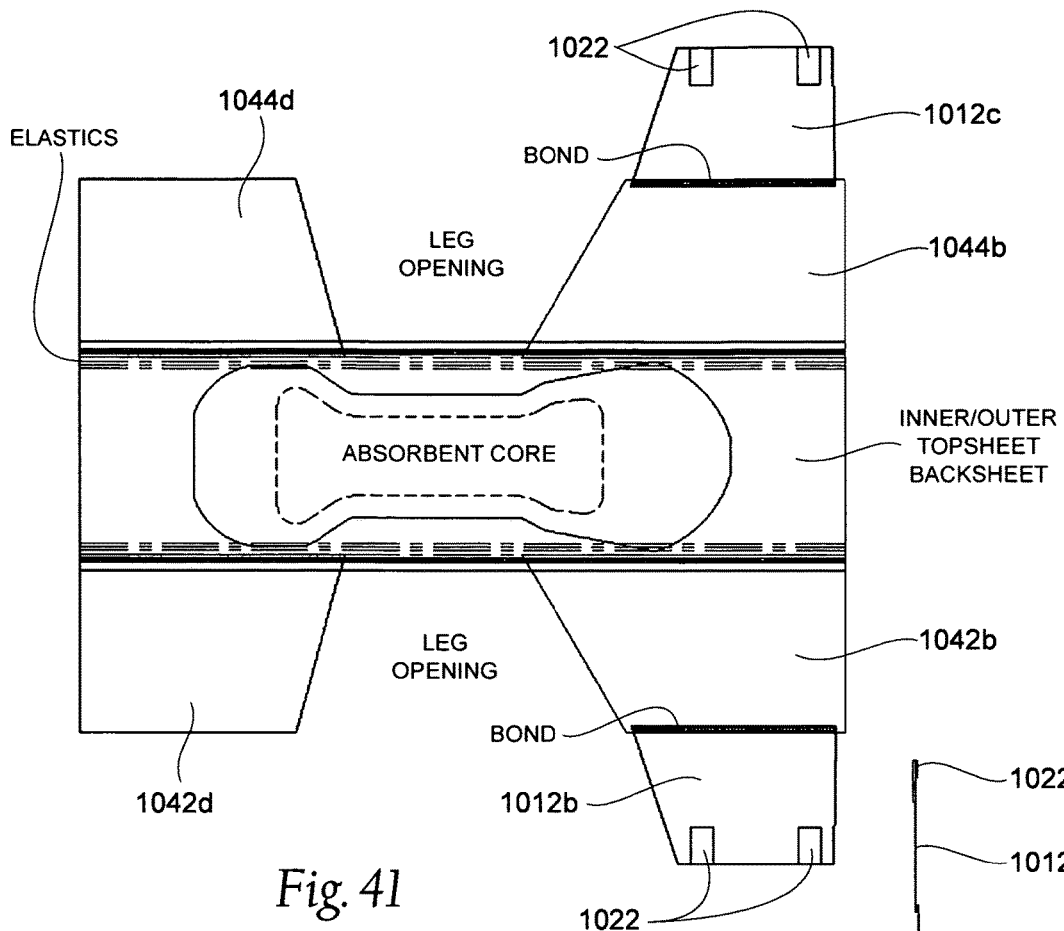
Figure 42:
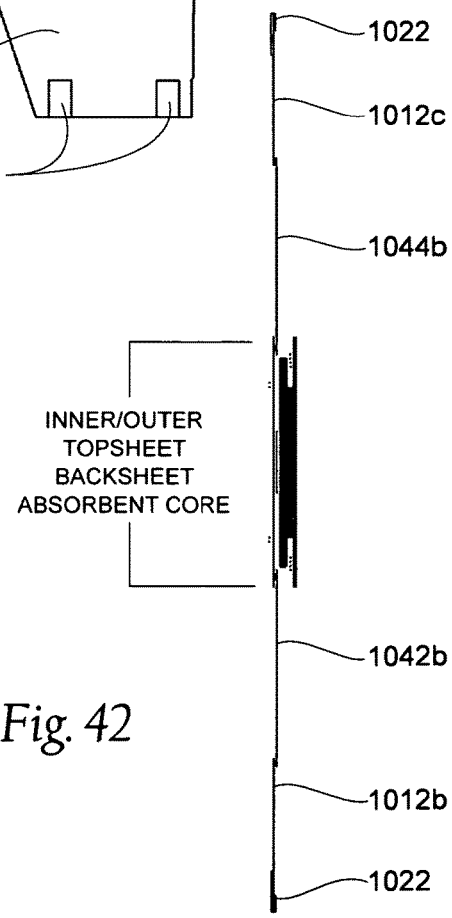

All of the ears are then folded down as shown in FIG. 36, such that portions 1042a and 1042b host ears 1012, while portions 1042c and 1042d do not host ears. Portions 1044a and 1044b host ear portions 1012 oriented in the 1012c and 1012d orientations, respectively. In FIGS. 36-40, the process continues as shown, similar to the process described above in relation to FIGS. 21-27. A representative product as shown in FIG. 41 is formed thereby, its cross section shown in FIG. 42.

Figure 37:
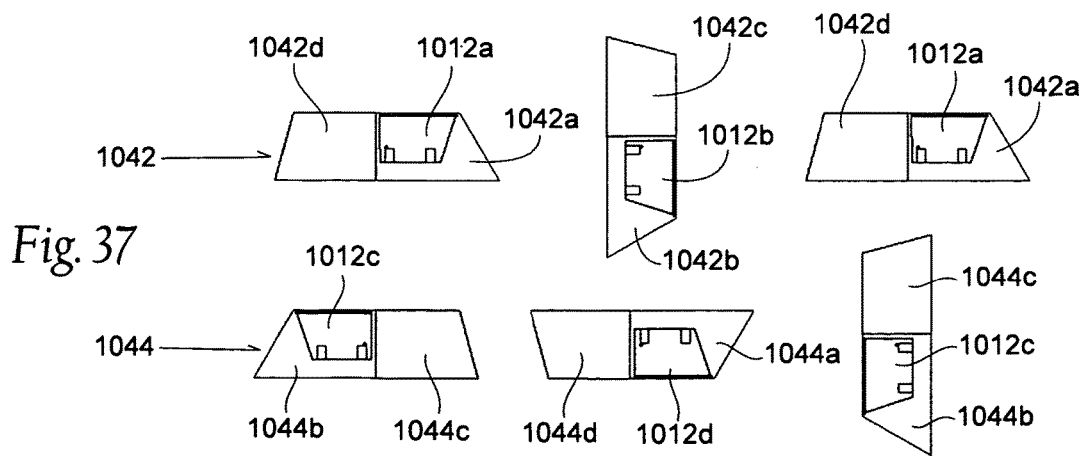

Referring to FIG. 37, it is seen that every other of the pair of elements from the 1042 lane are rotated. The 1042d and adjacent 1042a elements are not rotated, while the 1042b and adjacent 1044c are rotated 180° into sequence. Similarly with respect to lane 1044, elements 1044c and 1044b are rotated into sequence while elements 1044a and 1044d are not rotated in orientation relative to the machine direction.

What can be seen in FIG. 38 is that the elements have been positioned properly to be deposited onto a chassis web (preferably pre-formed with the elements such as an absorbent core, top sheet and back sheet as shown, but not labeled in the remaining figures). All of the folding of the ear portions 1012 on the wing portions 104s are to the top of lane 1042 and the bottom of lane 1044, so that when a chassis portion is coupled between lanes 1042 and 1044 as shown in FIG. 39, the wings 1042a carrying ears 1012d and 1044a can form two waist-wrapping portions. The space between elements 1042a and 1042c will form left leg portions and the space between elements 1044a and 1044c will form right leg portions.

Referring now to FIG. 40, the elements 1042a (carrying ear 1012a), 1042b (carrying ear 1012b), 1042c and 1042d, as well as 1044a (carrying ear 1012d), 1044b (carrying ear 1012c), 1044c and 1044d are folded over to be in-line with the chassis web 10.

Referring now to FIGS. 43-60, and additional embodiment is formed using the procedure shown therein.

Figure 43:
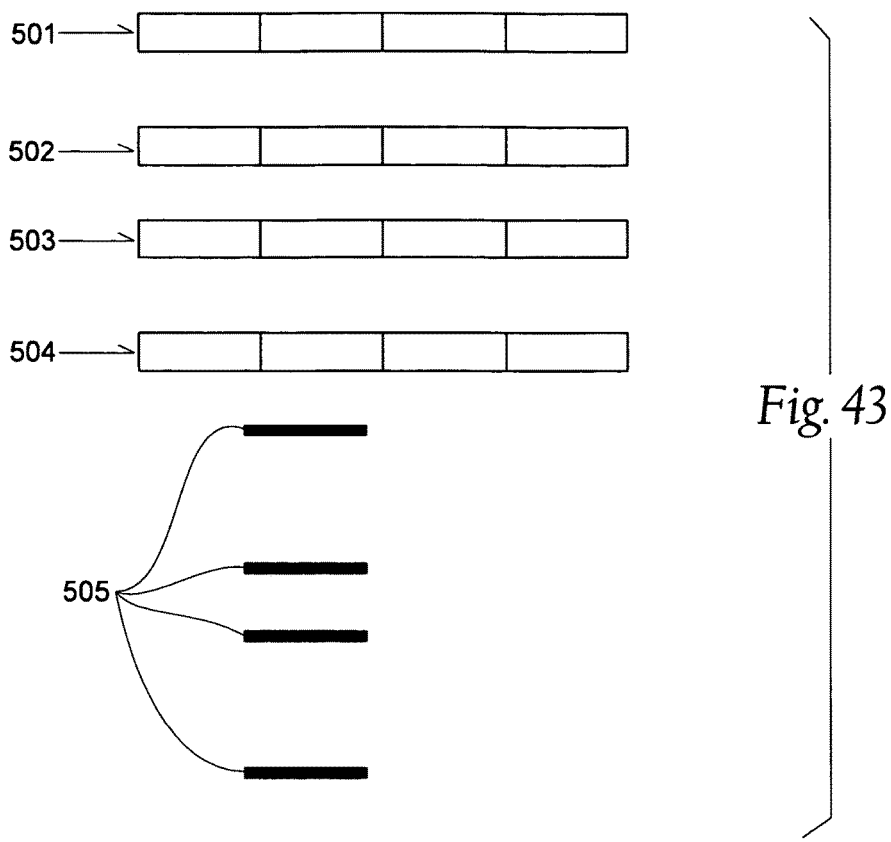
Figure 44:
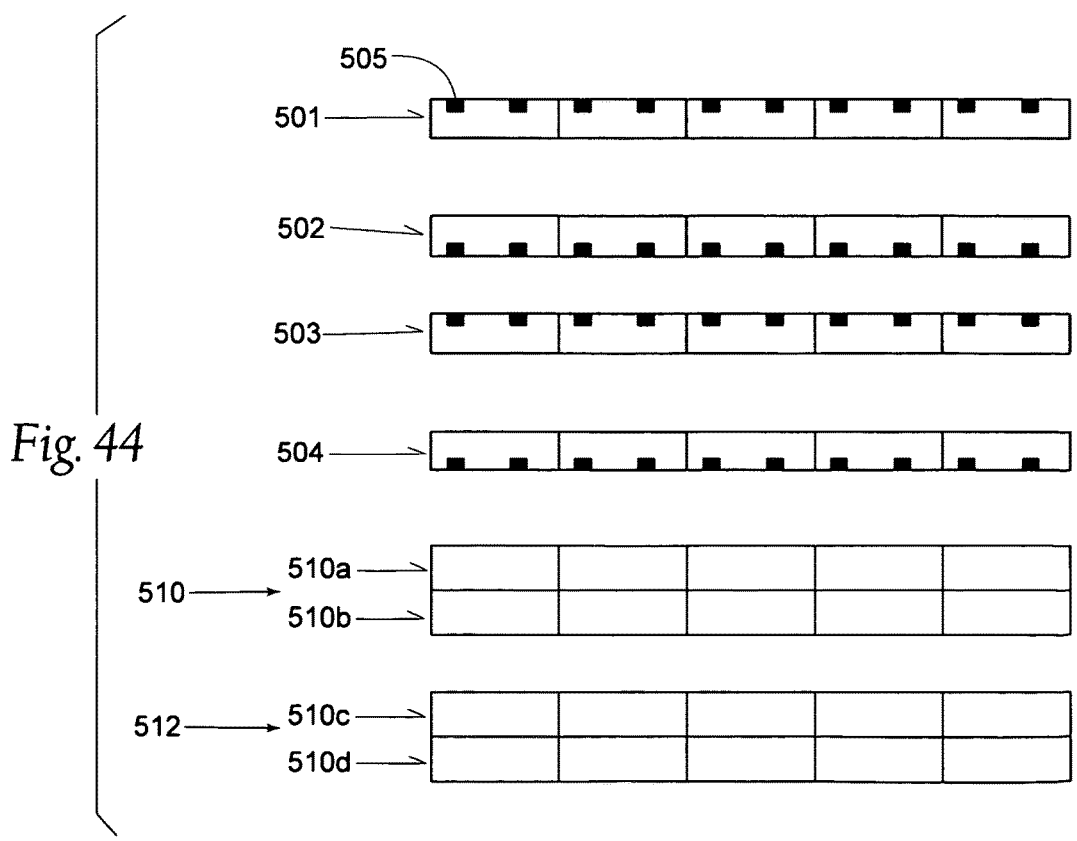

Referring to FIG. 43, a laminate is shown after slit stretching (501-504), and four lanes of hook material 505 are shown below. In FIG. 44, the hooks 505 are shown attached to the stretch laminate webs 501-504, while additional slit outer non-woven web 510 and 512 is introduced, and as shown in FIG. 45, the stretch laminate webs 501-504 are coupled to outer non-woven webs 510 and 512 as shown, for instance by ultrasonic bond methods. Next, as shown in FIG. 46, the side panel laminate is folded as shown. The side panel laminate is slit as shown in FIG. 47, forming side panel assemblies 501/501a, 502/501b, 503/501c, and 504/501d respectively.

Next, the back ear web 610a, 610b (preferably non-woven) as shown being formed in FIG. 51 and slit in FIG. 52, are introduced, preferably in slip/cut fashion to and coupled with the side panel assemblies 501/501a, 502/501b, 503/501c, and 504/501d as shown in FIG. 48.

The side panel assemblies 501/501a, 502/501b, 503/501c, and 504/501d are then folded and preferably temporarily staked together as shown in FIG. 49.

Figure 50A:
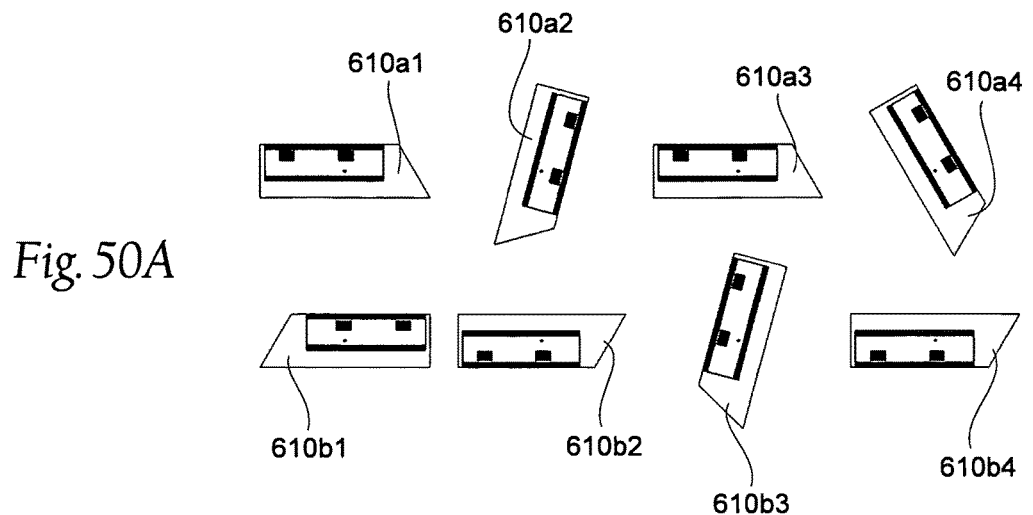
Figure 50B:
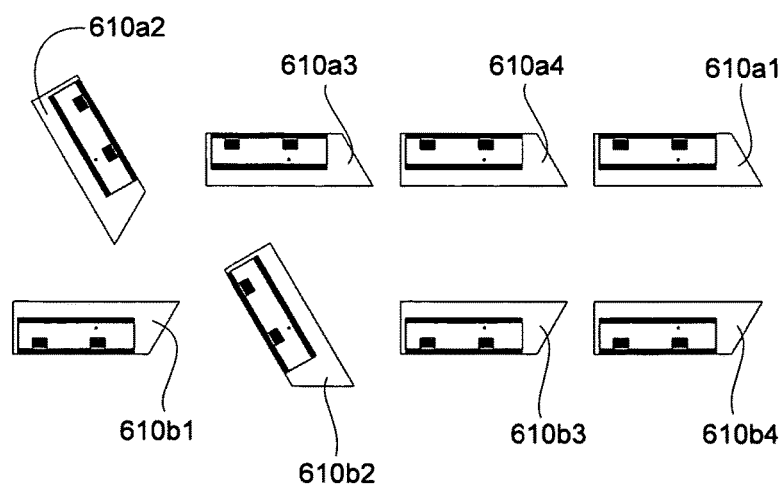

Next, the side panel assemblies side panel assemblies 501/510a, 502/510b, 503/510c, and 504/510d coupled with respective back ear web portions 610a1, 610a2, 610a3, and 610a4, and 610b1, 610b2, 610b3, and 610b4 are die cut, repitched and rotated according to FIGS. 50a to result in the end orientation shown in FIG. 50b, wherein every other of 610a1, 610a2, 610a3, and 610a4 has been rotated 180 degrees, and every other of 610b1, 610b2, 610b3, and 610b4 has also been rotated 180 degrees and rephrased to result in the matched folded right and left sets.

Figure 53:
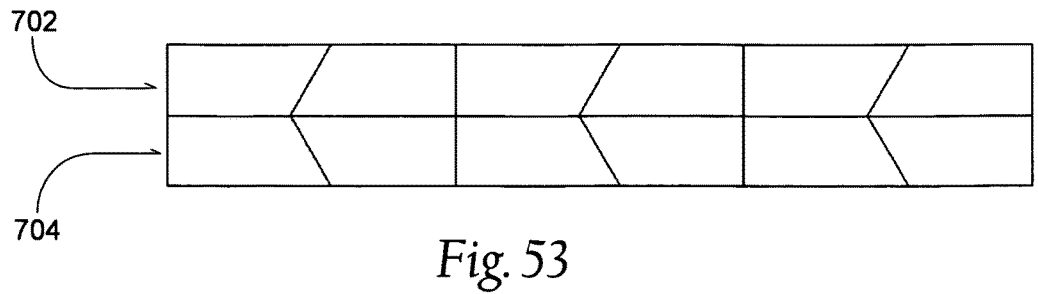
Figure 54:
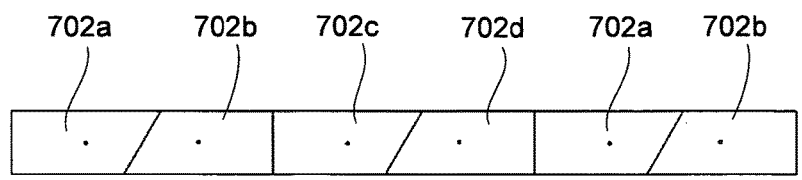
Figure 55:
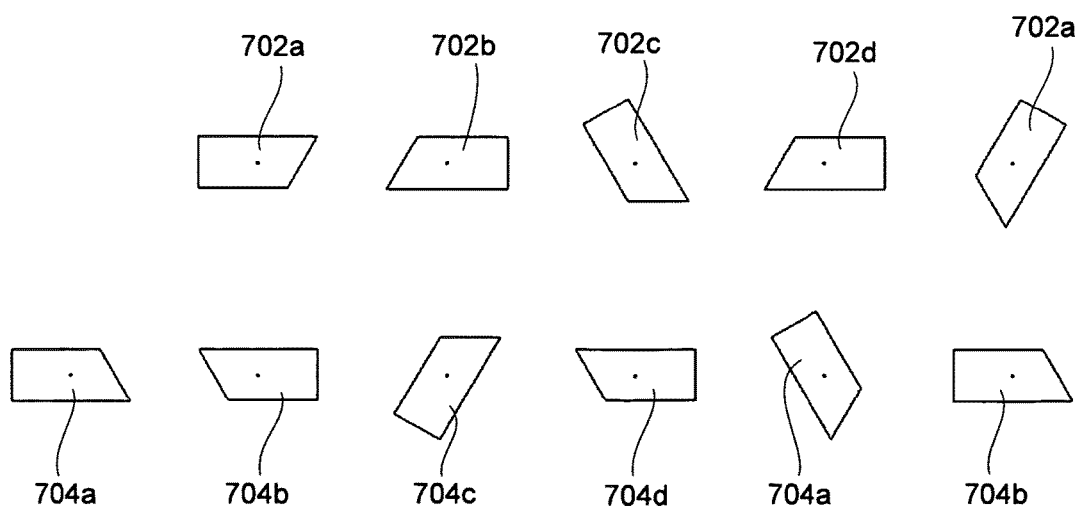

The front ear non-woven web 702/704, and particularly portions 702a, 702b, 702c, and 702d, and 704a, 704b, 704c, and 704d are shown being formed and slit in FIGS. 53 and 54, and then die cut, repitched, and rotated as shown in FIGS. 55-56.

As shown in FIG. 57, the front ear non-woven portions 702a, 702b, 702c, and 702d, and 704a, 704b, 704c, and 704d are introduced to and coupled about opposite sides of the chassis web 10, and the respective back ear web portions 610a1, 610a2, 610a3, and 610a4, having been properly aligned, as well as respective back ear web portions 610b1, 610b2, 610b3, and 610b4 also having been properly aligned, are likewise introduced to and coupled about opposite sides of the chassis web 10 as shown in FIG. 58, positioned alternating with front ear portions as shown.

Figure 59:

The front ear portions 702a, 702b, 702c, and 702d, and 704a, 704b, 704c, and 704d; and the back ear web portions 610a1, 610a2, 610a3, and 610a4; and 610b1, 610b2, 610b3, and 610b4; are all folded to conform with (slightly greater than, equal to, or slightly less than) the cross-machine directional width of the chassis 10 as shown in FIG. 59.

Figure 60:
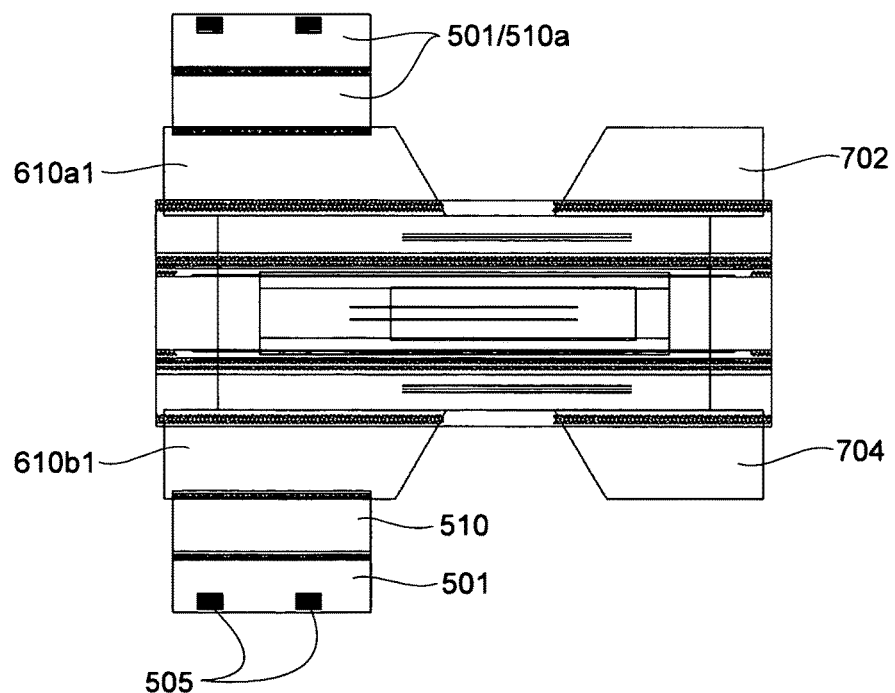

A product is formed having the configuration shown in FIG. 60.

Figure 61:
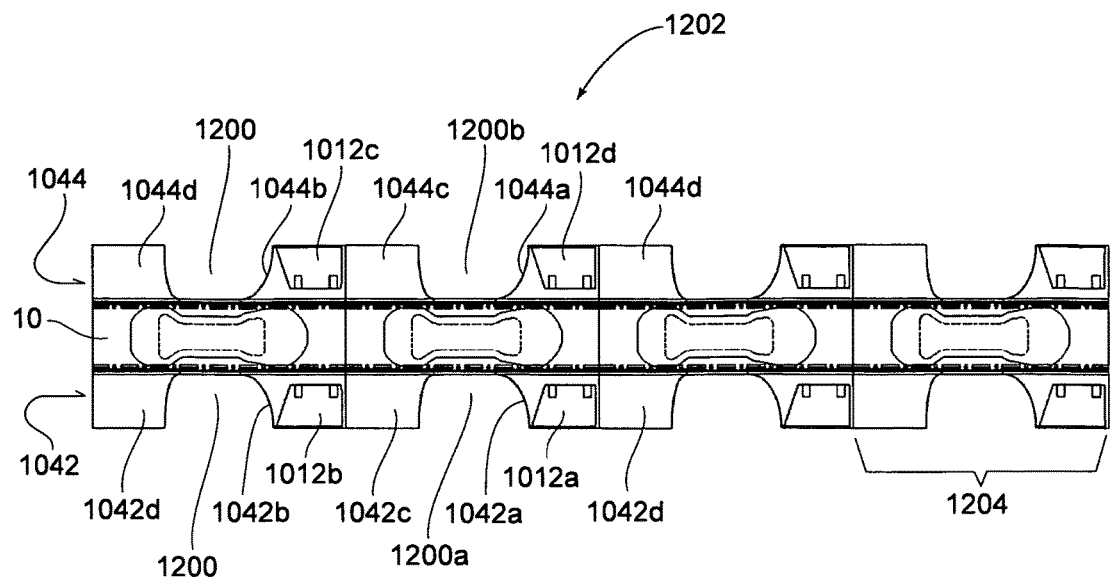
FIG. 61 is a plan view of wing assemblies coupled to a chassis assembly with chips removed from the wing assemblies.
Figure 62:
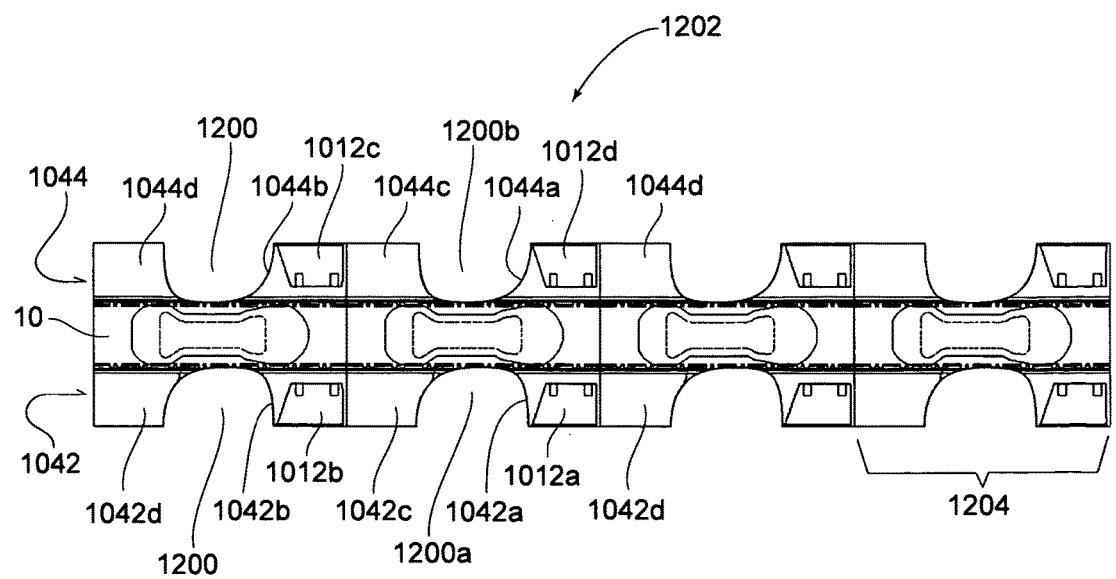
FIG. 62 is a plan view of wing assemblies coupled to a chassis assembly with chips removed from the wing assemblies and chassis assembly.

It is contemplated that it may be desirable to provide a disposable product with a contoured or curved leg opening 1200 by trimming a portion of a combined web 1202 after wings 1042a-1042d, 1044a-1044d have been placed on the chassis web 10 as shown in FIGS. 61 and 62. For illustrative purposes, the combined web 1202 and resulting disposable garment 1204 of FIGS. 39-41 are shown in FIGS. 61 and 62, however, it should be understood that the methods described herein may be utilized on any combined web. Preferably, the combined web 1202 includes a chassis web 10, a plurality of ear carrying wings 1042a, 1042b, 1044a, 1044b and non-ear carrying wings 1042c, 1042d, 1044c, 1044d as shown in FIG. 39.

Preferably, a portion of the ear carrying wings 1042a, 1042b, 1044a, 1044b and the non-ear carrying wings 1042c, 1042d, 1044c, 1044d on each side of the garment 1204 may be removed to create a contoured shape, as shown in FIG. 61. However, it is also contemplated that a portion of the chassis web 10 between the ear carrying wing 1042a, 1042b, 1044a, 1044b and non-ear carrying wing 1042c, 1042d, 1044c, 1044d may also be removed to create a contoured shape as shown in FIG. 62. For example, as shown in FIG. 61, a portion of the chassis web between a first non-ear carrying wing portion 1042d and a first ear carrying wing portion 1042b has been removed.

It is contemplated that any means known in the art may be utilized to remove the desired portions of the wings 1042a-1042d, 1044a-1044d and, if desired, chassis web 10, to create the contoured leg opening 1200. For example, and not by way of limitation, a knife roll may be utilized to cut the garment leg opening 1200 to the desired contour. In such a system, a contoured knife roll, with a cutting edge sized and configured to cut the leg opening 1200 to the desired shape would be provided.

It is contemplated that both the left 1200a and the right 1200b leg opening could be cut at the same time for example with a knife roll with two cutting surfaces, or that a pair of knife rolls, one for the left leg opening 1200a and one for the right leg opening 1200b may be utilized. Each knife roll is provided with an associated anvil, as is well known in the art. In use, the anvil and the knife roll each rotate, with the combined web 1202 to be cut between the surface of the knife roll and the anvil. As the knife roll rotates, the cutting edge cuts the combined web 1202 against the anvil.

Figure 63:
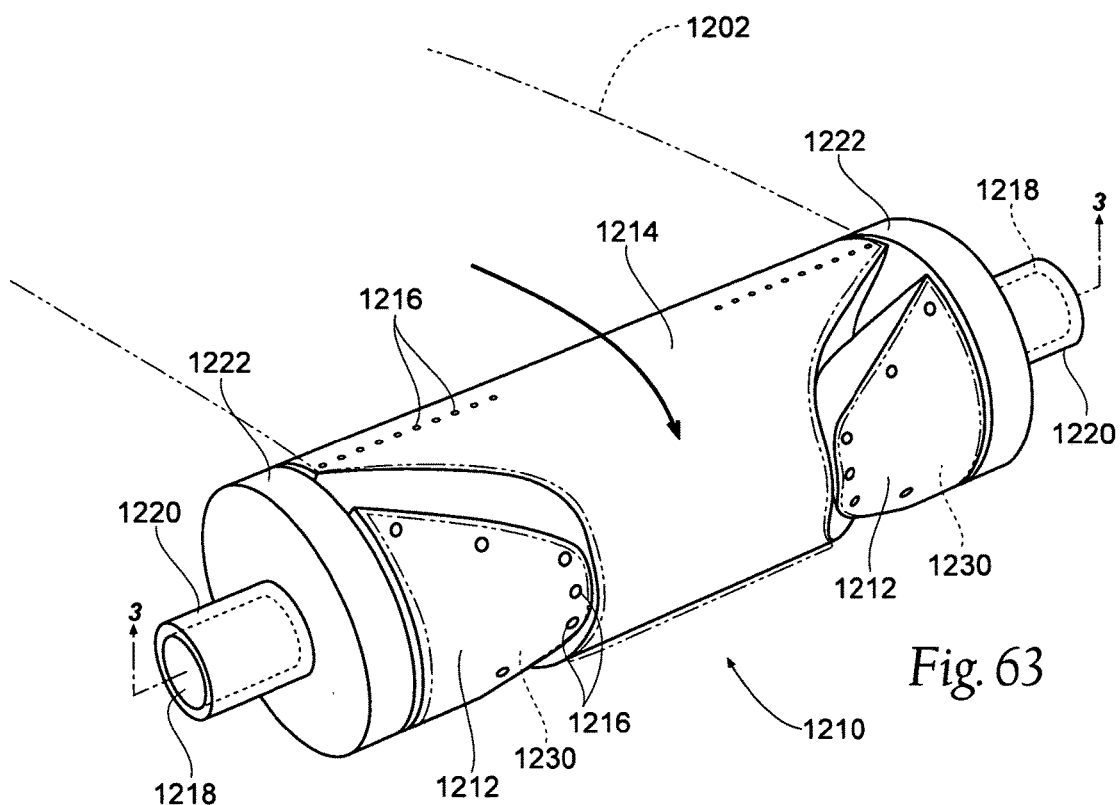
FIG. 63 is a perspective view of a trim removal system of the present invention, with an infeed chassis web, and a chip to be removed therefrom.
Figure 76:
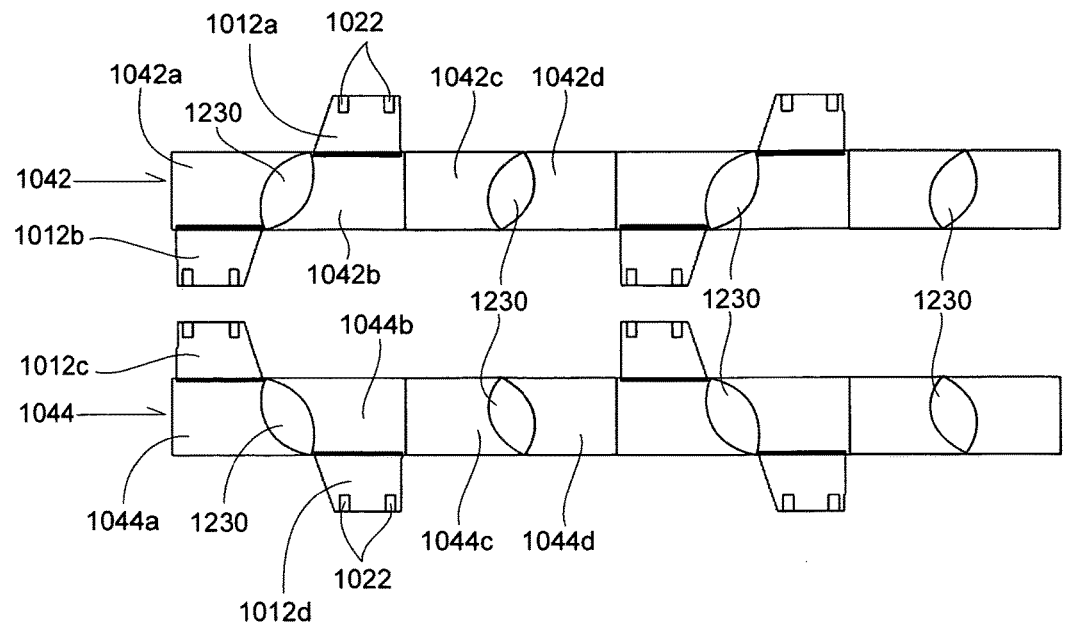
FIG. 76 is a plan view of a web of wing assemblies with chips removed from each wing assembly.

It is further contemplated that a trim removal system 1210 such as shown in FIG. 63 may be utilized to remove the cut chips from the combined web 1202. FIG. 63 shows an infeed web 1202, and a chip or chips 1230 to be removed therefrom. A transfer roll 1214 and an associated trim shoe or trim shoes 1212 are provided to engage the combined web 1202 and chips 1230. Preferably, the trim shoes 1212 are shaped complimentary with the chips 1230. Vacuum ports 1216 are provided on the transfer roll 1214 and trim shoes 1212 for maintaining the combined web 1202 and chips 1230 in close contact with the transfer roll 1214 and trim shoes 1212. It is noted that other methods of cutting the web, in addition to the particular trim removal system 1210 may be used to form the products of the present invention. It is also noted that the chip removal system 1210 as pictured, is configured to cut two chips 1230 from the incoming web 1202 at outboard portions of the incoming web 1202. Different shoe 1212 configurations can be used to cut different sized and/or shaped chips 1230, such as the chips 1230 desired to be removed from successive back ears 1042a and 1042b as shown in FIG. 76, or chips 1230 from between successive front ears 1042c and 1042d as shown in FIG. 76 if desired. Compare FIG. 76 showing chips removed between successive front ears 1042c and 1042d, and FIG. 77, with no chips between front between front ears 1042c and 1042d.

An inner axle 1218 and an outer axle 1220 are coupled to the transfer roll 1214 (or hub 1222) and the trim shoes 1212, respectively. The inner axle 1218 and the outer axle 1220 are capable of being operated at different speeds in relation to one another by servo motor (not shown). This difference in speed allows the trim shoes 1212 to rotate faster or slower with respect to the transfer roll 1214 as desired. In use, as will be described later, this speed differential creates a ripping effect by first pulling the combined web 1202 away from the chip 30 as the transfer roll 1214 is rotating faster than the shoe 1212, then by pulling the chip 1230 away from the combined web 1202 as the shoe 1212 is rotating faster than the transfer roll 1214.

Figure 64:
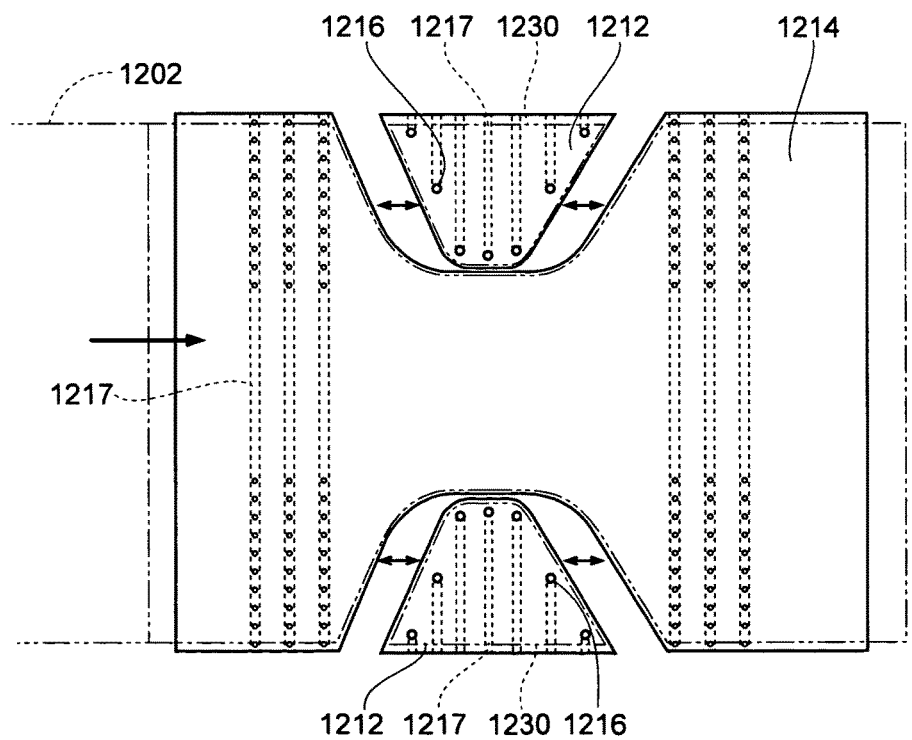
FIG. 64 is a two dimensional representation of the trim removal system of FIG. 63.

Referring now to FIG. 64, a two dimensional representation of the trim shoe 1212 and transfer roll 1214 of FIG. 63 is shown. As can be seen, vacuum channels 1217 communicate with vacuum ports 1216 on both the trim shoe 1212 and transfer roll 1214 to maintain control of the chip 1230 and combined web 1202. From this perspective, it can be seen that different rotational speeds of the trim shoe 1212 and transfer roll 1214 will cause a ripping effect by first pulling the web 1202 away from the chip 1230 as the transfer roll 1214 is rotating faster than the shoe 1212, then by pulling the chip 1230 away from the combined web 1202 as the shoe 1212 is rotating faster than the transfer roll 1214.

Figure 65:
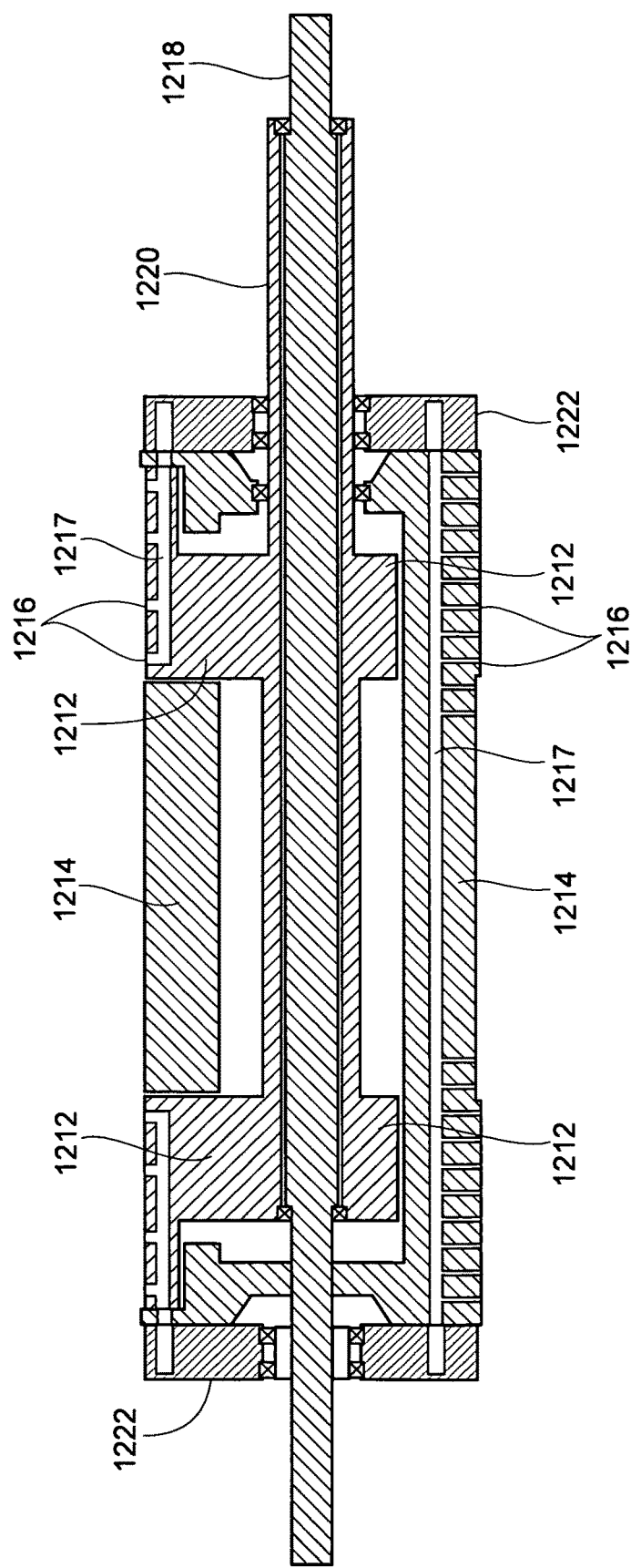
FIG. 65 is a cross sectional view of a trim removal system.

FIG. 65 is a cross sectional view of a trim shoe 1212 and transfer roll 1214 of the present invention. As can be seen, vacuum is communicated to ports 1216 through channels 1217, which are coupled to a source of vacuum (not shown).

Rotation of the outer axle 1220, which is coupled to the shoe 1212, causes rotation of the shoe 1212. The inner axle 1218 is coupled preferably to hub 1222 and to transfer roll 1214.

Referring now to FIGS. 66-71, a sequence is shown of the trim removal system 1210 removing chips 1230 and discharging them, and then the system 1210 returning to its initial position to remove more chips 1230 from the next segment of web 1202. FIGS. 72-75 are plan views of the position of the chips 1230 relative to the web 1202 at the positions associated with FIGS. 66-68 respectively, demonstrating the ripping effects of the present invention.

Figure 66:
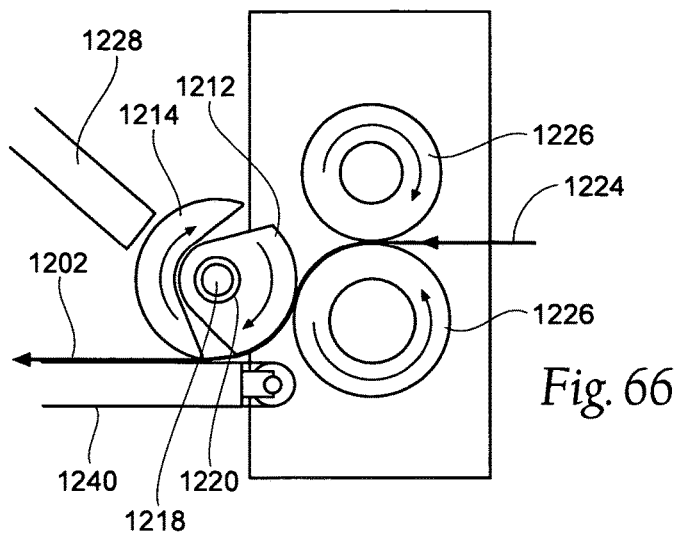
FIG. 66 is a schematic view of a trim removal system receiving an article from a transfer roll in an initial chip engaging position.

Referring now to FIG. 66, a schematic view of the system 1210 is shown receiving an infeed web 1202. In this figure, die and anvil system 1226 is shown rotating to engage the web 1202 and cut from it chips 1230 (not apparent in this view), as is well known in the art. Unfortunately, the die of the die and anvil system 1226 is susceptible to wear and tear and requires replacement once the die dulls to an unacceptable condition.

In this view, the trim shoe 1212 can be seen in an initial chip engaging position, aligned to receive the chip 1230 of the web 1202 onto the shoe 1212, which, as described previously, will be urged against the surface of the shoe 1212 by vacuum ports 1216. The trim shoe 1212 will be seen to be rotating about outer axis 1220. In this view, a discharge chute 1228 is shown for ultimately receiving waste chips 1230, and an outfeed conveyor 1240 is provided for receiving the web 1202 with the chip 1230 removed, for further processing and manufacturing steps in the composition of the disposable garments, as desired.

Inner axle 1218 is preferably operated at a first continuous speed, rotating hub 1222 and transfer roll 1214 at a continuous speed, consistent with the infeed speed of the web 1202. At this initial chip engaging position shown in FIG. 66, the outer axle 1220, and associated shoes 1212, are rotated at the same speed as the inner axle 1218.

Figure 72:
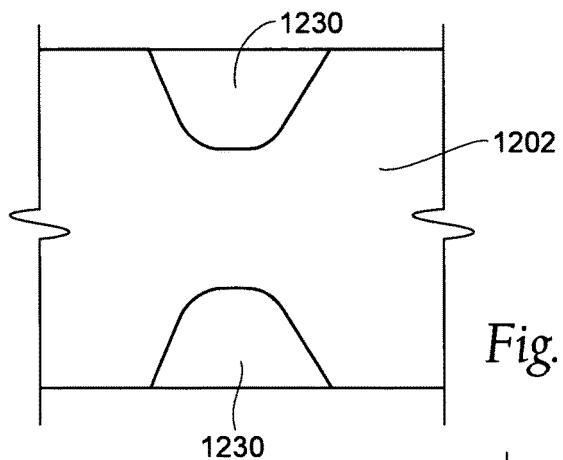
FIGS. 72-75 are plan views of the position of the chip relative to the web, demonstrating the ripping effects of the present invention.
Figure 73:
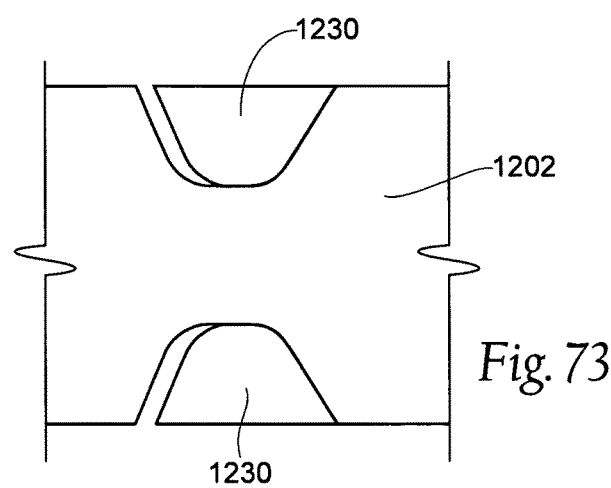

The position of the chip 1230 relative to the web 1202 is shown in FIG. 72 for the initial chip engaging position. In this position, the anvil and die 1226 has created a sever, but the chip 1230 and web 1202 could remain somewhat coupled depending on the sharpness of the die 1226. The severing method shown in the figures, particularly the severing trim removal device 1210 is just one method of forming the novel products of the present invention, other methods of severing and/or trim removal may be used.

Figure 67:
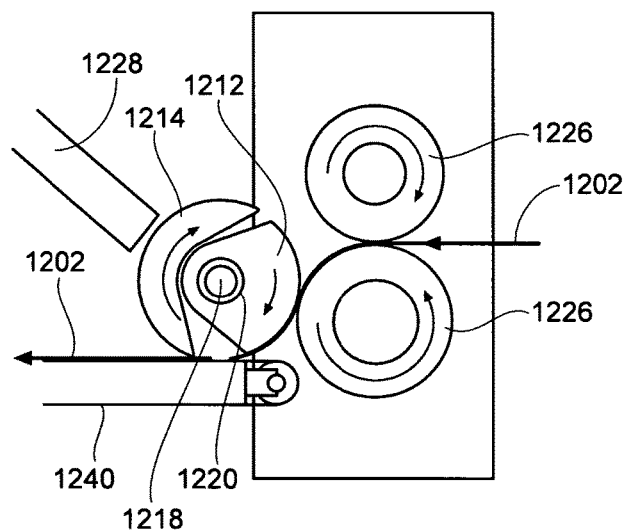
FIG. 67 is a schematic view of the trim removal system separating a first article from a second article.

Referring now to FIG. 67, the outer axle 1220, and associated shoes 1212, are toggled slower than inner axle 1218 to allow the web 1202 to be ripped from the chip 1230 at the leading edge of the chip 1230 in the machine direction. It is apparent in this view that the distance between the trailing edge of the shoes 1212 has become closer to the leading edge of the transfer roll 1214. This ripping is caused by the main web 1202 being ripped away from the chip 1230 at the leading edge of the chip 1230 as is shown in associated FIG. 73.

Figure 68:
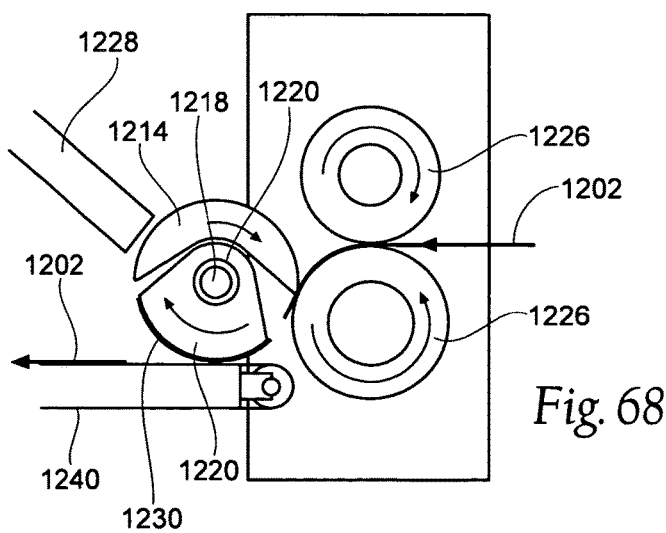
FIG. 68 is a schematic view of the trim removal system separating trim from the first article.
Figure 74:
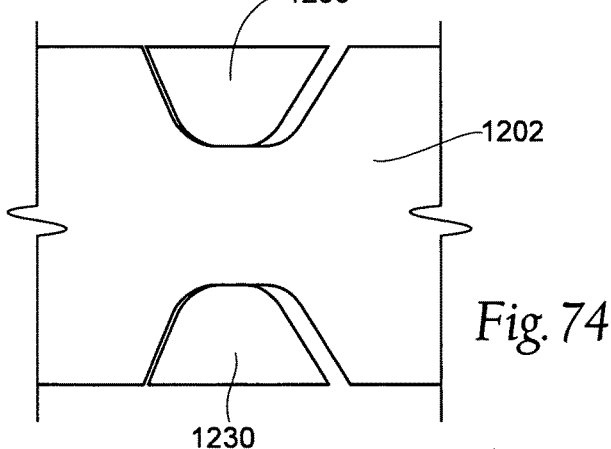

Referring now to FIG. 68, the outer axle 1220 is toggled equal to and then faster than the inner axle 1218, to allow the chips 1230 to rip from the web 1202 at the trailing edge of the chips 30 as is shown in associated FIG. 74. At this point in the process, the chip 1230 will be removed from the web 1202 by ripping first the main web 1202 away from the chip 1230 at the leading edge of the chip 1230, and next by ripping the trailing edge of the chip 1230 from the web 1202.

Figure 75:
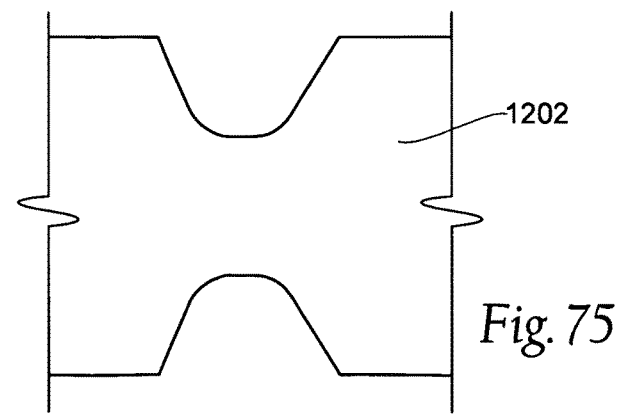

The outfeed conveyor 1240 is provided for receiving the web 1202 with the chip 1230 removed as shown in FIG. 75, for further processing and manufacturing steps in the composition of the disposable garments, as desired. The vacuum of the transfer roll 1214 can be turned off at this point to allow for release of the web 1202 to the conveyor, for instance in accordance with application Ser. No. 11/141,552, entitled "High Speed Vacuum Porting" which is incorporated herein by reference.

Figure 69:
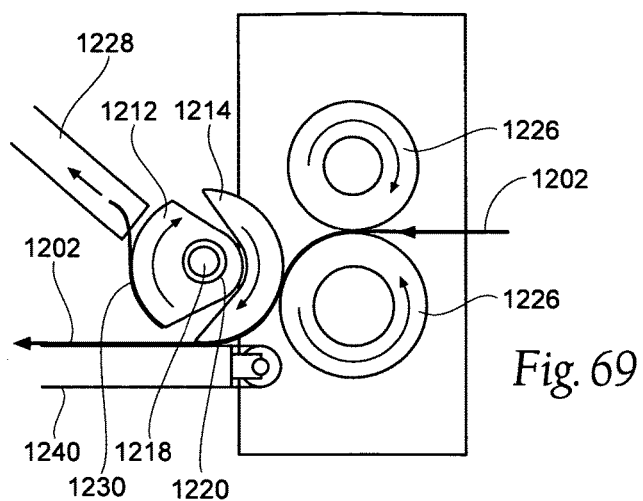
FIG. 69 is a schematic view of the trim removal system discharging the trim.
Figure 70:
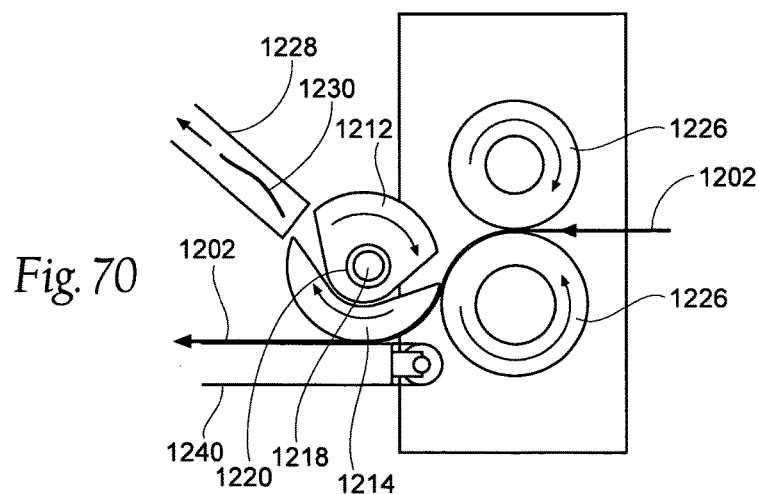
FIG. 70 is a schematic view of the trim removal system returning to its initial chip engaging position.
Figure 71:
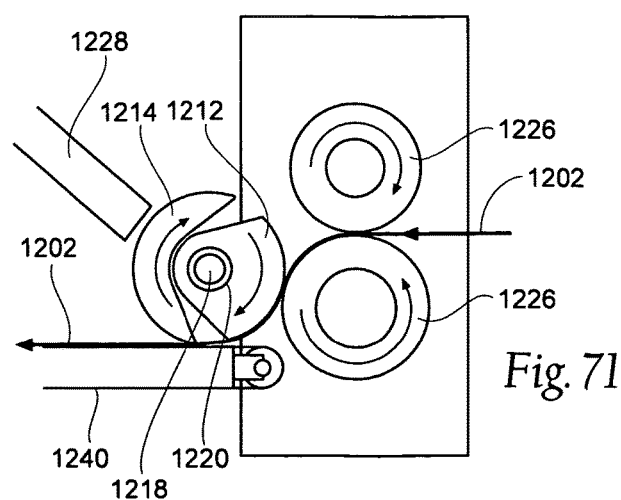
FIG. 71 is a schematic view of the trim removal system returned to its initial chip engaging position.

Referring now to FIG. 69, the chip 1230 is discharged into a discharge chute 1228, which is preferably vacuum assisted, although other collection means would satisfactorily accomplish the function of collecting waste chips 1230. It is noted that vacuum is allowed to turn off of the shoes 1212 to allow the chips 1230 to release into the chute 1228. Alternatively a vacuum in the chute 1228 could simply be provided that is stronger than the vacuum applied to the shoes 1212.

The rotational speed of the shoes 1212 and outer axle 1220, which were first operated at a speed roughly equal to inner axle 1218, rotating hub 1222 and transfer roll 1214, initially decreased, or lagged as is shown by comparing FIG. 66 with FIG. 67.

Next, the rotational speed of the shoes 1212 and outer axle 1220, increased, or surged relative to the inner axle 1218, rotating hub 1222 and transfer roll 1214.

In order to return to the initial chip engaging position, the rotational speed of the shoes 1212 and outer axle 1220, must again decrease, or lag relative to the inner axle 1218, rotating hub 1222 and transfer roll 1214. This lag is apparent by comparing FIG. 68 to FIGS. 69, 70 and 71. Finally, in FIG. 71, through one revolution, the system 1210 has removed and discharged the chips 1230, discharged the web 1202 for further processing, and the shoes 1212 have been returned to their initial position to remove more chips 1230 from the next segment of web 1202.

It is contemplated that the die of the die and anvil system 1226 in the above described trim removal apparatus may be replaced by a perforating apparatus. The perforating apparatus preferably forms the chips 1230 on the web 1202, but does not completely sever the chips 1230 from the web 1202. The perforated chips 1230 perforated could then be removed from the web 1202 in the same manner described above. The perforating apparatus may take any form known in the art including, but not limited to, a perforating die roll.

It is further contemplated that the chips may be removed from the wings 1042a-1042d, 1044a-1044d prior to attaching the wings 1042a-1042d, 1044a-1044d to the chassis web 10. The chips may be removed from the wings 1042a-1042d, 1044a-1044d, using any means known in the art. For example, the wing web 1042, 1044 may be fed between an anvil and knife roll, the knife roll having a cutting edge sized and configured to cut the desired chips from the wings 1042a-1042d, 1044a-1044d.

Although the illustrated embodiments of FIGS. 61, 62 and 76 show a particular configuration or shape of chip being removed from the wings 1042a-1042d, 1044a-1044d and web 10, is contemplated that the chips removed from the wings 1042a-1042d, 1044a-1044d could take any desired shapes to provide a contoured leg opening 1200.

Figure 77:
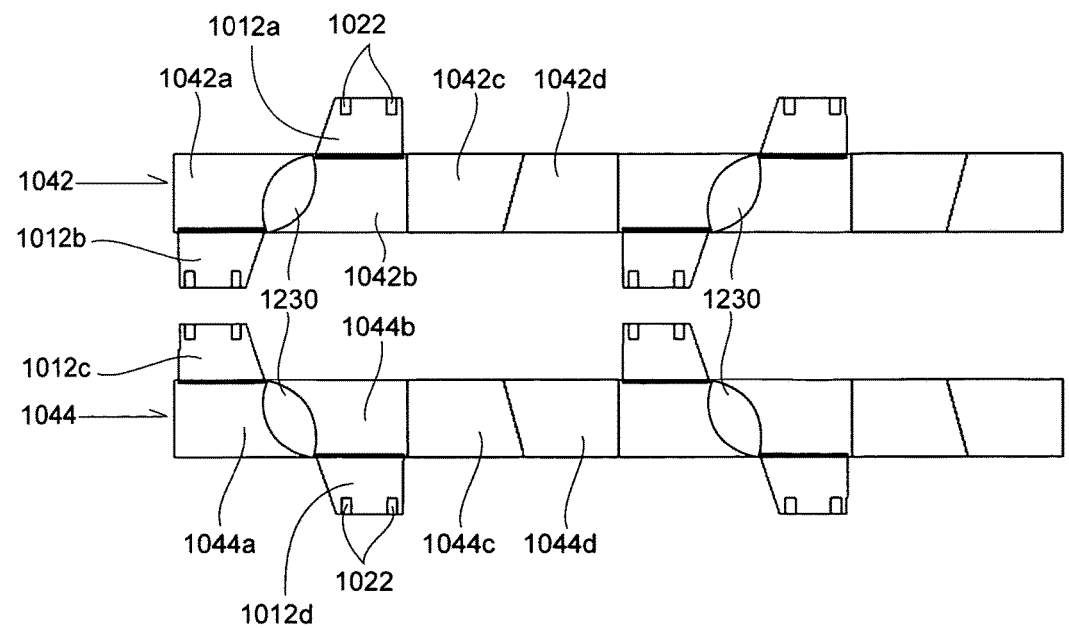
FIG. 77 is a plan view of wing assemblies with chips removed from the selected wing assemblies.

It is further contemplated that, if desired, chips could be removed from only the ear carrying wings 1042a, 1042b, 1044a, 1044b or the non-ear carrying wings 1042c, 1042d, 1044c, 1044d. For example, FIG. 77 shows a chip removed from only the ear carrying wings 1042a, 1042b, 1044a, 1044b. The chips may be cut from the desired wings 1042a-1042d, 1044a-1044d using any means known in the art, including those means described above.

Figure 78:
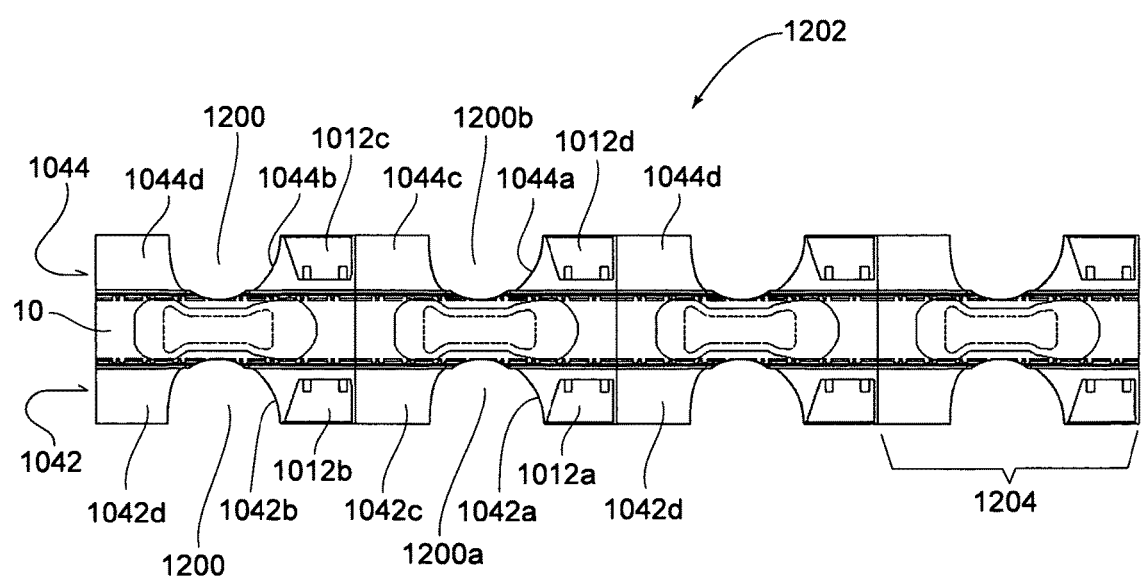
FIG. 78 is a plan view of wing assemblies coupled to a chassis assembly with chips removed from the wing assemblies and chassis assembly.

It is further contemplated that chips may be removed from the wings 1042a-1042d, 1044a-1044d and the chassis 10 in separate steps as shown in FIG. 78. For example, chips may be cut from the wings 1042*a*-1042*d*, 1044*a*-1044*d* in a first step and then cut from the web 10 in a second step, or vice versa. The chips may be cut from the wings 1042*a*-1042*d*, 1044*a*-1044*d* and web 10 using any means known in the art, including those means described above.

Referring now to FIGS. 79-90, using the principles of the present invention, several product configuration variations are shown. For instance, it is possible to pre-apply either front 1042 (*c* or *d*) or 1044 (*c* or *d*) or back 1042 (*a* or *b*) or 1044 (*a* or *b*) ears to a chassis web using previously known slip/cut techniques (e.g., the slip/cut applied ears 1144 shown in FIG. 79), and then use the alternate rotation technique of the present invention to assemble a novel product configuration (see, e.g., FIG. 79). Similarly, it is possible to post-apply either front or back ears to a chassis web using previously known slip/cut techniques, after using the alternate rotation technique of the present invention to assemble a novel product configuration, resulting in a configuration such as FIG. 79. In this method, the slip/cut technique is used to, for instance, apply each front ear 1144 (both left and right front ears 1144, FIG. 79), and the alternating rotation technique described previously is used to apply each back ear portion (e.g., 1042*b* and 1044*b*, FIG. 79)

Figure 79:
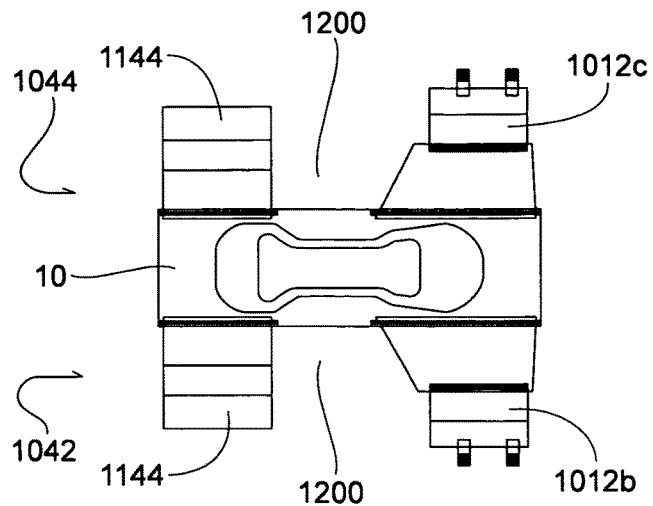
FIG. 79 is a plan view of a product variation showing a slip/cut applied front ear, alternately rotated back ears, and extension panels extending from the back ears.

Additionally, it is seen that extension panels 1012 can be applied or not, if desired (compare FIG. 79 with extension panels 1012 and FIG. 85, without extension panels 1012) to the back ear portions 1044 if desired, and that those extension panels 1012 can be paired with the back ears 1044 with the extension panels 1012 in pre-folded (or unfolded) condition if desired (e.g., shown unfolded, with fold lines, on FIG. 79). Additionally, front ear portions 1144 can arrive at the chassis web in a pre-folded condition (e.g., shown unfolded, with fold lines, on FIG. 79), if a wider front ear portion 1144 is desired. These configurations can also be combined with the chip removal technique previously discussed (or any other chip removal or die cutting or ear web formation technique), in which curved portions of either one or both ears 1144, 1044, or 1042, or a leg portion 1200*a* and 1200*b* of the chassis, or any combination of the foregoing (see, e.g., FIGS. 80 and 81), the product configurations of FIGS. 79-90 can be achieved.

Referring to FIG. 79, a plan view of a product variation showing slip/cut applied front ears 1144, alternately rotated back ears 1042, 1044, and extension panels 1012 extending from the back ears 1042, 1044 is shown.

Figure 80:
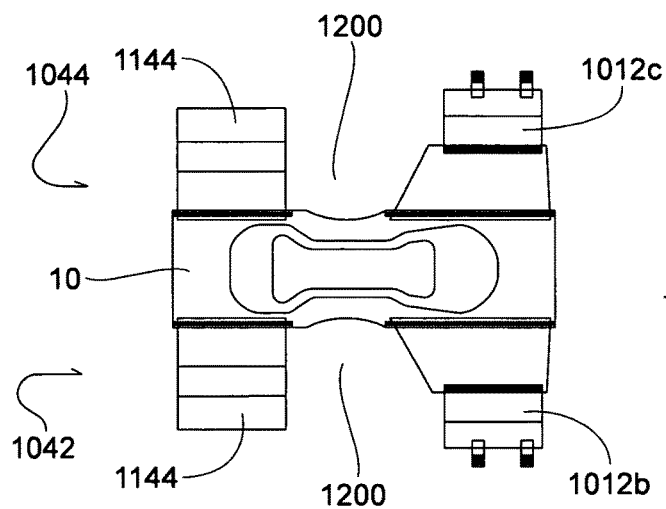
FIG. 80 is a plan view of a product variation showing a slip/cut applied front ear, alternately rotated back ears, and extension panels extending from the back ears, and a die cut chassis.

Referring to FIG. 80, the embodiment of FIG. 79 is shown, with the additional product feature of leg portions 1200*a* and 1200*b* of the chassis removed from the chassis, to fit around the leg of a wearer.

Figure 81:
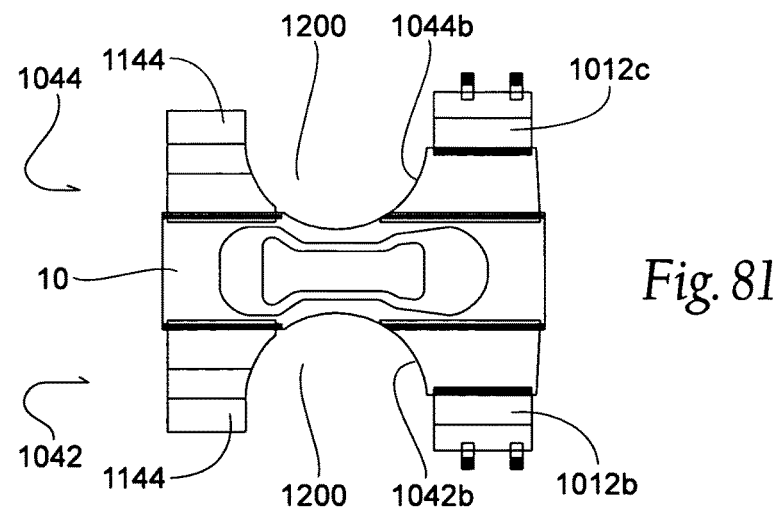
FIG. 81 is a plan view of a product variation showing a slip/cut applied front ear, alternately rotated back ears, and extension panels extending from the back ears, die cut front and back ear portions, and a die cut chassis.

Referring to FIG. 81, the embodiment of FIG. 80 is shown, with the additional product feature of chips 1230 having been removed from both the front ear and back ear portions of the product, for instance using the severing and chip removal pattern of FIG. 76.

Figure 82:
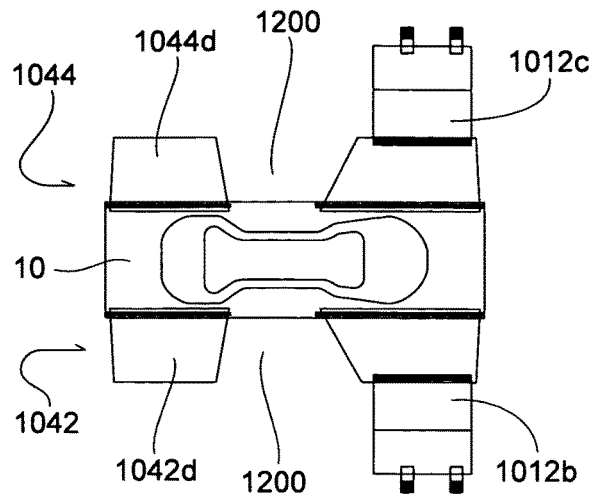
FIG. 82 is a plan view of a product variation showing alternately rotated front ears, alternately rotated back ears, and extension panels extending from the back ears.

Referring to FIG. 82, a plan view of a product variation showing alternately rotated front and back ears using the techniques described above (e.g., using the technique to construct the embodiments shown in FIG. 28 and/or FIG. 60 above) is shown.

Figure 83:
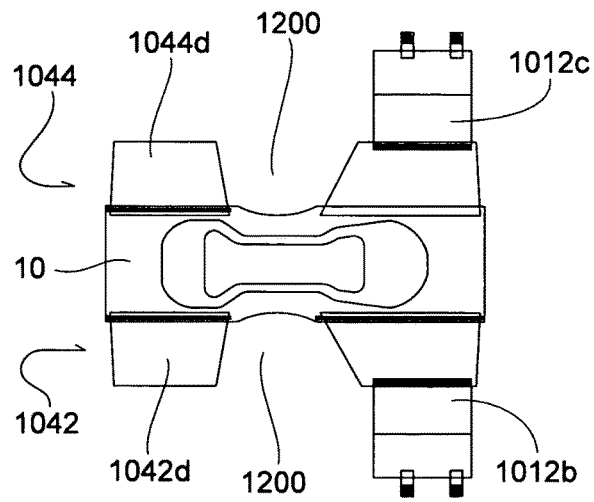
FIG. 83 is a plan view of a product variation showing alternately rotated front ears, alternately rotated back ears, extension panels extending from the back ears, and a die cut chassis.

Referring to FIG. 83, the embodiment of FIG. 82 is shown, with the additional product feature of leg portions 1200*a* and 1200*b* of the chassis removed from the chassis, to fit around the leg of a wearer.

Figure 84:
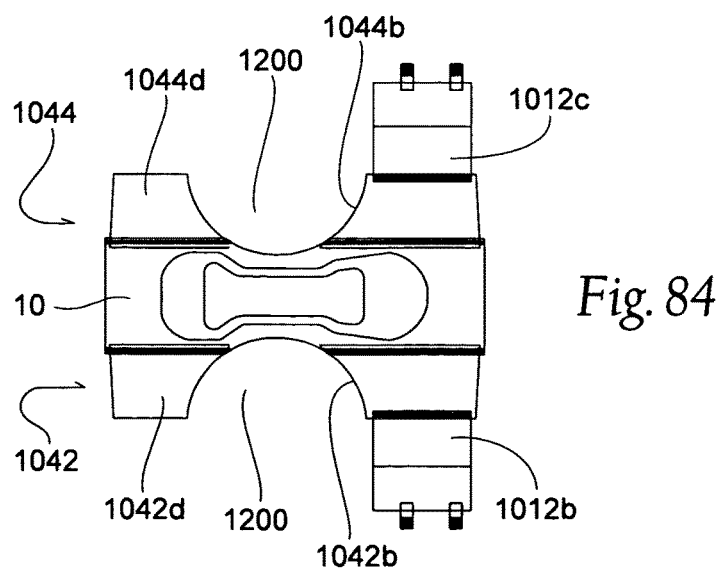
FIG. 84 is a plan view of a product variation showing alternately rotated front ears, alternately rotated back ears, extension panels extending from the back ears, a die cut chassis, and die cut ears.

Referring to FIG. 84, the embodiment of FIG. 83 is shown with the additional product feature of chips 1230 having been removed from both the front ear and back ear portions of the product, for instance using the severing and chip removal pattern of FIG. 76.

Figure 85:
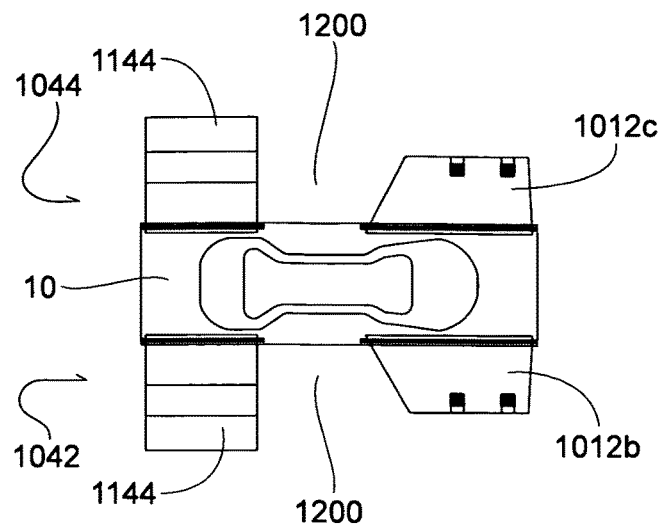
FIG. 85 is a plan view of a product variation showing slip/cut applied front ears, and alternately rotated back ears.

Referring to FIG. 85 a plan view of a product variation showing slip/cut applied front ears 1144, and alternately rotated back ears is shown.

Figure 86:
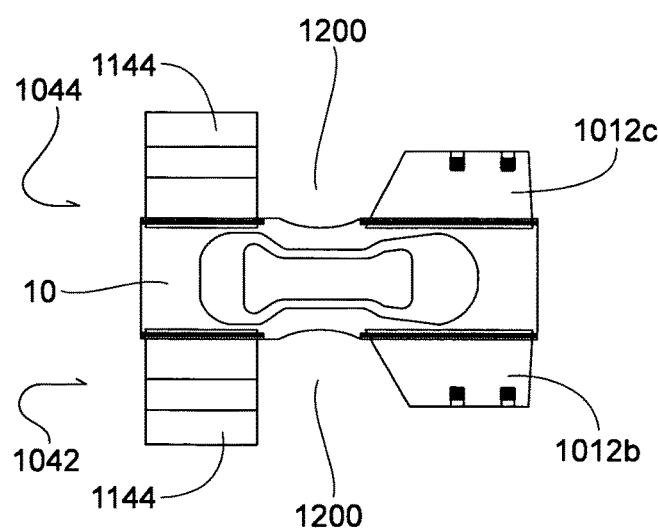
FIG. 86 is a plan view of a product variation showing slip/cut applied front ears, and alternately rotated back ears, and a die cut chassis.

Referring to FIG. 86, the embodiment of FIG. 85 is shown, with the additional product feature of leg portions 1200*a* and 1200*b* of the chassis removed from the chassis, to fit around the leg of a wearer.

Figure 87:
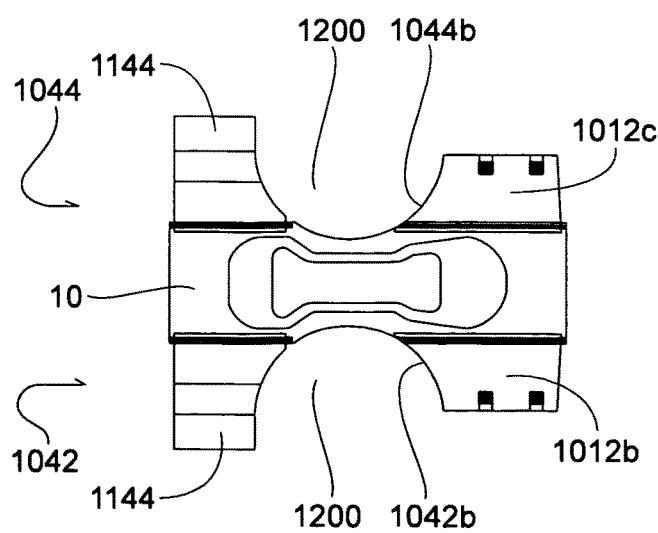
FIG. 87 is a plan view of a product variation showing slip/cut applied front ears, and alternately rotated back ears, a die cut chassis, and die cut ears.

Referring to FIG. 87, the embodiment of FIG. 86 is shown with the additional product feature of chips 1230 having been removed from both the front ear and back ear portions of the product, for instance using the severing and chip removal pattern of FIG. 76.

Figure 88:
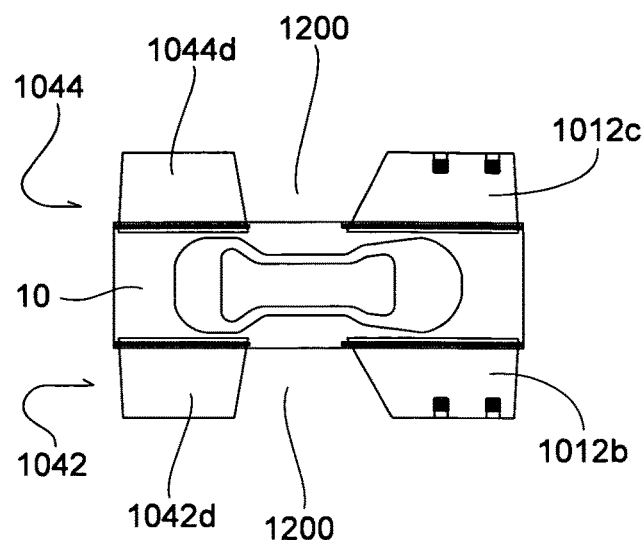
FIG. 88 is a plan view of a product variation showing alternately rotated applied front ears, and alternately rotated back ears.

Referring to FIG. 88, a plan view of a product variation showing alternately rotated applied front ears, and alternately rotated back ears, using the previously described techniques, for instance the technique used to construct the product configuration shown in FIG. 28 is shown, with the exception that no extension panel is present in the embodiment shown in FIG. 88.

Figure 89:
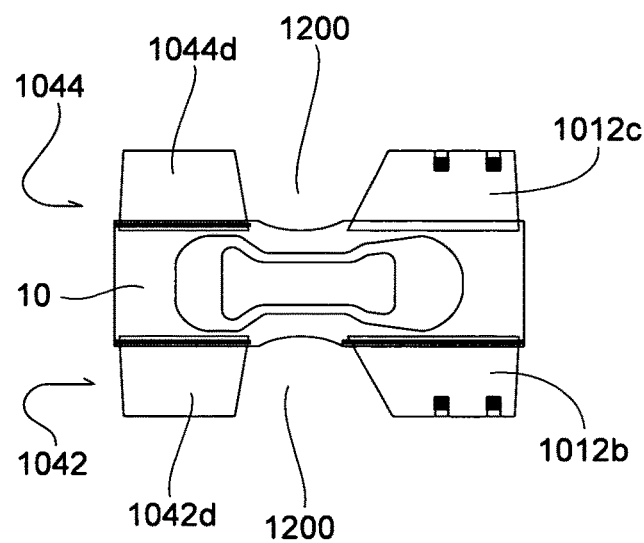
FIG. 89 is a plan view of a product variation showing alternately rotated applied front ears, and alternately rotated back ears, and a die cut chassis.
Figure 90:
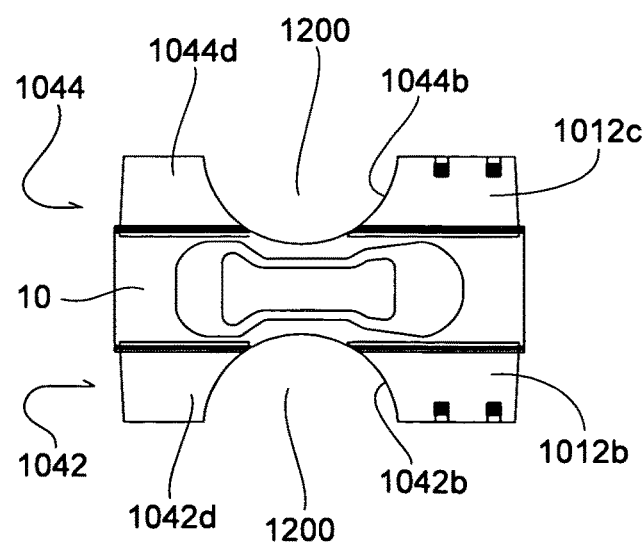
FIG. 90 is a plan view of a product variation showing alternately rotated applied front ears, and alternately rotated back ears, a die cut chassis, and die cut ears.

Referring to FIG. 89, the embodiment of FIG. 88 is shown, with the additional product feature of leg portions 1200*a* and 1200*b* of the chassis removed from the chassis, to fit around the leg of a wearer Referring to FIG. 90, the embodiment of FIG. 89 is shown with the additional product feature of chips 1230 having been removed from both the front ear and back ear portions of the product, for instance using the severing and chip removal pattern of FIG. 76.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A disposable product comprising:
   a front and back left wing;
   a front and back right wing;
   said front and back wings coupled at an inboard edge of said front and back wings to a chassis web carrying an absorbent core, said chassis web having a back waist edge and a front waist edge, said chassis web extending in a lengthwise direction from said back waist edge to said front waist edge, said chassis web also extending in a widthwise direction between said back left ring and said back right wing;
   a left stretchable web coupled to said back left wing at an outboard edge of said back left wing;
   a right stretchable web coupled to said back left wing at an outboard edge of said back right wing;
   a left ear coupled to said left stretchable web, said left ear coupled to a non-woven web coupled to a first closure mechanism along less than a lengthwise direction dimension of said left ear;
   a right ear coupled to said right stretchable said right ear coupled to a non-woven web coupled to a second closure mechanism along less than a lengthwise direction dimension of said left ear;
   said back right and left wings further comprising a back waist edge, and a leg opening facing edge;
   said left and right ears having a back waist edge;
   said chassis web having a back waist edge;

said back right wing back waist edge and said back left wing back waist edge spaced apart from said chassis back waist edge chassis in said lengthwise direction at a first distance from said chassis web back waist edge;

said first closure mechanism separated from said back left wing in said widthwise direction by a bonded portion between said back left ear and back left wing, and by a widthwise portion of said back left ear; and said second closure mechanism separated from said back right wing in said widthwise direction by a bonded portion between said back right ear and back right wing, and by a widthwise portion of said back right ear.

2. A disposable product according to claim 1, said product further comprising:
said from left and right wings comprising a first web of material, said back left and right wings comprising a second web of material.

3. A disposable product according to claim 1, said product further comprising:
said ears shorter in said lengthwise direction than said outboard edge of said wings.

4. A disposable product according to claim 1, said product further comprising:
said back right wing wick waist edge, said chassis web back waist edge, and said back left wing back waist edge, and said back left ear back waist edge defining a staggered full product back waist edge.

5. A disposable product according to claim 1, said product further comprising:
said left ear and said right ear spaced apart in said lengthwise direction at a second distance from said chassis web back waist edge.

6. A disposable product comprising:
a front and back left wing;
a front and back right wing;
said front and back wings coupled at an inboard edge of said front and back wings to a chassis web carrying an absorbent core, said chassis web having a back waist edge and a front waist edge, said chassis web extending in a lengthwise direction from said back waist edge to said front waist edge, said chassis web also extending in a widthwise direction between said back left wing and said back right wing;

a left stretchable web coupled to said back left wing at an outboard edge of said back left wing;
a right stretchable web coupled to said back left wing at an outboard edge of said back right wing;
a left ear coupled to said left stretchable web, said left ear coupled to a non-woven web coupled to a first closure mechanism along less than a lengthwise direction dimension of said left ear; and
a right ear coupled to said right stretchable web, said right ear coupled to a non-woven web coupled to a second closure mechanism along less than a lengthwise direction dimension of said left ear.

7. A disposable product comprising:
a front and back left wing;
a front and back right wing;
said front and back wings coupled at an inboard edge of said front and back wings to a chassis web carrying an absorbent core, said chassis web having a back waist edge and a front waist edge, said chassis web extending in a lengthwise direction from said back waist edge to said front waist edge, said chassis web also extending in a widthwise direction between said back left wing and said back right wing;
a left stretchable web coupled to said back left wing at an outboard edge of said back left wing;
a right stretchable web coupled to said back left wing at an outboard edge of said back right wing;
a left ear coupled to said left stretchable web, said left ear coupled to a non-woven web coupled to a first closure mechanism along less than a lengthwise direction dimension of said left ear;
a right ear coupled to said right stretchable web, said right ear coupled to a non-woven web coupled to a second closure mechanism along less than a lengthwise direction dimension of said left ear;
said back right and left wings further comprising a back waist edge;
said left and right ears having a back waist edge;
said chassis web having a back waist edge; and
said back right wing back waist edge and said back left wing back waist edge spaced apart from said chassis back waist edge chassis in said lengthwise direction at a first distance from said chassis web back waist edge.

* * * * *